United States Patent
Chaparro Riggers et al.

(10) Patent No.: US 11,702,474 B2
(45) Date of Patent: Jul. 18, 2023

(54) ANTIBODIES SPECIFIC FOR CD47, PD-L1, AND USES THEREOF

(71) Applicant: Pfizer Inc., New York, NY (US)

(72) Inventors: Javier Fernando Chaparro Riggers, San Mateo, CA (US); Shih-Hsun Chen, San Diego, CA (US); Sheng Ding, Foster City, CA (US); Pawel Kamil Dominik, San Diego, CA (US); Shahram Salek-Ardakani, La Jolla, CA (US); Jessica Lynn Stanfield, San Diego, CA (US); Thomas John Van Blarcom, Oakland, CA (US)

(73) Assignee: Pfizer Inc., New York, NY (US)

( * ) Notice: Subject to any disclaimer, the term of this patent is extended or adjusted under 35 U.S.C. 154(b) by 107 days.

(21) Appl. No.: 17/120,935

(22) Filed: Dec. 14, 2020

(65) Prior Publication Data

US 2021/0179716 A1 Jun. 17, 2021

Related U.S. Application Data

(60) Provisional application No. 63/110,693, filed on Nov. 6, 2020, provisional application No. 62/949,120, filed on Dec. 17, 2019.

(51) Int. Cl.
  *C07K 16/28* (2006.01)
  *A61P 35/00* (2006.01)
  *A61K 39/00* (2006.01)

(52) U.S. Cl.
  CPC .......... *C07K 16/2827* (2013.01); *A61P 35/00* (2018.01); *C07K 16/2803* (2013.01); *A61K 2039/505* (2013.01); *C07K 2317/31* (2013.01); *C07K 2317/33* (2013.01); *C07K 2317/51* (2013.01); *C07K 2317/515* (2013.01); *C07K 2317/52* (2013.01); *C07K 2317/56* (2013.01); *C07K 2317/73* (2013.01); *C07K 2317/76* (2013.01); *C07K 2317/92* (2013.01); *C07K 2317/94* (2013.01)

(58) Field of Classification Search
  CPC ............ C07K 16/2827; C07K 16/2803; C07K 2317/31; C07K 2317/33; C07K 2317/51; C07K 2317/515; C07K 2317/52; C07K 2317/56; C07K 2317/73; C07K 2317/76; C07K 2317/92; C07K 2317/94; A61P 35/00; A61K 2039/505; A61K 45/06
  See application file for complete search history.

(56) References Cited

U.S. PATENT DOCUMENTS

| | | |
|---|---|---|
| 2016/0108123 A1 | 4/2016 | Freeman et al. |
| 2019/0233528 A1 | 8/2019 | Srivatsa Srinivasan et al. |
| 2019/0359705 A1 | 11/2019 | Chi et al. |
| 2020/0062858 A1 | 2/2020 | Borras et al. |
| 2020/0157223 A1 | 5/2020 | Song et al. |
| 2020/0270345 A1 | 8/2020 | Solovyev et al. |
| 2020/0354458 A1 | 11/2020 | Guo et al. |

FOREIGN PATENT DOCUMENTS

| | | |
|---|---|---|
| EP | 3722322 A1 | 10/2020 |
| WO | 2009/091601 | 7/2009 |
| WO | 2009/131453 | 10/2009 |
| WO | 2010/032060 | 3/2010 |
| WO | 2014/087248 | 6/2014 |
| WO | 2014/149477 | 9/2014 |
| WO | 2016/118754 | 7/2016 |
| WO | 2017/035480 | 3/2017 |
| WO | 2017/049251 | 3/2017 |
| WO | 2017/121771 | 7/2017 |
| WO | 2017/127707 | 7/2017 |
| WO | 2017/180519 | 10/2017 |
| WO | 2017181033 | 10/2017 |
| WO | 2017/196793 | 11/2017 |
| WO | 2018/075960 | 4/2018 |
| WO | 2018/137705 | 8/2018 |
| WO | 2018/165015 | 9/2018 |
| WO | 2018/175790 | 9/2018 |
| WO | 2018/176132 | 10/2018 |
| WO | 2019/079548 | 4/2019 |
| WO | 2019/079549 | 4/2019 |
| WO | 2019/109876 | 6/2019 |
| WO | 2019144895 | 8/2019 |
| WO | 2019179434 | 9/2019 |
| WO | 2020/047651 | 3/2020 |
| WO | 2020/072445 | 4/2020 |
| WO | 2020128893 | 6/2020 |
| WO | 2020/142659 | 7/2020 |
| WO | 2020/198370 | 10/2020 |
| WO | 2020/259605 | 12/2020 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
(Continued)

*Primary Examiner* — Nelson B Moseley, II

(74) *Attorney, Agent, or Firm* — Stephen E. Moyer

(57) ABSTRACT

Antibodies that specifically bind to CD47 and antibodies that specifically bind to PD-L1 are provided, as well as CD47/PD-L1 bispecific antibodies. Also provided are uses of these antibodies, and related compositions and methods.

27 Claims, 10 Drawing Sheets

Figure 1:
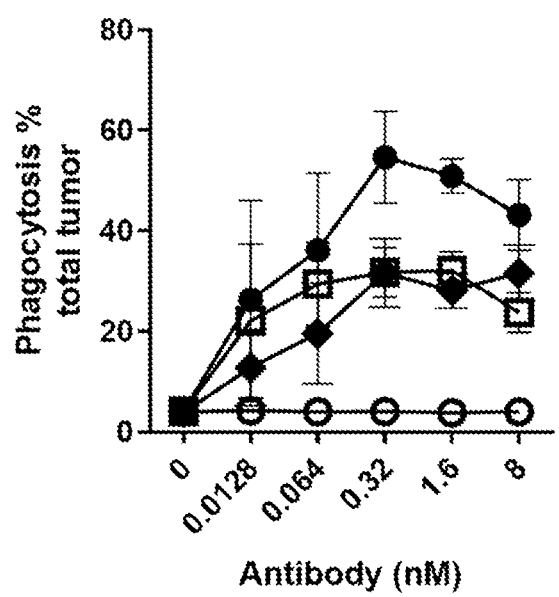

Specification includes a Sequence Listing.

(56) References Cited

OTHER PUBLICATIONS

Lin et al. (African Journal of Biotechnology, 10(79):18294-18302, 2011).*
Xiaojuan Liu et al: "Dual Targeting of Innate and Adaptive Checkpoints on Tumor Cells Limits Immune Evasion", Cell Reports, vol. 24, No. 8, Aug. 21, 2018, pp. 2101-2111.
Camilla De Nardis et al: "A new approach for generating bispecific antibodies based on a common light chain format and the stable architecture of human immunoglobulin G 1", Journal of Biological Chemistry, vol. 292, No. 35, Sep. 1, 2017, pp. 14706-14717.
Suurs Frans V et al: "A review of bispecific antibodies and antibody constructs in oncology and clinical challenges", Pharmacology and Therapeutics, Elsevier, GB, vol. 201, Apr. 24, 2019, pp. 103-119.

* cited by examiner

ANTIBODIES SPECIFIC FOR CD47, PD-L1, AND USES THEREOF

CROSS-REFERENCE TO RELATED APPLICATIONS

This application claims the benefit of U.S. Provisional Patent Application No. 62/949,120 filed Dec. 17, 2019 and 63/110,693 filed Nov. 6, 2020, both of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC072562A_SEQ_Listing_ST25.txt" created on Nov. 20, 2020 and having a size of 54 KB. The sequence listing contained in this .txt file is part of the specification and is incorporated herein by reference in its entirety.

FIELD

The present invention relates to antibodies that specifically bind to one or both of CD47 and PD-L1. The present invention further relates to bispecific antibodies that specifically bind to CD47 and PD-L1. The present invention also pertains to related molecules, e.g. nucleic acids which encode such antibodies or bispecific antibodies, compositions, and related methods, e.g., methods for producing and purifying such antibodies and bispecific antibodies, and their use in diagnostics and therapeutics.

BACKGROUND

The protein CD47 is overexpressed on a variety of tumor types (e.g. ovarian, lung, head and neck) and correlated with poor survival in patients. CD47 binds to its ligand SIRPα, an innate immune checkpoint, expressed on myeloid cells such as macrophages and dendritic cells (DCs) to suppress their activity. This enables tumor cells that overexpress CD47 to escape the innate immune surveillance. CD47 is also expressed on healthy cells such as red blood cells (RBCs) and platelets in peripheral blood, and the blockade of the CD47-SIRPα interaction by monoclonal antibodies has been shown to deplete those cells, resulting in dose limiting toxicities in some circumstances.

Anti-PD-L1 immunotherapies that block binding of PD-L1 on tumor or antigen presenting cells to PD-1 on T cells have delivered results in patients with multiple types of cancer (e.g. NSCLC, RCC, HCC, HNSCC, lymphoma, Merkel cell carcinoma). However, even in these anti-PD-L1 sensitive tumor types, many patients do not respond to the treatment. In addition to the tumor types listed above, many other tumor types with low anti-PD-(L)1 sensitivity are also enriched with CD47.

Accordingly, given the various limitations of current anti-CD47 antibody and anti-PD-L1 antibody therapeutics, improved molecules targeting CD47 and PD-L1 are needed.

SUMMARY

Provided herein are antibodies that specifically bind to CD47, antibodies that specifically bind to PD-L1, and bispecific antibodies that specifically bind to CD47 and PD-L1. Also provided herein are related nucleic acids, compositions, and methods of making and using the antibodies.

In some embodiments, provided herein is an antibody which specifically binds to CD47, wherein the antibody comprises a heavy chain variable region (VH) comprising a VH complementarity determining region one (VH CDR1), a VH complementarity determining region two (VH CDR2), and a VH complementarity determining region three (VH CDR3) of the VH sequence as shown in SEQ ID NO: 1, 3, 7, 8, or 9. Optionally, the VH comprises (i) a VH CDR1 comprising the amino acid sequence of SEQ ID NO: 13, 14, 15, 22, 23, 25, 26, 27, 31, 32, 33, 37, 38, or 39; (ii) a VH CDR2 comprising the amino acid sequence of SEQ ID NO: 16, 17, 28, 29, 34, or 35; and (iii) a VH CDR3 comprising the amino acid sequence of SEQ ID NO: 18, 24, 30, 36, or 40. Optionally, the antibody further comprises a light chain variable region (VL) comprising a VL complementarity determining region one (VL CDR1), a VL complementarity determining region two (VL CDR2), and a VL complementarity determining region three (VL CDR3) of the VL sequence as shown in SEQ ID NO: 2 or 6. Optionally, the VL comprises (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55.

In some embodiments provided herein involving an antibody that specifically binds to CD47, the VH comprises (i) a VH CDR1 comprising the amino acid sequence of SEQ ID NO: 13, 14, or 15; (ii) a VH CDR2 comprising the amino acid sequence of SEQ ID NO: 16 or 17; and (iii) a VH CDR3 comprising the amino acid sequence of SEQ ID NO: 18. Optionally, the VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21. Optionally, the VH comprises the amino acid sequence of SEQ ID NO: 1, 3, 7, 8, or 9. Optionally, the VL comprises the amino acid sequence of SEQ ID NO: 2 or 6. Optionally, the VH comprises the amino acid sequence of SEQ ID NO: 1 or 3 and the VL comprises the amino acid sequence of SEQ ID NO: 2. Optionally, one or both of: i) the VH comprises a variant of the amino acid sequence of SEQ ID NO: 1, wherein the variant sequence comprises one, two, three, four, five, six, seven, or eight amino acid substitutions as compared to SEQ ID NO: 1; and ii) the VL comprises a variant of the amino acid sequence of SEQ ID NO: 2, wherein the variant sequence comprises one, two, three, four, five, six, seven, or eight amino acid substitutions as compared to SEQ ID NO: 2. Optionally, the substitutions are conservative amino acid substitutions. Optionally, the substitutions are in residues that are not within a CDR region.

In some embodiments, provided herein is an antibody which specifically binds to CD47, wherein the antibody comprises a VH comprising the amino acid sequence of SEQ ID NO: 1 and a VL comprising the amino acid sequence of SEQ ID NO: 2. In some embodiments, provided herein is an antibody which specifically binds to CD47, wherein the antibody comprises a VH comprising the amino acid sequence of SEQ ID NO: 3 and a VL comprising the amino acid sequence of SEQ ID NO: 2.

In some embodiments, provided herein is an isolated antibody which specifically binds to CD47, wherein the antibody comprises a VH comprising the VH sequence of QVQLVQSGAEVKKPGSSVKVSCK-ASGYTFTNYAISWVRQAPGQGLEWMGGISPLFGT ANYAQKFQGRVTITADESTSTAYMELSSLRSED-TAVYYCARDGGRSSDVGWYVGAM DVWGQGTLVTVSS (SEQ ID NO: 7) or a variant thereof wherein the sequence has a variant amino acid at one or more of positions 27, 30, 31, 50, 52, 53, 54, 55, 99, 100, 104, 105, 108, 113, or 114 of SEQ ID NO: 7. Optionally, the antibody further comprises a VL comprising (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55. Optionally, the VL comprises the amino acid sequence of SEQ ID NO: 2 or 6.

In some embodiments, provided herein is an isolated antibody which specifically binds to CD47, wherein the antibody comprises a VH comprising the VH sequence of QVQLVQSGAEVKKPGSSVKVSCK-ASGYTFTNYAISWVRQAPGQGLEWMGGISPLFGT ANYAQKFQGRVTITADESTSTAYMELSSLRSED-TAVYYCARDGGRSSDVGWYVGAM DVWGQGTLVTVSS (SEQ ID NO: 7) or a variant thereof wherein a) the amino acid at position 27 is G (Y27G); b) the amino acid at position 30 is S (T30S); c) the amino acid at position 31 is S (N31S); d) the amino acid at position 50 is R (G50R); e) the amino acid at position 52 is I (S52I); f) the amino acid at position 53 is G (P53G); g) the amino acid at position 54 is I (L54I); h) the amino acid at position 55 is L (F55L); i) the amino acid at position 99 is E (D99E); j) the amino acid at position 100 is A, S, Q, or V (G100A, G100S, G100Q, or G100V); k) the amino acid at position 105 is E (D105E); l) the amino acid at position 108 is Y, F, or A (W108Y, W108F, or W108A); m) the amino acid at position 113 is L or I (M113L or M113I); n) the amino acid at position 114 is E (D114E); o) the amino acid at position 53 is G and the amino acid at position 105 is E; p) the amino acid at position 53 is G and the amino acid at position 114 is E; q) the amino acid at position 54 is A and the amino acid at position 114 is E; r) the amino acid at position 54 is A and the amino acid at position 102 is A; s) the amino acid at position 54 is A and the amino acid at position 104 is E; t) the amino acid at position 27 is G, the amino acid at position 54 is I; and the amino acid at position 100 is A; u) the amino acid at position 27 is G, the amino acid at position 54 is I, the amino acid at position 100 is A, and the amino acid at position 113 is L; v) the amino acid at position 27 is G, the amino acid at position 54 is I, the amino acid at position 100 is A, and the amino acid at position 113 is I; w) the amino acid at position 30 is S, the amino acid at position 31 is S, the amino acid at position 54 is I, and the amino acid at position 100 is A; x) the amino acid at position 27 is G, the amino acid at position 31 is S, the amino acid at position 54 is I, the amino acid at position 100 is A, and the amino acid at position 113 is L; y) the amino acid at position 30 is S, the amino acid at position 31 is S, the amino acid at position 54 is I, the amino acid at position 100 is A, and the amino acid at position 113 is L; z) the amino acid at position 30 is S, the amino acid at position 31 is S, the amino acid at position 54 is I, the amino acid at position 100 is A, and the amino acid at position 113 is I; or aa) the amino acid at position 30 is S, the amino acid at position 31 is S, the amino acid at position 54 is I, the amino acid at position 100 is A, the amino acid at position 108 is Y, and the amino acid at position 113 is L. Optionally, the antibody further comprises a VL comprising (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55. Optionally, the VL comprises the sequence of SEQ ID NO: 2 or 6.

In some embodiments, provided herein is an antibody which specifically binds to PD-L1, wherein the antibody comprises a VH comprising a VH CDR1, a VH CDR2, and a VH CDR3 of the VH having the amino acid of SEQ ID NO: 4, 5, 10, 11, or 12. Optionally, the VH comprises (i) a VH CDR1 comprising the amino acid sequence of SEQ ID NO: 41, 42, 43, 47, 48, or 49; (ii) a VH CDR2 comprising the amino acid sequence of SEQ ID NO: 44, 45, 50, 51, 58, or 59; and (iii) a VH CDR3 comprising the amino acid sequence of SEQ ID NO: 46, 52, 56, 57, or 60. Optionally, the antibody further comprises a light chain variable region (VL) comprising a VL CDR1, a VL CDR2, and a VL CDR3 of the VL sequence as shown in SEQ ID NO: 2 or 6. Optionally, the VL comprises (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55.

In some embodiments provided herein involving an antibody that specifically binds to PD-L1, the VH comprises (i) a VH CDR1 comprising the amino acid sequence of SEQ ID NO: 41, 42, or 43; (ii) a VH CDR2 comprising the amino acid sequence of SEQ ID NO: 44 or 45; and (iii) a VH CDR3 comprising the amino acid sequence of SEQ ID NO: 46. Optionally, the VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21. Optionally, the VH comprises the amino acid sequence of SEQ ID NO: 4, 5, 10, 11, or 12. Optionally, the VL comprises the amino acid sequence of SEQ ID NO: 2 or 6. Optionally, the VH comprises the sequence amino acid of SEQ ID NO: 4 and the VL comprises the amino acid sequence of SEQ ID NO: 2. Optionally, one or both of: i) the VH comprises a variant of the amino acid sequence of SEQ ID NO: 4, wherein the variant sequence comprises one, two, three, four, five, six, seven, or eight amino acid substitutions as compared to SEQ ID NO: 4; and ii) the VL comprises a variant of the amino acid sequence of SEQ ID NO: 2, wherein the variant sequence comprises one, two, three, four, five, six, seven, or eight amino acid substitutions as compared to SEQ ID NO: 2. Optionally, the substitutions are conservative amino acid substitutions. Optionally, the substitutions are in residues that are not within a CDR region.

In some embodiments, provided herein is an antibody which specifically binds to PD-L1, wherein the antibody comprises a VH comprising the amino acid sequence as shown in SEQ ID NO: 4 and a VL comprising the amino acid sequence as shown in SEQ ID NO: 2. In some embodiments, provided herein is an antibody which specifically binds to PD-L1, wherein the antibody comprises a VH comprising the amino acid sequence as shown in SEQ ID NO: 5 and a VL comprising the amino acid sequence as shown in SEQ ID NO: 6.

In some embodiments, provided herein is an isolated antibody which specifically binds to PD-L1, wherein the antibody comprises a VH comprising the VH sequence of EVQLVESGGGLVKPGGSLRLS-CAASGFTFSNAWMNWVRQAPGK-GLEWVGRIKTKAD GGTTDYAAPVKGRFTISRDD-SKNTLYLQMNSLKTEDTAVYYCTTDPGSYWDSVYG GM DYWGQGTLVTVSS (SEQ ID NO: 11) or a variant thereof wherein the sequence has a variant amino acid at one or more of positions 56, 57, 61, 62, 103, 104, 105, 107, 109, 112, 113 of SEQ ID NO: 11. Optionally, the antibody further comprises a VL comprising (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55. Optionally, the VL comprises the amino acid sequence of SEQ ID NO: 2 or 6.

In some embodiments, provided herein is an isolated antibody which specifically binds to PD-L1, wherein the antibody comprises a VH comprising the VH sequence of EVQLVESGGGLVKPGGSLRLS-CAASGFTFSNAWMNWVRQAPGK-GLEWVGRIKTKAD GGTTDYAAPVKGRFTISRDD-SKNTLYLQMNSLKTEDTAVYYCTTDPGSYWDSVYGGMDYWGQGTLVTVSS (SEQ ID NO: 11) or a variant thereof wherein a) the amino acid at position 56 is E (D56E) and the amino acid at position is 57 is E or A (G57E or G57A); b) the amino acid at position 61 is Q, E, A, or S, (D61Q, D61E, D61A, or D61S) and the amino acid at position 62 is E, S, Q, A (Y62E, Y62S, Y62Q, or Y62A); c) the amino acid at position 103 is I (G103I); d) the amino acid at position 104 is A, H, Y, E, or I (S104A, S104H, S104Y, S104E, or S104I); e) the amino acid at position 105 is H (Y105H); f) the amino acid at position 107 is S, L, or Y (D107S, D107L, or D107Y); g) the amino acid at position 109 is S (V109S); h) the amino acid at position 112 is A or S (G112A or G112S); or i) the amino acid at position 113 is L (M113L). Optionally, the antibody further comprises a VL comprising (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55. Optionally, the VL comprises the amino acid sequence of SEQ ID NO: 2 or 6.

In some embodiments of an antibody provided herein, the antibody is selected from the group consisting of a Fab fragment, a Fab' fragment, a F(ab')$_2$ fragment, an Fd fragment, an Fv fragment, a single chain Fv fragment (scFv), a disulfide stabilized Fv (dsFv) fragment, a single domain antibody (dAb) fragment, a monoclonal antibody, a chimeric antibody, a bispecific antibody, a trispecific antibody, a multispecific antibody, a bispecific heterodimeric diabody, a bispecific heterodimeric IgG, a polyclonal antibody, a labeled antibody, a humanized antibody, a human antibody, and fragments thereof. Optionally, the antibody comprises a human or humanized VH framework and a human or humanized VL framework. Optionally, the antibody is a bispecific antibody.

In some embodiments of a bispecific antibody provided herein, the bispecific antibody specifically binds to CD47 and PD-L1. Optionally, the antibody comprises a first antigen binding portion and a second antigen binding portion, wherein the first antigen binding portion specifically binds to CD47 and the second antigen binding portion specifically binds to PD-L1, wherein the first antigen binding portion comprises a VH and a VL, wherein the second antigen binding portion comprises a VH and a VL, and wherein the amino acid sequence of the VL of the first antigen binding portion and the amino acid sequence of the VL of the second antigen binding portion have the same amino acid sequence. Optionally, the amino acid sequence of the VL of the first antigen binding portion and the amino acid sequence of the VL of the second antigen binding portion comprise the amino acid sequence as shown in SEQ ID NO: 2 or a variant thereof comprising one, two, three, four, five, six, seven, or eight amino acid substitutions as compared to SEQ ID NO: 2. Optionally, the amino acid sequence of the VL of the first antigen binding portion and the amino acid sequence of the VL of the second antigen binding portion comprise the amino acid sequence as shown in SEQ ID NO: 6 or a variant thereof comprising one, two, three, four, five, six, seven, or eight amino acid substitutions as compared to SEQ ID NO: 6. Optionally, the substitutions are conservative amino acid substitutions. Optionally, the substitutions are in residues that are not within a CDR region.

In some embodiments, provided herein is a CD47/PD-L1 bispecific antibody comprising a first antigen binding portion that specifically binds to CD47 and a second antigen binding portion that specifically binds to PD-L1, wherein the first antigen binding portion comprises a VH and a VL, wherein the second antigen binding portion comprises a VH and a VL, and wherein one, two, three, or all four of: a) the first antigen binding portion VH comprises a VH CDR1, a VH CDR2, and VH CDR3 of the VH sequence as shown in SEQ ID NO: 1, 3, 7, 8, or 9; b) the first antigen binding portion VL comprises a VL CDR1, a VL CDR2, and VL CDR3 of the VL sequence as shown in SEQ ID NO: 2; c) the second antigen binding portion VH comprises a VH CDR1, a VH CDR2, and VH CDR3 of the VH sequence as shown in SEQ ID NO: 4, 5, 10, 11, or 12; and d) the second antigen binding portion VL comprises a VL CDR1, a VL CDR2, and VL CDR3 of the VL sequence as shown in SEQ ID NO: 2 or 6. Optionally, one, two, three, or all four of: a) the first antigen binding portion VH comprises (i) a VH CDR1 comprising the amino acid sequence of SEQ ID NO: 13, 14, 15, 22, 23, 25, 26, 27, 31, 32, 33, 37, 38, or 39; (ii) a VH CDR2 comprising the amino acid sequence of SEQ ID NO: 16, 17, 28, 29, 34, or 35; and (iii) a VH CDR3 comprising the amino acid sequence of SEQ ID NO: 18, 24, 30, 36, or 40; b) the first antigen binding portion VL comprises (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55; c) the second antigen binding portion VH comprises (i) a VH CDR1 comprising the amino acid sequence of SEQ ID NO: 41, 42, 43, 47, 48, or 49; (ii) a VH CDR2 comprising the amino acid sequence of SEQ ID NO: 44, 45, 50, 51, 58, or 59; and (iii) a VH CDR3 comprising the amino acid sequence of SEQ ID NO: 46, 52, 56, 57, or 60; and d) the second antigen binding portion VL comprises (i) a VL CDR1 comprising the amino acid sequence of SEQ ID NO: 19 or 53; (ii) a VL CDR2 comprising the amino acid sequence of SEQ ID NO: 20 or 54; and (iii) a VL CDR3 comprising the amino acid sequence of SEQ ID NO: 21 or 55. Optionally, one, two, three, or all four of: a) the first antigen binding portion VH comprises (i) a VH CDR1 comprising the amino acid sequence of SEQ ID NO: 13, 14, or 15; (ii) a VH CDR2 comprising the amino acid sequence of SEQ ID NO: 16 or 17; and (iii) a VH CDR3 comprising the amino acid sequence of SEQ ID NO: 18; b) the first antigen binding portion VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21; c) the second antigen binding portion VH comprises (i) a VH CDR1 comprising the amino acid sequence of SEQ ID NO: 41, 42, or 43; (ii) a VH CDR2 comprising the amino acid sequence of SEQ ID NO: 44 or 45; and (iii) a VH CDR3 comprising the amino acid sequence of SEQ ID NO: 46; and d) the second antigen binding portion VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21. Optionally, one, two, three, or all four of: a) the first antigen binding portion VH comprises in the amino acid sequence of SEQ ID NO: 1 or 3; b) the first antigen binding portion VL comprises the amino acid sequence of SEQ ID NO: 2; c) the second antigen binding portion VH comprises the amino acid sequence of SEQ ID NO: 4; and d) the second antigen binding portion VL comprises the amino acid sequence of SEQ ID NO: 2.

In some embodiments, provided herein is a CD47/PD-L1 bispecific antibody comprising a first antigen binding portion that specifically binds to CD47 and a second antigen binding portion that specifically binds to PD-L1, wherein the antibody comprises a first antigen binding portion VH comprising the amino acid sequence as shown in SEQ ID NO: 1, a first antigen binding portion VL comprising the amino acid sequence as shown in SEQ ID NO: 2, a second antigen binding portion VH comprising the amino acid sequence as shown in SEQ ID NO: 4, and a second antigen binding portion VL comprising the amino acid sequence as shown in SEQ ID NO: 2.

In some embodiments, provided herein is a CD47/PD-L1 bispecific antibody comprising a first antigen binding portion that specifically binds to CD47 and a second antigen binding portion that specifically binds to PD-L1, wherein the antibody comprises a first antigen binding portion VH comprising the amino acid sequence as shown in SEQ ID NO: 3, a first antigen binding portion VL comprising the amino acid sequence as shown in SEQ ID NO: 2, a second antigen binding portion VH comprising the amino acid sequence as shown in SEQ ID NO: 4, and a second antigen binding portion VL comprising the amino acid sequence as shown in SEQ ID NO: 2.

In some embodiments provided herein is an isolated antibody comprising a first antigen binding portion that specifically binds to CD47 and a second antigen binding portion that specifically binds to PD-L1, wherein the first antigen binding portion comprises a VH and a VL, wherein the second antigen binding portion comprises a VH and a VL, and wherein a) the first antigen binding portion VH comprises (i) a VH CDR1 comprising the amino acid sequence of SEQ ID NO: 13, 14, or 15; (ii) a VH CDR2 comprising the amino acid sequence of SEQ ID NO: 16 or 17; and (iii) a VH CDR3 comprising the amino acid sequence of SEQ ID NO: 18; and b) the second antigen binding portion VH comprises (i) a VH CDR1 comprising the amino acid sequence of SEQ ID NO: 41, 42, or 43; (ii) a VH CDR2 comprising the amino acid sequence of SEQ ID NO: 44 or 45; and (iii) a VH CDR3 comprising the amino acid sequence of SEQ ID NO: 46. Optionally, the first antigen binding portion VH comprises the amino acid sequence as shown in SEQ ID NO: 1, and the second antigen binding portion VH comprises the amino acid sequence as shown in SEQ ID NO: 4. Optionally, a) the first antigen binding portion VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21; and b) the second antigen binding portion VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21. Optionally, the first antigen binding portion VL comprises the amino acid sequence as shown in SEQ ID NO: 2 and the second antigen binding portion VL comprises the amino acid sequence as shown in SEQ ID NO: 2

In some embodiments, provided herein is an isolated bispecific antibody comprising a first antigen binding portion that specifically binds to CD47 and a second antigen binding portion that specifically binds to PD-L1, wherein the first antigen binding portion comprises the VH and VL of any anti-CD47 antibody provided herein, and wherein the second antigen binding portion comprises the VH and VL of any anti-PD-L1 antibody provided herein.

In some embodiments, in a bispecific antibody provided herein the bispecific antibody comprises a Fc domain. Optionally, the Fc domain is an IgG1 Fc domain, IgG2 Fc domain, or an IgG4 Fc domain. Optionally, the first Fc chain and the second Fc chain of the Fc domain contain one or more modifications promoting the association of the first Fc chain with the second Fc chain. Optionally, the first Fc chain and the second Fc chain each comprises at least one amino acid modification as compared to a wild-type Fc chain, to form a knob or a hole, and wherein one of the Fc chains comprises a knob and the other Fc chain comprises a hole. Optionally, the knob-comprising Fc chain comprises one or both of the mutations Y349C and/or T366W, and wherein the hole-comprising Fc chain comprises one, two, three, or all four of the mutations S354C, T366S, L368A, and/or Y407V (numbering according to the EU index).

In some embodiments, provided herein is a CD47/PD-L1 bispecific antibody comprising an anti-CD47 heavy chain comprising the amino acid sequence of SEQ ID NO: 61 or 63 and an anti-PD-L1 heavy chain comprising the amino acid sequence of SEQ ID NO: 64. Optionally, the antibody further comprises an anti-CD47 light chain comprising the amino acid sequence of SEQ ID NO: 62 and an anti-PD-L1 light chain comprising the amino acid sequence of SEQ ID NO: 62. Optionally, the anti-CD47 light chain and the anti-PD-L1 light chain have the same amino acid sequence.

In some embodiments, provided herein is a CD47/PD-L1 bispecific antibody, wherein the antibody comprises a first antibody heavy chain, a second antibody heavy chain, a first antibody light chain, and a second antibody light chain; wherein the first antibody heavy chain comprises the amino acid sequence of SEQ ID NO: 61 and the second antibody heavy chain comprises the amino acid sequence of in SEQ ID NO: 64; and wherein both the first antibody light chain and the second antibody light chain comprise the amino acid sequence of SEQ ID NO: 62.

In some embodiments, provided herein is a CD47/PD-L1 bispecific antibody, wherein the antibody comprises a first antibody heavy chain, a second antibody heavy chain, a first antibody light chain, and a second antibody light chain; wherein the first antibody heavy chain comprises the amino acid sequence of SEQ ID NO: 63 and the second antibody heavy chain comprises the amino acid sequence of in SEQ ID NO: 64; and wherein both the first antibody light chain and the second antibody light chain comprise the amino acid sequence of SEQ ID NO: 62.

In an antibody provided herein, in some embodiments, one or more the heavy chains in the antibody may lack the C-terminal lysine. For example, in some embodiments, in a CD47/PD-L1 bispecific antibody provided herein, one or more heavy chains in the antibody may lack the C-terminal lysine. For example, in a bispecific antibody provided herein comprising the amino acid sequence of SEQ ID NO: 61, 63, or 64, also included herein are antibodies that lack the C-terminal lysine in the amino acid sequence of SEQ ID NO: 61, 63, or 64.

In some embodiments of a CD47/PD-L1 bispecific antibody provided herein, the affinity of the anti-PD-L1 antibody variable region for PD-L1 is greater than the affinity of the anti-CD47 antibody variable region for CD47. Optionally, the affinity of the anti-PD-L1 antibody variable region for PD-L1 is between 100-fold and 1000-fold or between 1000-fold and 5000-fold greater than the affinity of the anti-CD47 antibody variable region for CD47. Optionally, one or both of: i) the anti-PD-L1 antibody variable region $K_D$ is between 0.1-1 nM or between 0.05-5 nM and/or ii) the anti-CD47 antibody variable region $K_D$ is between 10-500 nM, between 10-1000 nM, or between 5-1000 nM.

In some embodiments of a CD47/PD-L1 bispecific antibody provided herein, the antibody is a human, humanized, or chimeric antibody.

In some embodiments provided herein is a CD47/PD-L1 bispecific antibody that comprises a first antibody heavy chain, a second antibody heavy chain, a first antibody light chain, and a second antibody light chain, wherein one, two, or all three of: a) the first antibody heavy chain has an amino acid sequence encoded by the nucleic acid sequence of the insert of the plasmid deposited with the ATCC having ATCC Accession No. PTA-126910; b) the second antibody heavy chain has an amino acid sequence encoded by the nucleic acid sequence of the insert of the plasmid deposited with the ATCC having ATCC Accession No. PTA-126911; and c) the first antibody light chain and the second antibody light chain have an amino acid sequence encoded by the nucleic acid sequence of the insert of the plasmid deposited with the ATCC having ATCC Accession No. PTA-126912.

In some embodiments, provided herein is a pharmaceutical composition comprising a therapeutically effective amount an antibody provided herein (e.g. monospecific or a bispecific), and a pharmaceutically acceptable carrier.

In some embodiments, provided herein is a polynucleotide comprising a nucleotide sequence encoding an amino acid sequence as provided herein, a vector comprising the polynucleotide, or a host cell comprising the vector or recombinant polynucleotide. In some embodiments, provided herein is a polynucleotide comprising a nucleotide sequence of any one of SEQ ID NOs: 67-74.

In some embodiments, provided herein is a host cell that comprises one, two, or all three of: a) a recombinant polynucleotide comprising a nucleotide sequence that encodes a VH having the amino acid sequence of SEQ ID NO: 1 or 3; b) a recombinant polynucleotide comprising a nucleotide sequence that encodes a VH having the amino acid sequence of SEQ ID NO: 4; and c) a recombinant polynucleotide comprising a nucleotide sequence that encodes a VL having the amino acid sequence of SEQ ID NO: 2. Optionally, the host cell comprises one, two, or all three of: a) a recombinant polynucleotide comprising a nucleotide sequence that encodes a heavy chain having the amino acid sequence of SEQ ID NO: 61 or 63; b) a recombinant polynucleotide comprising a nucleotide sequence that encodes a heavy chain having the amino acid sequence of SEQ ID NO: 64; and c) a recombinant polynucleotide comprising a nucleotide sequence that encodes a light chain having the amino acid sequence of SEQ ID NO: 62. Optionally, the host cell recombinantly produces an antibody provided herein. Optionally, the host cell is a bacterial, mammalian, yeast, or insect cell line. Optionally, the mammalian cell line is a CHO cell line.

In some embodiments, provided herein is a method of producing an antibody or a bispecific antibody, comprising culturing a host cell provided herein under conditions that result in the production of an antibody or bispecific antibody provided herein, and purifying the produced antibody or bispecific antibody.

Also provided herein is use of an antibody, bispecific antibody, pharmaceutical composition, polynucleotide, vector, or host cell provided herein in the manufacture of a medicament.

Also provided herein is use of an antibody, bispecific antibody, or pharmaceutical composition provided herein for use as a medicament. Optionally, the antibody, bispecific antibody, pharmaceutical composition, or medicament is for use in the treatment of cancer.

In some embodiments, provided herein is a method of treating a disease in a subject in need thereof, the method comprising administering to the subject an effective amount of an antibody, bispecific antibody, or pharmaceutical composition provided herein. Optionally, the method of treating the disease comprises modulating or stimulating an immune response or function. Optionally, both the adaptive and the innate immune response or function are modulated or stimulated. Optionally, the disease is an infection. Optionally, the disease is cancer. Optionally, the method further comprises administering a second therapeutic agent to the subject. Optionally, the second therapeutic agent is an anti-cancer agent. Optionally, the anti-cancer agent is a TLR agonist such as TLR3 agonist, a TLR7/8 agonist or a TLR9 agonist, a CDK inhibitor such as a CDK4/6 or a CDK 2/4/6 inhibitor, or a PARP inhibitor, such as olaparib, rucaparib, niraparib, or talazoparib. Optionally, the TLR9 agonist is CpG24555, CpG10103, CpG7909 (PF-3512676), CpG1018. Optionally, the CDK inhibitor is PF-06873600 or palbociclib.

In some embodiments, the combination of a CD47/PD-L1 bispecific antibody provided herein plus a TLR agonist (e.g. TLR9 agonist) has greater anti-cancer activity than the anti-cancer activity of either agent individually. In some embodiments, the combination has synergistic anti-cancer activity.

In some embodiments, the combination of a CD47/PD-L1 bispecific antibody provided herein plus a CDK inhibitor (e.g. CDK 2/4/6 inhibitor) has greater anti-cancer activity than the anti-cancer activity of either agent individually. In some embodiments, the combination has synergistic anti-cancer activity.

In some embodiments, provided herein is a method of enhancing an immune response in a subject, the method comprising administering to the subject an effective amount of an antibody, bispecific antibody, or pharmaceutical composition provided herein.

In some embodiments, provided herein is a method of inhibiting or reducing the growth of cancer cells in a subject, the method comprising administering to the subject an effective amount of an antibody, bispecific antibody, or pharmaceutical composition provided herein. In some embodiments, an antibody, bispecific antibody, or pharmaceutical composition provided herein provided herein inhibits or reduces the growth of cancer cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of cancer cells in the absence of the antibody or a bispecific antibody.

In some embodiments, an antibody or bispecific antibody provided herein binds to cynomolgus monkey red blood cells and/or platelets with an affinity that is at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% of the affinity that it has for human red blood cells and/or platelets, respectively.

In some embodiments, provided herein is an antibody, bispecific antibody, or pharmaceutical composition provided herein for use in the methods of treatment provided herein.

In some embodiments, provided herein is an antibody, bispecific antibody, or pharmaceutical composition provided herein for use in the treatment of cancer and/or enhancing an immune response in a subject. In some embodiments, provided herein is the use of an antibody, bispecific antibody, or pharmaceutical composition provided herein in the manufacture of a medicament for use in the methods of treatment provided herein. In some embodiments the medicament is for use in treating cancer and/or enhancing an immune response in a subject.

In some embodiments provided herein involving a cancer, the cancer is gastric cancer, sarcoma, lymphoma, Hodgkin's lymphoma, leukemia, head and neck cancer, thymic cancer, epithelial cancer, salivary cancer, liver cancer, stomach cancer, thyroid cancer, lung cancer (including, for example, non-small-cell lung carcinoma), ovarian cancer, breast cancer, prostate cancer, esophageal cancer, pancreatic cancer, glioma, glioblastoma, brain tumor, leukemia, multiple myeloma, renal cell carcinoma, kidney cancer, bladder cancer, urothelial cancer, cervical cancer, choriocarcinoma, colon cancer, oral cancer, skin cancer, or melanoma.

BRIEF DESCRIPTION OF THE FIGURES/DRAWINGS

FIG. 1 depicts data from an experiment testing the effect of BsAb1 (solid circles), anti-CD47 antibody P01A11_75 (solid diamonds), anti-PD-L1 antibody P06B05_245 (empty squares), or control antibody (empty circle) on antibody-dependent cellular phagocytosis (ADCP) activity of macrophages on human NCI-H292 tumor cells. The Y-axis depicts the % of the tumor cells which have been phagocytosed at the concentration of respective antibody as shown on the X-axis.

Figure 2A:
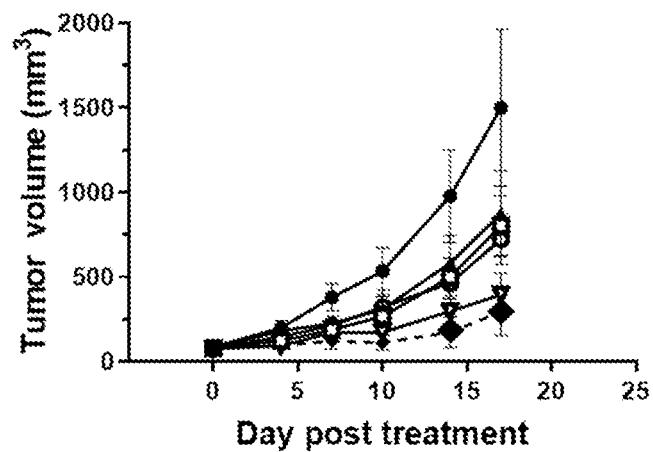
Figure 2B:
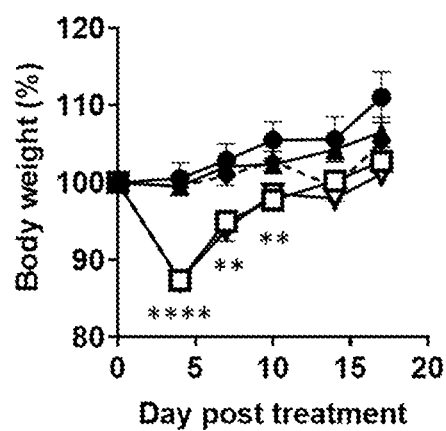
Figure 2C:
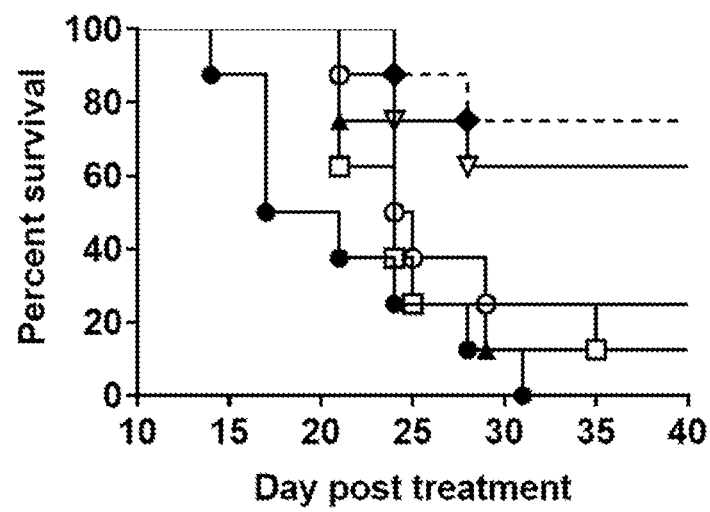

FIG. 2A, FIG. 2B, and FIG. 2C depict data from an experiment testing the antitumor efficacy of BsAb3 and other related antibodies in the CT26 mouse tumor model. In the experiment depicted in FIG. 2A, FIG. 2B, and FIG. 2C, mice harboring CT26 tumors were treated with a control antibody (solid circle), anti-CD47 monospecific antibody (empty square), anti-PD-L1 monospecific antibody (solid triangle, points connected by solid line), anti-CD47 monospecific antibody in combination with anti-PD-L1 monospecific antibody (inverted empty triangle), BsAb3 (solid diamond, points connected by dashed line), or Fc-null BsAb3 (empty circle). In FIG. 2A, the X-axis shows the days post-treatment, and the Y axis shows the tumor volume in $mm^3$. In FIG. 2B, the X-axis shows the days post-treatment, and the Y-axis shows the body weight percentage. In FIG. 2C, the X-axis shows the days post-treatment, and the Y axis shows the percent survival.

Figure 3A:
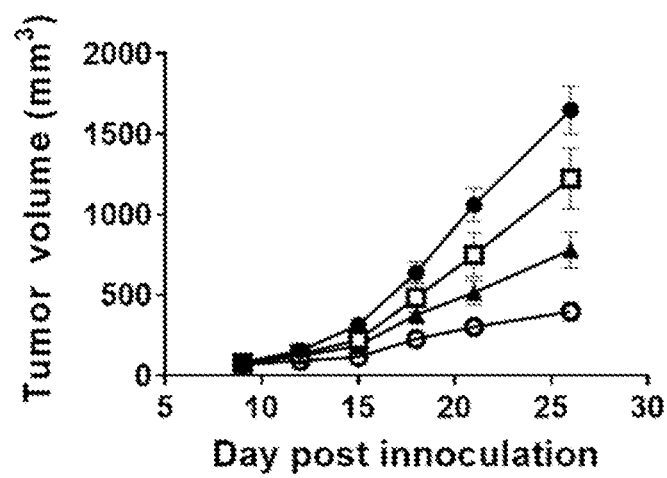
Figure 3B:
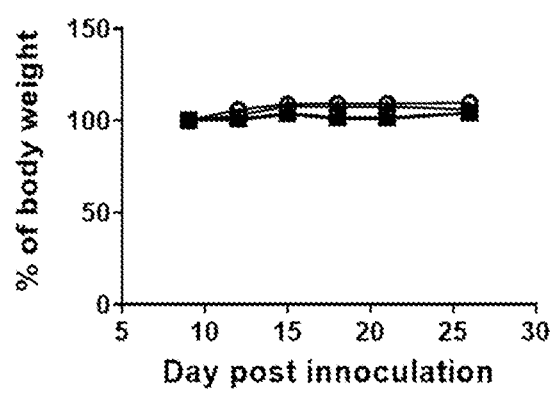

FIG. 3A and FIG. 3B depict data from an experiment testing the antitumor efficacy of different doses of BsAb3 in the MC38 mouse tumor model. In the experiment depicted in FIG. 3A and FIG. 3B, mice harboring MC38 tumors were treated with a control isotype antibody (solid circle), 10 mg/kg BsAb3 (empty square), 20 mg/kg BsAb3 (solid triangle), or 40 mg/kg BsAb3 (empty circle). In FIG. 3A, the X-axis shows the days post-tumor inoculation, and the Y axis shows the tumor volume in $mm^3$. In FIG. 3B, the X-axis shows the days post-tumor inoculation, and the Y axis shows the body weight percentage.

Figure 4A:
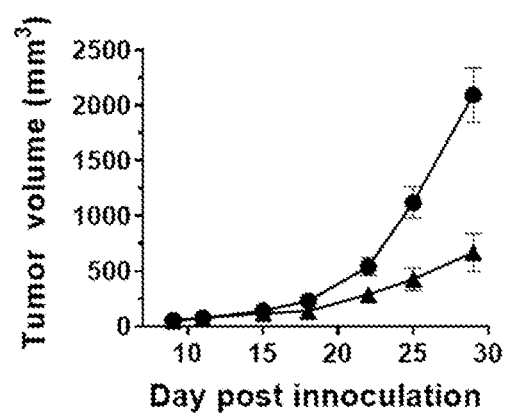
Figure 4B:
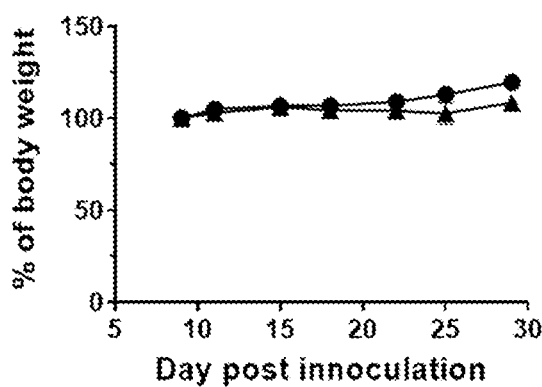

FIG. 4A and FIG. 4B depict data from an experiment testing the antitumor efficacy of BsAb3 in the B16F10 mouse tumor model. In the experiment depicted in FIG. 4A and FIG. 4B, mice harboring B16F10 tumors were treated with a control isotype antibody (solid circle) or 20 mg/kg BsAb3 (solid triangle). In FIG. 4A, the X-axis shows the days post-tumor inoculation, and the Y axis shows the tumor volume in $mm^3$. In FIG. 4B, the X-axis shows the days post-tumor inoculation, and the Y axis shows the body weight percentage.

Figure 5A:
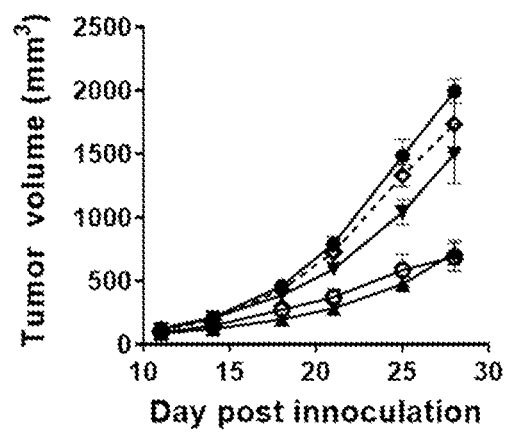
Figure 5B:
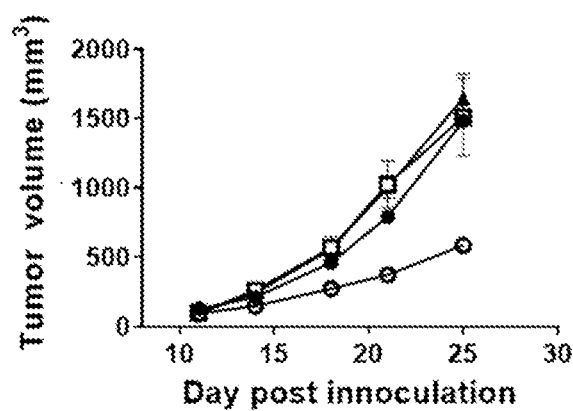

FIG. 5A, FIG. 5B, FIG. 5C, and FIG. 5D depict data from an experiment testing the antitumor efficacy of BsAb3 in mice harboring MC38 tumors when BsAb3 is co-administered with different antibodies that deplete or inhibit various classes of immune cells. In the experiment depicted in FIG. 5A, mice were treated with a control isotype antibody (solid circle), BsAb3 (empty circle), BsAb3+anti-CD8 mAb (solid inverted triangle), BsAb3+anti-CD4 mAb (solid triangle), or BsAb3+anti-CD4 mAb+anti-CD8 mAb (empty diamond). In the experiment depicted in FIG. 5B, wild-type C57BL/6 mice or BATF3−/− mice were treated with a control isotype antibody or BsAb3. FIG. 5B depicts data from wild-type mice treated with control antibody (solid circle), wild-type mice treated with BsAb3 (empty circle), BATF3−/− mice treated with control antibody (empty square) and BATF3−/− mice treated with BsAb3 (solid triangle). In the experiment depicted in FIG. 5C, mice were treated with a control isotype antibody (solid circle), BsAb3 (empty circle), or BsAb3+anti-CSF1R mAb (solid inverted triangle). In the experiment depicted in FIG. 5D, mice were treated with a control isotype antibody (solid circle), BsAb3 (empty circle), or BsAb3+anti-NK1.1 mAb (solid inverted triangle). In each of FIG. 5A, FIG. 5B, FIG. 5C, and FIG. 5D, the X-axis shows the days post-tumor inoculation, and the Y axis shows the tumor volume in $mm^3$.

Figure 6:
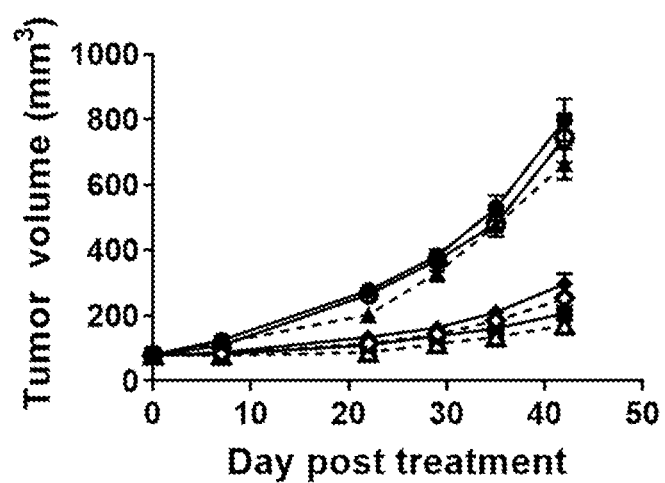

FIG. 6 depicts data from an experiment testing the antitumor efficacy of BsAb1 and BsAb2 against MDA-MB-231 human breast cancer cells in NSG immunodeficient mice. Mice harboring MDA-MB-231 tumors were treated with a control isotype antibody (solid circle), 1 mg/kg BsAb1 (solid triangle), 5 mg/kg BsAb1 (empty diamond), 10 mg/kg BsAb1 (empty triangle), 1 mg/kg BsAb2 (empty circle), 5 mg/kg BsAb2 (solid diamond), or 10 mg/kg BsAb2 (solid square). The X-axis shows the days post-treatment, and the Y axis shows the tumor volume in $mm^3$.

Figure 7:
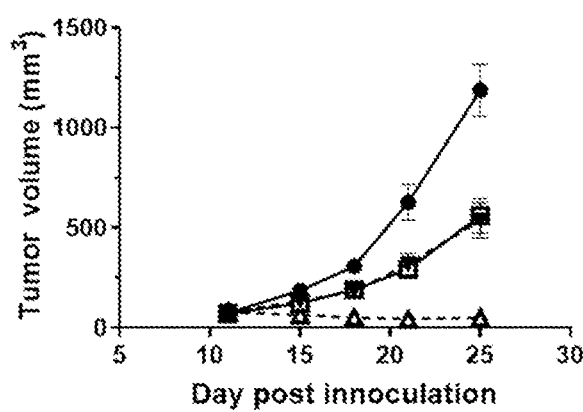

FIG. 7 depicts data from an experiment testing the antitumor efficacy of BsAb3 in combination with a TLR9 agonist in the MC38 mouse tumor model. Mice harboring MC38 tumors were treated with a control isotype antibody (solid circle), BsAb3 (empty square), a TLR9 agonist (solid inverted triangle), or both BsAb3 and TLR9 agonist (empty triangle). The X-axis shows the days post-tumor inoculation, and the Y axis shows the tumor volume in $mm^3$.

Figure 8:
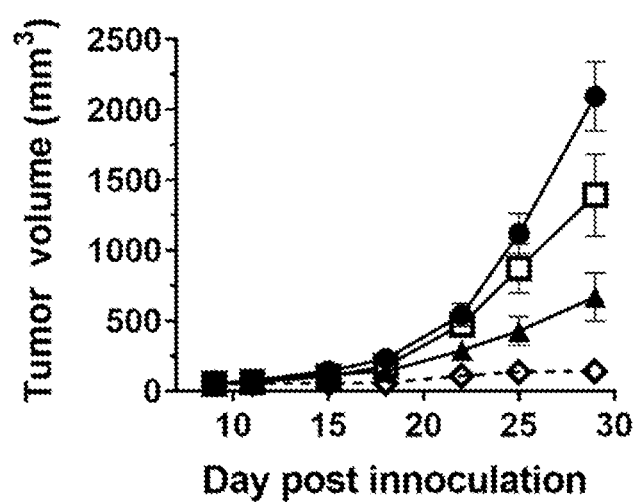

FIG. 8 depicts data from an experiment testing the antitumor efficacy of BsAb3 in combination with a CDK2/4/6 inhibitor in the B16F10 mouse tumor model. Mice harboring B16F10 tumors were treated with a control isotype antibody (solid circle), BsAb3 (solid triangle), a CDK2/4/6 inhibitor (empty square), or both BsAb3 and CDK2/4/6 inhibitor (empty diamond). The X-axis shows the days post-tumor inoculation, and the Y axis shows the tumor volume in $mm^3$.

DETAILED DESCRIPTION

Provided herein are antibodies that specifically bind to CD47, antibodies that specifically bind to PD-L1, and bispecific antibodies that specifically bind to CD47 and PD-L1. Further provided here are bispecific antibodies which share a common light chain. Also provided herein are related nucleic acids, compositions, and methods of making and using the antibodies.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995), as well as in subsequent editions and corresponding websites of the above references, as applicable.

The invention will now be described in detail by way of reference using the following definitions and examples. All patents and publications, including all sequences disclosed within such patents and publications, referred to herein are expressly incorporated by reference.

Definitions

Unless otherwise defined, all terms of art, notations and other scientific terms or terminology used herein are intended to have the meanings commonly understood by those of skill in the art to which this invention pertains. For example, the term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone). In some cases, terms with commonly understood meanings are defined herein for clarity and/or for ready reference, and the inclusion of such definitions herein should not necessarily be construed to represent a substantial difference over what is generally understood in the art.

As used herein, the singular forms "a", "an" and "the" include their corresponding plural references unless the context clearly dictates otherwise.

As used herein, the numeric ranges are inclusive of the numbers defining the range.

Reference to "about" a value or parameter herein includes (and describes) embodiments that are directed to that value or parameter per se, as well as to values or parameters that may be as much as 10% below or above the stated numerical value for that parameter. For example, as dose of "about 5 mg/kg" includes 5 mg/kg and also any value between 4.5 mg/kg and 5.5 mg/kg. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

As used herein, nucleic acids are written left to right in 5' to 3' direction; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The terms "polypeptide", "oligopeptide", "peptide" and "protein" are used interchangeably herein to refer to chains of amino acids of any length. For example, the chain may be relatively short (e.g., 10-100 amino acids), or longer. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition. The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "ABM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283: 1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, the term "Fc chain" refers to a C-terminal region of an antibody heavy chain and comprises two to three constant domains depending on the isotype. As used herein, an Fc chain may comprise native or variant Fc sequences. Unless otherwise specified herein, numbering of amino acid residues in the Fc chain or constant region is according to the EU numbering system, also called the EU index, as described in Kabat et al., Sequences of Proteins of Immunological Interest, 5th Ed. Public Health Service, National Institutes of Health, Bethesda, Md., 1991.

As used herein, the term "Fc domain" refers to the region of an antibody that comprises two Fc chains. For example, in standard IgG format, an antibody has two heavy chains, both of which have an Fc chain. Collectively, the two Fc chains are referred to herein as an "Fc domain".

A "wild-type Fc chain" comprises an amino acid sequence identical to the amino acid sequence of an Fc chain found in nature. By "wild-type" human IgG Fc it is meant a sequence of amino acids that occurs naturally within the human population. Of course, just as the Fc sequence may vary slightly between individuals, one or more alterations may be made to a wild-type sequence and still remain within the scope of the invention. A "variant Fc chain" comprises an amino acid sequence which differs from that of a wild-type Fc chain by virtue of at least one amino acid modification yet retains at least one effector function of the wild-type Fc chain. In some embodiments, the variant Fc chain has at least one amino acid substitution compared to a wild-type Fc chain e.g., from about one to about ten amino acid substitutions, and preferably, from about one to about five amino acid substitutions in a wild-type Fc chain. The variant Fc chain herein will preferably possess at least about 80% sequence identity with a wild-type Fc chain, and most preferably, at least about 90% sequence identity therewith, more preferably, at least about 95%, at least about 96%, at least about 97%, at least about 98%, at least about 99% sequence identity therewith. In some embodiments, an Fc chain comprises part or all of a wild-type hinge region (generally at its N-terminal). In some embodiments, an Fc polypeptide does not comprise a functional or wild-type hinge region.

The term "hinge region" as used herein includes the meaning known in the art, which is illustrated in, for example, Janeway et al., ImmunoBiology: the immune system in health and disease, Elsevier Science Ltd., NY (4th ed., 1999); Bloom et al., Protein Science, 6:407-415, 1997; and Humphreys et al., J. Immunol. Methods, 209:193-202, 1997.

As used herein, the terms "linked," "fused" and "fusion" are used interchangeably to refer to the joining together of two more elements or components, by whatever means including chemical conjugation or recombinant means.

As used herein, the term "covalently linked" means that the specified moieties are either directly covalently bonded to one another, or else are indirectly covalently joined to one another through an intervening moiety or moieties, such as a linking peptide or moiety.

As used herein, the terms "genetically fused" and "genetic fusion" refer to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence.

As used herein, the term "modification" refers to an amino acid substitution, insertion, and/or deletion in a polypeptide sequence, an alteration to a moiety chemically linked to a protein, or a modification of a function of a protein, e.g., an antibody. For example, a modification may be an altered function of an antibody, or an altered carbohydrate structure attached to a protein. As used herein, an "amino acid modification" refers to a mutation (substitution), insertion (addition), or deletion of one or more amino acid residue in an antibody. The term "amino acid mutation" denotes the substitution of at least one existing amino acid residue with another different amino acid residue (e.g. the replacing amino acid residue). The term "amino acid deletion" denotes the removal of at least one amino acid residue at a predetermined position in an amino acid sequence. For example, the mutation L234A denotes that the amino acid residue lysine at position 234 in an antibody Fc-region is substituted by the amino acid residue alanine (substitution of lysine with alanine), (numbering according to the EU index numbering system).

The term "agent" is used herein to denote a biological macromolecule, an extract made from biological materials, a mixture of biological macromolecules, a chemical compound, a mixture of chemical compounds, and/or a mixture of chemical compounds and biological macromolecules. The term "therapeutic agent" refers to an agent that has biological activity.

A "humanized" antibody refers to a chimeric antibody comprising amino acid residues from non-human hypervariable regions and amino acid residues from human framework regions. Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "monospecific antibody" refers to an antibody that comprises one or more antigen binding sites per molecule such that any and all binding sites of the antibody specifically recognize the identical epitope on the antigen. Thus, in cases where a monospecific antibody has more than one antigen binding site, the binding sites compete with each other for binding to one antigen molecule.

As used herein, a "bispecific antibody" is a molecule that has binding specificity for at least two different epitopes. In some embodiments, bispecific antibodies can bind simultaneously two different antigens. In other embodiments, the two different epitopes may reside on the same antigen.

A "target antigen," a "target cell antigen," a "tumor antigen," or a "tumor specific antigen," as used herein refers to an antigenic determinant presented on the surface of a target cell, for example a cell in a tumor such as a cancer cell or a cell of the tumor stroma.

As used herein, an "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

As used herein, the term "linker" refers to an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

As used herein, the term "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody. Cysteine residues can be introduced, e.g., by site directed mutagenesis, so that stabilizing disulfide bonds can be made within the molecule.

The term "compete", as used herein with regard to an antibody, means that a first antibody, or an antigen-binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein "antibody-dependent cell-mediated cytotoxicity" or "ADCC" refers to a cell-mediated reaction in which nonspecific cytotoxic cells that express Fc receptors (FcRs) (e.g., natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., PNAS (USA), 95:652-656, 1998.

As used herein, a "complement dependent cytotoxicity" or "CDC" refers to the lysing of a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., J. Immunol. Methods, 202: 163, 1996, may be performed.

As used herein, the terms "immunospecifically binds," "immunospecifically recognizes," "specifically binds," "specifically recognizes" and analogous terms refer to molecules e.g., binding domains that specifically bind to an antigen (e.g., epitope or immune complex) and do not specifically bind to another molecule. A molecule that specifically binds to an antigen may bind to other peptides or polypeptides with lower affinity as determined by assays known in the art e.g., immunoassays, BIACORE™ or other assays. Preferably, molecules that specifically bind an antigen do not cross-react with other proteins.

The term "epitope" refers to that portion of a molecule capable of being recognized by, making contact and/or being bound by an antibody at one or more of the antibody's antigen-binding regions known as a paratope. A single antigen may have more than one epitope. Thus, different antibodies may bind to different areas on an antigen and may have different biological effects. Epitopes often consist of a chemically active surface grouping of molecules such as amino acids or sugar side chains and have specific three-dimensional structural characteristics as well as specific charge characteristics. As used herein, epitopes may be either conformational or linear. A conformational epitope is produced by spatially juxtaposed amino acids from different segments of the linear polypeptide chain. A linear epitope is one produced by adjacent amino acid residues in a polypeptide chain. In certain embodiments, an epitope may include moieties of saccharides, phosphoryl groups, or sulfonyl groups on the antigen.

The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds. Once a desired epitope on an antigen is determined, it is possible to generate antibodies to that epitope, e.g., using the techniques described herein.

The terms "specific binding" or "specifically binding" when used in reference to the interaction of an antibody and a protein or peptide refers to an interaction that is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

In certain embodiments "specifically binds" means, for instance, that an antibody binds a protein with a $K_D$ of about 0.1 nM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human CD47 and mouse CD47). Likewise, because of homology within certain regions of polypeptide sequences of different proteins, specific binding can include an antibody that recognizes more than one protein. It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in some embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In certain alternative embodiments, an antibody may be multispecific and comprise at least two antigen-binding sites with differing specificities. By way of non-limiting example, a bispecific antibody may comprise one antigen-binding site that recognizes an epitope on one protein and further comprise a second, different antigen-binding site that recognizes a different epitope on a second protein. Generally, but not necessarily, reference to binding means specific binding.

An antibody that specifically binds to an antigen may bind to other peptides or polypeptides with lower affinity as determined by assays known in the art e.g. immunoassays, BIACORE™, or other assays. Preferably, the antibody that specifically binds an antigen does not cross-react with other proteins.

The terms "non-specific binding" or "background binding" when used in reference to the interaction of an antibody and a protein or peptide refers to an interaction that is not dependent on the presence of a particular structure (i.e., the antibody is binding to proteins in general rather that a particular structure such as an epitope).

The term "$k_{on}$" or "$k_a$", as used herein, refers to the rate constant for association of an antibody to an antigen.

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Determinations of the association and dissociation rate constants, $k_{on}$ and $k_{off}$ respectively, to determine $K_D$ and other ratios, may be made, for example, using a surface plasmon resonance-based biosensor to characterize an analyte/ligand interaction under conditions where the analyte is monovalent with respect to binding a ligand that is immobilized at low capacity onto a sensor surface via a capture reagent. The analysis may be performed, for example, using a kinetic titration methodology as described in Karlsson et al., Anal. Biochem 349, 136-147, 2006, or using a multicycle kinetics analysis. The sensor chip, capturing reagent, and assay buffer employed for a given assay are chosen to give stable capture of ligand onto the sensor surface, minimize non-specific binding of the analyte to the surfaces, and yield analyte-binding responses that are appropriate for kinetic analysis, per the recommendations in Myszka, J. Mol. Recognit 12, 279-284, 1999. The analyte-binding responses per analyte/ligand interaction are double referenced and fit to a 1:1 Langmuir "mass transport limited model" with $k_a$, $k_d$ and $R_{max}$ as global parameters as described in Myszka & Morton et al., *Biophys. Chem* 64, 127-137 (1997). The equilibrium dissociation constant, $K_D$, is deduced from the ratio of the kinetic rate constants, $K_D = k_{off}/k_{on}$. Such determinations preferably take place at 25° C. or 37° C. Typically, the rate constants ($k_{on}/k_a$ and $k_{off}/k_d$) and equilibrium dissociation constants are measured using whole antibody and monomeric (e.g. CD47 protein or PD-L1 protein).

As used herein, the term "binding affinity," generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. In particular, the term "binding affinity" is intended to refer to the dissociation rate of a particular antigen-antibody interaction. The $K_D$ is the ratio of the rate of dissociation, also called the "off-rate ($k_{off}$)," to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. $K_D$ values for antibodies can be determined using methods well established in the art. One method for determining the $K_D$ of an antibody is by using surface plasmon resonance (SPR), typically using a biosensor system such as BIACORE system. BIACORE kinetic analysis comprises analyzing the binding and dissociation of an antigen from chips with immobilized molecules (e.g., molecules comprising epitope binding domains), on their surface. Another method for determining the $K_D$ of an antibody is by using Bio-Layer Interferometry, typically using OCTET® technology (Octet QK$^e$ system, ForteBio).

"Biologically active," "biological activity" and "biological characteristics" with respect to a bispecific antibody of the present invention, such as an antibody, fragment, or derivative thereof, means having the ability to bind to a biological molecule, except where specified otherwise.

As used herein, the terms, "polynucleotides", "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or polypeptide that is separated from some or all of the coexisting materials in the natural system is isolated. Such polynucleotide could be part of a vector and/or such polynucleotide or polypeptide could be part of a composition, e.g., a mixture, solution or suspension or comprising an isolated cell or a cultured cell which comprises the polynucleotide or polypeptide, and still be isolated in that the vector or composition is not part of its natural environment. Any molecule provided herein may be isolated.

As used herein, the term "operably linked" refers to a situation wherein the components described are in a relationship permitting them to function in their intended manner. For example, a control sequence "operably linked" to a coding sequence is ligated in such a manner that expression of the coding sequence is achieved under conditions suitable or compatible with the control sequence. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, the term "expression control sequence" or "control sequence" refers to a polynucleotide sequence that is necessary to effect the expression of a coding sequence to which it is ligated. The nature of such control sequences differs depending upon the host organism. For example, in prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "mammalian cells" include reference to cells derived from mammals including humans, rats, mice, hamsters, guinea pigs, chimpanzees, or macaques. The cells may be cultured in vivo or in vitro.

As used herein, the term "purified product" refers to a preparation of the product which has been isolated from the cellular constituents with which the product is normally associated and/or from other types of cells that may be present in the sample of interest.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

As used herein, the term "cancer" or "cancerous" refers to or describes a physiological condition in mammals that is typically characterized by unregulated cell growth, a neoplasm or a tumor resulting from abnormal uncontrolled growth of cells. In some aspects, cancer refers to a malignant primary tumor without metastasis, which has remained localized. In other aspects, cancer refers to a malignant tumor, which has invaded and destroyed neighboring body structures and spread to distant sites. In some aspects, the cancer is associated with a specific cancer antigen.

As used herein, the term "malignant cell", or "malignancy" refers to tumors or tumor cells that are invasive and/or able to undergo metastasis, i.e., a cancerous cell.

As used herein, the term "treat," "treating" or "treatment" is an approach for obtaining beneficial or desired clinical results. For the purpose of the present invention, treatment is defined as the administration of an anti-CD47, anti-PD-L1, or anti-CD47/anti-PD-L1 antibody molecule (e.g., CD47 monoclonal antibody, PD-L1 monoclonal antibody, or CD47/PD-L1 bispecific antibody) to a subject, e.g., a patient. Such administration can be e.g., by direct administration to the subject or by application to an isolated tissue or cell from a subject which is returned to the subject. The anti-CD47, anti-PD-L1, or CD47/PD-L1 antibody molecule can be administered alone or in combination with one or more agents. The treatment can be to cure, heal, alleviate, relieve, alter, remedy, ameliorate, palliate, improve or affect the disorder, the symptoms of the disorder or the predisposition toward the disorder, e.g., a cancer.

As used herein, the term "subject" is intended to include any animal (e.g., a mammal), including, but not limited to, humans, non-human primates, rodents, and the like, which is to be the recipient of a particular treatment. For example, a subject can be a patient (e.g., a human patient or a veterinary patient), having a cancer. Typically, the terms "subject," "individual" and "patient" are used interchangeably herein in reference to a human subject.

The term "non-human animals" of the invention includes all non-human vertebrates, e.g., non-human mammals and non-mammals, such as non-human primates, sheep, dog, cow, chickens, amphibians, reptiles, mouse, rat, rabbit or goat etc., unless otherwise noted.

As used herein, the term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

As used herein, the terms "pharmaceutically acceptable excipient, carrier or adjuvant" or "acceptable pharmaceutical carrier" refer to an excipient, carrier or adjuvant that can be administered to a subject, together with at least one antibody of the present disclosure, and which does not destroy the activity of the antibody. The excipient, carrier or adjuvant should be nontoxic when administered with an antibody in doses sufficient to deliver a therapeutic effect.

As used herein, the term "ameliorating" means a lessening or improvement of one or more symptoms as compared to not administering an antibody molecule of the invention. "Ameliorating" also includes shortening or reduction in duration of a symptom.

As used herein, the terms "prevent", "preventing" and "prevention" refer to the prevention of the recurrence or onset of one or more symptoms of a disorder in a subject as result of the administration of a prophylactic or therapeutic agent.

As used herein, an "effective amount," "therapeutically effective amount," "therapeutically sufficient amount," or "effective dosage" refers to any amount of a therapeutic agent which is effective or sufficient, upon single or multiple dose administration to a subject, in preventing, healing, ameliorating, treating or managing a disease, disorder or side effect, or decreasing the rate of advancement of a disease or disorder, or in prolonging curing, alleviating, relieving, or improving the condition of a subject with a disorder as described herein beyond that expected in the absence of such treatment. The term also includes within its scope amounts effective to enhance normal physiological function. An effective amount may be considered in the context of administering one or more therapeutic agents, and a single agent may be considered to be given in an effective amount if, in conjunction with one or more other agents, a desirable result may be or is achieved.

As used herein, "inhibiting the growth" of the tumor or cancer refers to slowing, interrupting, arresting or stopping its growth and/or metastases and does not necessarily indicate a total elimination of the tumor growth.

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. As used herein, the term "half maximal effective concentration ($EC_{50}$)" refers to the concentration of a therapeutic agent which causes a response halfway between the baseline and maximum after a specified exposure time. The therapeutic agent may cause inhibition or stimulation. The $EC_{50}$ value is commonly used, and is used herein, as a measure of potency.

As used herein, "combination therapy" or administration "in combination with" refers to the use of more than one prophylactic and/or therapeutic agent. The use of the term "combination therapy" or "in combination" does not restrict the order in which prophylactic and/or therapeutic agents are administered to a subject with a disorder. In other words, the combination therapy may be done by separately, sequentially, or simultaneously treating with the therapeutic agents. In the case of "sequential administration," the first administered agent may be exerting some physiological effect on the subject when the second agent is administered or becomes active in the subject.

The term "simultaneous administration" as used herein in relation to the administration of prophylactic and/or therapeutic agent refers to the administration of agents such that the individual agents are present within a subject at the same time. Simultaneous administration may be affected by the molecules being formulated in a single composition, or in separate compositions administered at the same or similar time. Sequential administration may be in any order as required.

As used herein, "CD47" refers to mammalian Cluster of Differentiation 47 (CD47) protein, preferably human CD47 protein. The amino acid sequence and related information for human CD47 is provided, for example, under UniProtKB number A0A0A1TSG4, which is hereby incorporated by reference for all purposes.

Typically, a naturally occurring allelic variant of CD47 has an amino acid sequence at least 95%, 97% or 99% identical to the protein described in UniProtKB number A0A0A1TSG4. The CD47 protein is characterized as a transmembrane protein that belongs to the immunoglobulin superfamily, and which interacts with various ligands such as signal-regulatory protein alpha (SIRPα), thrombospondin-1 (TSP-1), and membrane integrins. CD47 is overexpressed by various types of cancer cell. The CD47 ligand SIRPα is expressed on various cells of the innate immune system, such as macrophages and dendritic cells (DCs). Binding of CD47 to SIRPα suppresses the activity of the immune cells that express SIRPα, and thereby enables tumor cells to escape the innate immune system surveillance As used herein, an "antibody that binds to CD47" an "antibody that recognizes CD47" an "anti-CD47 antibody," an "anti-CD47 antibody molecule", an "antibody that specifically binds CD47", a "CD47 antibody", or the like comprises a molecule that contains at least one binding domain that specifically binds to CD47. The CD47 antibody molecules of the present invention includes antibodies thereof that interact with or recognize, e.g., bind (e.g., bind specifically) to CD47, e.g., human CD47, mouse CD47, rat CD47, cynomolgus CD47.

As used herein, "PD-L1" refers to mammalian Programmed death-ligand 1 (PD-L1) protein, preferably human PD-L1 protein. PD-L1 is also known as CD274 or B7-H1. The amino acid sequence and related information for human PD-L1 is provided, for example, under UniProtKB number Q9NZQ7, which is hereby incorporated by reference for all purposes.

Typically, a naturally occurring allelic variant of PD-L1 has an amino acid sequence at least 95%, 97% or 99% identical to the protein described in UniProtKB number Q9NZQ7. The PD-L1 protein is characterized as a transmembrane protein that is involved in suppressing the adaptive arm of the immune system, e.g. by binding to PD-1. PD-L1 is overexpressed by various types of cancer cell. The PD-L1 is a ligand for the receptor PD-1, which is expressed cells of the adaptive immune system, such as T cells. Binding of PD-L1 to PD-1 suppresses the activity of the immune cells that express PD-1, and thereby enables tumor cells to escape PD-1 expressing immune cells (e.g. effector T cells).

As used herein, an "antibody that binds to PD-L1" an "antibody that recognizes PD-L1" an "anti-PD-L1 antibody," an "anti-PD-L1 antibody molecule", an "antibody that specifically binds PD-L1", a "PD-L1 antibody", or the like comprises a molecule that contains at least one binding domain that specifically binds to PD-L1. The PD-L1 antibody molecules of the present invention includes antibodies thereof that interact with or recognize, e.g., bind (e.g., bind specifically) to PD-L1, e.g., human PD-L1, mouse PD-L1, rat PD-L1, cynomolgus PD-L1.

As used herein, the term "CD47/PD-L1 bispecific antibody" refers to a molecule designed to specifically bind to CD47 and PD-L1.

As used herein, the "first polypeptide" is any polypeptide which is to be associated with a second polypeptide. The first polypeptide and second polypeptide meet at an interface. In addition to the interface, the first polypeptide may comprise one or more additional domains, such as "binding domains" (e.g., an antibody variable domain, receptor binding domain, ligand binding domain or enzymatic domain) or antibody constant domains (or parts thereof) including CH2, CH1 and CL domains. Normally, the first polypeptide will comprise at least one domain which is derived from an antibody. This domain conveniently is a constant domain, such as the CH3 domain of an antibody and can form the interface of the first polypeptide. Exemplary first polypeptides include antibody heavy chain polypeptides, chimeras combining an antibody constant domain with a binding domain of a heterologous polypeptide, receptor polypeptides, ligand polypeptides, and antibody variable domain polypeptides (e.g., bispecific antibodies).

In addition to the interface, the second polypeptide may comprise additional domains such as a "binding domain" (e.g., an antibody variable domain, receptor binding domain, ligand binding domain or enzymatic domain), or antibody constant domains (or parts thereof) including CH2, CH1 and CL domains. Normally, the second polypeptide will comprise at least one domain which is derived from an antibody. This domain conveniently is a constant region, such as the CH3 domain of an antibody and can form the interface of the second polypeptide. Exemplary second polypeptides include antibody heavy chain polypeptides, chimeras combining an antibody constant domain with a binding domain of a heterologous polypeptide, and antibody variable domain polypeptides (e.g., bispecific antibodies).

As used herein, the term "complex" or "complexed" refers to the association of two or more molecules that interact with each other through bonds and/or forces (e.g., van der waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

Although any materials and methods similar or equivalent to those described herein can be used in the practice or testing or testing of the present invention, the preferred materials and methods are now described.

Materials and Methods

Various techniques for the production of antibodies have been described which include the traditional hybridoma method for making monoclonal antibodies, recombinant techniques for making antibodies (including chimeric antibodies, e.g., humanized antibodies), antibody production in transgenic animals and the recently described phage display technology for preparing "fully human" antibodies.

Provided herein are methods of making any of the antibodies provided herein. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

Any suitable method for preparing bispecific antibodies may be used to prepare bispecific antibodies provided herein (e.g. depending on the choice of antibody features and components).

According to one approach to making bispecific antibodies, antibody variable domains with the desired binding specificities are fused to immunoglobulin constant region sequences. The fusion preferably is with an immunoglobulin heavy chain constant region, comprising at least part of the hinge, CH2 and CH3 regions. In some embodiments, the first heavy chain constant region (CH1), containing the site for light chain binding can be present in at least one of the fusions. In some embodiments, polynucleotides encoding the immunoglobulin heavy chain fusions and, if desired, the immunoglobulin light chain, may be inserted into separate expression vectors, and may be cotransfected into a suitable host organism. In other embodiments the coding sequences for two or all three polypeptide chains may be inserted into one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted amino acid in the first hinge region has an opposite charge to the corresponding amino acid in the second hinge region in another arm. This approach is described in International Patent Application No. PCT/US2011/036419 (WO2011/143545).

In another approach, the formation of a desired heteromultimeric or heterodimeric protein (e.g., bispecific antibody) is enhanced by altering or engineering an interface between a first and a second Fc chain. In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545). In some embodiments, one Fc chain of a bispecific antibody can comprise amino acid modifications at positions 223 and 228 (e.g., (C223E or C223R), and (P228E or P228R)) in the hinge region and at position 409 (e.g., K409R (EU numbering scheme)) in the CH3 region of human IgG2, and the other Fc chain of the bispecific antibody can comprise amino acid modifications at positions 223, 225 and 228 (e.g., (C223E or C223R), (E225R), and (P228E or P228R)) in the hinge region and at position 368 (e.g., L368E (EU numbering scheme)) in the CH3 region of human IgG2. In other embodiments, one Fc chain of a bispecific antibody can comprise amino acid modifications at positions 223 and 228 (e.g., (C223E or C223R) and (P228E or P228R)) in the hinge region and at position 368 (e.g., L368E (EU numbering scheme)) in the CH3 region of human IgG2, and the other Fc chain of the bispecific antibody can comprise amino acid modifications at positions 223, 225 and 228 (e.g., (C223E or C223R), (E225R), and (P228E or P228R)) in the hinge region and at position 409 (e.g., K409R (EU numbering scheme)) in the CH3 region of human IgG2. In some embodiments, a bispecific antibody can comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1. In some embodiments, a bispecific antibody can comprise amino acid modifications at positions 228 (e.g., (P228E or P228R)) in the hinge region and at position 409 or 368 (e.g., R409 or L368E (EU numbering scheme)) in the CH3 region of human IgG4.

In some embodiments, a bispecific antibody may have knob-in-hole mutations in the Fc chains. For example, in some embodiments, in a bispecific antibody having knob-in-hole mutations, the first Fc chain of the antibody Fc domain has one or more mutations to form a "knob", and the second Fc chain of the antibody Fc domain has one or more mutations to form a "hole" (or vice-versa). Exemplary knob-in-hole engineering of antibodies is described in U.S. Pat. No. 5,731,168, PCT Publication No. WO2009089004, U.S. Publication No. 20090182127, Marvin and Zhu, Acta Pharmacologica Sincia (2005) 26(6):649-658 and Kontermann (2005) Acta Pharacol. Sin., 26:1-9.

A "knob" refers to at least one amino acid side chain which projects from the interface of a first polypeptide (e.g. first Fc chain) and is therefore positionable in a compensatory hole in an adjacent second polypeptide (e.g. second Fc chain) so as to stabilize a heterodimer, and thereby favor heterodimer formation over homodimer formation. The knob may exist in the original interface or may be introduced synthetically (e.g., by altering a nucleic acid encoding the interface). Normally, nucleic acid encoding the interface of the first polypeptide is altered to encode the knob. To achieve this, the nucleic acid encoding at least one original amino acid residue in the first polypeptide is replaced with nucleic acid encoding at least one "import" amino acid residue which has a larger side chain volume than the original amino acid residue. Certain import residues for the formation of a knob are generally naturally occurring amino acid residues and are preferably selected from arginine (R), phenylalanine (F), tyrosine (Y) and tryptophan (W).

A "hole" refers to at least one amino acid side chain which is recessed from the interface of a second polypeptide (e.g. second Fc chain) and therefore accommodates a corresponding knob in an adjacent first polypeptide (e.g. first Fc chain). The hole may exist in the original interface or may be introduced synthetically (e.g., by altering a nucleic acid encoding the interface). Normally, nucleic acid encoding the interface of the second polypeptide is altered to encode the hole. To achieve this, the nucleic acid encoding at least one original amino acid residue of the second polypeptide is replaced with DNA encoding at least one "import" amino acid residue which has a smaller side chain volume than the original amino acid residue. Certain import residues for the formation of a hole are usually naturally occurring amino acid residues and are preferably selected from alanine (A), serine (S), threonine (T) and valine (V).

The term "interface," as used herein typically refers to any amino acid residue present in the domain that can be involved in first polypeptide and second polypeptide contacts. An "original amino acid" residue is one which is replaced by an "import amino acid" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991).

In some embodiments, a bispecific antibody may have any of the features or characteristics of any of the bispecific antibodies provided in WO2016166629.

An optional bispecific antibody format is an Fv-derived strategy based on a covalently linked, bispecific heterodimeric diabody structure, also known as dual-affinity re-targeting (DART®) proteins, which is described in for example in U.S. Pat. Publication Nos. 2007/0004909, 2009/0060910, and 2010/0174053.

Once a nucleic acid sequence encoding molecules of the invention (i.e., binding domains) has been obtained, the vector for the production of the molecules may be produced by recombinant DNA technology using techniques well known in the art.

The polynucleotides encoding the antibody (e.g., anti-CD47 antibody, anti-PD-L1 antibody, or CD47/PD-L1 bispecific antibody) binding domains of the present invention may include an expression control polynucleotide sequence operably linked to the antibody coding sequences, including naturally-associated or heterologous promoter regions known in the art. The expression control sequences may be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the antibodies. Eukaryotic cell lines include the CHO cell lines, various COS cell lines, HeLa cells, myeloma cell lines, transformed B-cells, or human embryonic kidney cell lines.

In one embodiment, the DNA encoding the antibodies of the invention is isolated and sequenced using conventional procedures (e.g., by using oligonucleotide probes that are capable of binding specifically to genes encoding the heavy and light chains of antibodies). Once isolated, the DNA may be placed into expression vectors, which are then transfected into host cells such as simian COS cells, CHO cells, or myeloma cells that do not otherwise produce immunoglobulin protein, to obtain the synthesis of monoclonal antibodies in the recombinant host cells. The DNA also may be modified, for example, to improve one or more properties of the corresponding antibody (e.g. binding affinity, immunogenicity, etc.).

Anti-CD47 Antibodies

In some embodiments, provided herein are anti-CD47 antibodies.

In one aspect, provided is an anti-CD47 antibody comprising (a) a heavy chain variable region (VH) comprising a VH complementarity determining region one (VH CDR1), a VH complementarity determining region two (VH CDR2), and a VH complementarity determining region three (VH CDR3) of the VH sequence shown in SEQ ID NO: 1, 3, 7, 8, or 9; and/or (b) a light chain variable region (VL) comprising a VL complementarity determining region one (VL CDR1), a VL complementarity determining region two (VL CDR2), and a VL complementarity determining region three (VL CDR3) of the VL sequence shown in SEQ ID NO: 2 or 6.

In another aspect, provided is an anti-CD47 antibody having any one of a VH and/or any one of a VL sequence as listed in Table 1. In Table 1, the underlined sequences are CDR sequences according to Kabat and in bold according to Chothia. In one embodiment, the invention provides an antibody comprising a VH and/or a VL, wherein: (a) the VH comprises SEQ ID NO: 1, 3, 7, 8, or 9; and/or (b) the VL comprises SEQ ID NO: 2 or 6.

TABLE 1

Exemplary anti-CD47 VH and VL sequences

| Description | Sequence |
|---|---|
| CD47_<br>P01A11_75<br>VH | QVQLVQSGAEVKKPGSSVKVSCKASGYTFSSYAISWWRQAPGQ<br>GLEWMGGISPIFGTANYAQKFQGRVTITADESTSTAYMELSSLRS<br>EDTAVYYCARDAGRSSDVGWYVGAIDVWGQGTLVTVSS (SEQ<br>ID NO: 1) |
| CD47_<br>P01A11_497<br>VH | QVQLVQSGAEVKKPGSSVKVSCKASGGTFTSYAISWVRQAPGQ<br>GLEWMGGISPIFGTANYAQKFQGRVTITADESTSTAYMELSSLRS<br>EDTAVYYCARDAGRSSDVGWYVGALDVWGQGTLVTVSS (SEQ<br>ID NO: 3) |
| CD47_<br>P01A11_parent<br>VH | QVQLVQSGAEVKKPGSSVKVSCKASGYTFTNYAISWRQAPGQ<br>GLEWMGGISPLFGTANYAQKFQGRVTITADESTSTAYMELSSLR<br>SEDTAVYYCARDGGRSSDVGWYVGAMDVWGQGTLVTVSS<br>(SEQ ID NO: 7) |
| CD47_<br>P14D04_parent<br>VH | EVQLLESGGGLVQPGGSLRLSCAASGFSFSTFTMNWVRQAPGK<br>GLEWVSTISGTGGNTYYADSVKGRFTISRDNSKNTLYLQMNSLR<br>AEDTAVYYCARRRSTVGSNGHSYWFDYWGQGTLVTVSS (SEQ<br>ID NO: 8) |

TABLE 1-continued

Exemplary anti-CD47 VH and VL sequences

| Description | Sequence |
| --- | --- |
| CD47_<br>P01A08_parent<br>VH | QVQLVQSGAEVKKPGSSVKVSCKASGYTFSNYAITWVRQAPGQ<br>GLEWMGGISPIFGTANYAQKFQGRVTITADESTSTAYMELSSLRS<br>EDTAVYYCARDGGRSSDGGWRGAGMDYWGQGTLVTVSS<br>(SEQ ID NO: 9) |
| Common light<br>chain 1 VL | QSVLTQPPSASGTPGQRVTISCSGSSSNIGSNYVYWYQQLPGTA<br>PKLLIYRNNQRPSGVPDRFSGSKSGTSASLAISGLRSEDEADYY<br>CAAWDDSLSGVVFGGGTKLTVL (SEQ ID NO: 2) |
| Common light<br>chain 2 VL | DIQMTQSPSSLSASVGDRVTITCRASQSISSYLNWYQQKPGKAP<br>KLLIYAASSLQSGVPSRFSGSGSGTDFTLTISSLQPEDFATYYCQ<br>QSYSTPLTFGQGTKVEIK (SEQ ID NO: 6) |

In some embodiments, an anti-CD47 antibody provided herein comprises a VH and a VL, wherein the VH comprises the sequence of SEQ ID NO: 1 and the VL comprises the sequence of SEQ ID NO: 2. In an embodiment, an anti-CD47 antibody provided herein comprises a VH and a VL, wherein the VH comprises the sequence of SEQ ID NO: 3 and the VL comprises the sequence of SEQ ID NO: 2. In an embodiment, an anti-CD47 antibody provided herein comprises a VH and a VL, wherein the VH comprises the sequence of SEQ ID NO: 7 and the VL comprises the sequence of SEQ ID NO: 2. In an embodiment, an anti-CD47 antibody provided herein comprises a VH and a VL, wherein the VH comprises the sequence of SEQ ID NO: 9 and the VL comprises the sequence of SEQ ID NO: 2. In an embodiment, an anti-CD47 antibody provided herein comprises a VH and a VL, wherein the VH comprises the sequence of SEQ ID NO: 8 and the VL comprises the sequence of SEQ ID NO: 6.

In some embodiments, an anti-CD47 antibody provided herein has a VL amino acid sequence that is the same as in multiple different antibodies having different binding specificities. Thus, for various antibodies provided herein, antibodies may have different VH sequences, but the same VL sequence. Although these antibodies have same VL sequence, because they have different VH sequences, they have different binding affinity and/or specificity from each other. In some embodiments, antibodies provided herein that share the same VL sequence specifically bind to different antigens. For example, provided herein are anti-CD47 and anti-PD-L1 antibodies that have VLs that share the same amino acid sequence. VL sequences provided herein that are shared by more than one antibody are referred to herein as a "common light chain". Table 1 provides the sequence information for various common light chains that are part of antibodies provided herein. For example, the "Common Light Chain 1" VL is shared by the following different anti-CD47 and anti-PD-L1 antibodies: CD47_P01A11_75; CD47_P01A11_497; CD47_P01A11_parent; CD47_P01A08_parent; PDL1_P06B05_245; PDL1_P06B05_parent; PDL1_P06A09_parent. In another example, the "Common Light Chain 2" VL is shared by the following different anti-CD47 and anti-PD-L1 antibodies: CD47_P14D04_parent; PDL1_D04D09_parent VL.

The invention also provides CDR portions of antibodies to CD47.

In one aspect, provided is an anti-CD47 antibody having any one of the VH CDR sequences and/or any one of the VL CDR sequences as listed in Table 2. In one aspect, the invention provides an antibody which specifically binds to CD47, wherein the antibody comprises: (a) a VH comprising (i) a VH CDR1 comprising SEQ ID NO: 13, 14, 15, 22, 23, 25, 26, 27, 31, 32, 33, 37, 38, or 39; (ii) a VH CDR2 comprising SEQ ID NO: 16, 17, 28, 29, 34, or 35; and (iii) a VH CDR3 comprising SEQ ID NO: 18, 24, 30, 36, or 40; and/or (b) a VL comprising (i) a VL CDR1 comprising SEQ ID NO: 19 or 53; (ii) a VL CDR2 comprising SEQ ID NO: 20 or 54; and (iii) a VL CDR3 comprising SEQ ID NO: 21 or 55.

TABLE 2

Exemplary Anti-CD47 CDR sequences

VH CDRs

| mAb | VH CDR1 | VH CDR2 | VH CDR3 |
| --- | --- | --- | --- |
| CD47_<br>P01A11_<br>75 VH | GYTFSSY (SEQ ID NO: 13) (Chothia)<br>SYAIS (SEQ ID NO: 14) (Kabat)<br>GYTFSSYAIS (SEQ ID NO: 15) (Extended) | SPIFGT (SEQ ID NO: 16) (Chothia)<br>GISPIFGTANYAQKF QG (SEQ ID NO: 17) (Kabat) | DAGRSSDVGWYVGA IDV (SEQ ID NO: 18) (Chothia/Kabat) |
| CD47_<br>P01A11_<br>497 VH | GGTFTSY (SEQ ID NO: 22) (Chothia)<br>SYAIS (SEQ ID NO: 14) (Kabat)<br>GGTFTSYAIS (SEQ ID NO: 23) (Extended) | SPIFGT (SEQ ID NO: 16) (Chothia)<br>GISPIFGTANYAQKF QG (SEQ ID NO: 17) (Kabat) | DAGRSSDVGWYVGA LDV (SEQ ID NO: 24) (Chothia/Kabat) |

TABLE 2-continued

Exemplary Anti-CD47 CDR sequences

| | | | |
|---|---|---|---|
| CD47_<br>P01A11_<br>parent VH | GYTFTNY (SEQ ID<br>NO: 25) (Chothia)<br>NYAIS (SEQ ID NO:<br>26) (Kabat)<br>GYTFTNYAIS (SEQ<br>ID NO: 27)<br>(Extended) | SPLFGT (SEQ ID<br>NO: 28) (Chothia)<br>GISPLFGTANYAQKF<br>QG (SEQ ID NO: 29)<br>(Kabat) | DGGRSSDVGWYVGA<br>MDV (SEQ ID NO: 30)<br>(Chothia/Kabat) |
| CD47_<br>P14D04_<br>parent VH | GFSFSTF (SEQ ID<br>NO: 31) (Chothia)<br>TFTMN (SEQ ID NO:<br>32) (Kabat)<br>GFSFSTFTMN (SEQ<br>ID NO: 33)<br>(Extended) | SGTGGN (SEQ ID<br>NO: 34) (Chothia)<br>TISGTGGNTYYADSV<br>KG (SEQ ID NO: 35)<br>(Kabat) | RRSTVGSNGHSYWF<br>DY (SEQ ID NO: 36)<br>(Chothia/Kabat) |
| CD47_<br>P01A08_<br>parent VH | GYTFSNY (SEQ ID<br>NO: 37) (Chothia)<br>NYAIT (SEQ ID NO:<br>38) (Kabat)<br>GYTFSNYAIT (SEQ<br>ID NO: 39)<br>(Extended) | SPIFGT(SEQ ID NO:<br>16) (Chothia)<br>GISPIFGTANYAQKF<br>QG (SEQ ID NO: 17)<br>(Kabat) | DGGRSSDGGWRGA<br>GMDY (SEQ ID NO:<br>40) (Chothia/Kabat) |

VLCDRs

| mAb | VLCDR1 | VL CDR2 | VL CDR3 |
|---|---|---|---|
| Common<br>Light Chain<br>1 VL | SGSSSNIGSNYVY<br>(SEQ ID NO: 19)<br>(Chothia/Kabat) | RNNQRPS (SEQ ID<br>NO: 20) (Chothia/<br>Kabat) | AAWDDSLSGW<br>(SEQ ID NO: 21)<br>(Chothia/Kabat) |
| Common<br>Light Chain<br>2 VL | RASQSISSYLN<br>(SEQ ID NO: 53)<br>(Chothia/Kabat) | AASSLQS (SEQ ID<br>NO: 54) (Chothia/<br>Kabat) | QQSYSTPLT (SEQ ID<br>NO: 55) (Chothia/<br>Kabat) |

In some embodiments, provided herein is an anti-CD47 antibody, wherein the VH comprises the sequence of SEQ ID NO: 1, 3, 7, 8, or 9, or a variant thereof with 1, 2, 3, 4, 5, 6, 7, 8, 9, or 10 amino acid substitutions in the sequence; and/or wherein the VL comprises the sequence of SEQ ID NO: 2 or 6, or a variant thereof with 1, 2, 3, 4, 5, 6, 7, 8, 9, or 10 amino acid substitutions in the sequence. Optionally the substitutions are conservative amino acid substitutions. Optionally, the substitutions are not in a CDR region.

The invention also encompasses scFv of anti-CD47 antibodies provided herein. Single chain variable region fragments are made by, for example without limitation, genetically fusing light and/or heavy chain variable regions by using a short linking peptide (Bird et al., Science 242:423-426, 1988). Other forms of single chain antibodies, such as diabodies or minibodies are also encompassed.

In some embodiments, an anti-CD47 antibody provided herein is a monoclonal antibody. Optionally, the anti-CD47 antibody is a human antibody or a humanized antibody.

Anti-PD-L1 Antibodies

In some embodiments, provided herein are anti-PD-L1 antibodies.

In one aspect, provided is an anti-PD-L1 antibody comprising (a) VH comprising a VH CDR1, a VH CDR2, and a VH CDR3 of the VH sequence shown in SEQ ID NO: 4, 5, 10, 11, or 12; and/or (b) a VL comprising a VL CDR1, a VL CDR2, and a VL CDR3 of the VL sequence shown in SEQ ID NO: 2 or 6.

In another aspect, provided is an anti-PD-L1 antibody having any one of a VH and/or any one of a VL sequence as listed in Table 3. In Table 3, the underlined sequences are CDR sequences according to Kabat and in bold according to Chothia. In one embodiment, the invention provides an antibody comprising a VH and/or a VL, wherein: (a) the VH comprises SEQ ID NO: 4, 5, 10, 11, or 12; and/or (b) the VL comprises SEQ ID NO: 2 or 6.

In some embodiments, an anti-PD-L1 antibody provided herein comprises a VH and a VL, wherein the VH comprises the amino acid sequence of SEQ ID NO: 4 and the VL comprises the amino acid sequence of SEQ ID NO: 2. In an embodiment, an anti-PD-L1 antibody provided herein comprises a VH and a VL, wherein the VH comprises the amino acid sequence of SEQ ID NO: 5 and the VL comprises the amino acid sequence of SEQ ID NO: 6. In an embodiment, an anti-PD-L1 antibody provided herein comprises a VH and a VL, wherein the VH comprises the amino acid sequence of SEQ ID NO: 10 and the VL comprises the amino acid sequence of SEQ ID NO: 6. In an embodiment, an anti-PD-L1 antibody provided herein comprises a VH and a VL, wherein the VH comprises the amino acid sequence of SEQ ID NO: 11 and the VL comprises the amino acid sequence of SEQ ID NO: 2. In an embodiment, an anti-PD-L1 antibody provided herein comprises a VH and a VL, wherein the VH comprises the amino acid sequence of SEQ ID NO: 12 and the VL comprises the amino acid sequence of SEQ ID NO: 2.

TABLE 3

Exemplary Anti-PD-L1 VH and VL sequences

| Description | Sequence |
| --- | --- |
| PDL1_P06B05_245 VH | EVQLVESGGGLVKPGGSLRLSCAASGFTFSNAWMNWRQAPGKGLEVWGRIKTKADGGTTDYAAPVKGRFTISRDDSKNTLYLQMNSLKTEDTAVYYCTTDPGEYWDSVYGGMDYWGQGTLVTVSS (SEQ ID NO: 4) |
| PDL1_P04D09_113 VH | EVQLLESGGGLVQPGGSLRLSCAASGFTFSSYAMSWVRQAPGKGLEWVSAIGVRGGITYYADSVKGRFTISRDNSKNTLYLQMNSLRAEDTAVYYCARERSVGELVGIDQMDHWGQGTLVTVSS (SEQ ID NO: 5) |
| PDL1_P04D09_parent VH | EVQLLESGGGLVQPGGSLRLSCAASGFTFSSYAMSWVRQAPGKGLEWVSAIGVRGGITYYADSVKGRFTISRDNSKNTLYLQMNSLRAEDTAVYYCARERSVGELVGIDWMDHWGQGTLVTVSS (SEQ ID NO: 10) |
| PDL1_P06B05_parent VH | EVQLVESGGGLVKPGGSLRLSCAASGFTFSNAWMNVWRQAPGKGLEWVGRIKTKADGGTTDYAAPVKGRFTISRDDSKNTLYLQMNSLKTEDTAVYYCTTDPGSYWDSVYGGMDYWGQGTLVTVSSE (SQ ID NO: 11) |
| PDL1_P06A09_parent VH | EVQLVESGGGLVKPGGSLRLSCAASGFTFSNAWMNVWRQAPGKGLEWVGRIKSESDGGTTDYAAPVKGRFTISRDDSKNTLYLQMNSLKTEDTAVYYCTTDYRIDDWGYPYPGMDYWGQGTLVTVSS (SEQ ID NO: 12) |
| Common Light Chain 1 VL | QSVLTQPPSASGTPGQRVTISCSGSSSNIGSNYVYWYQQLPGTAPKLLIYRNNQRPSGVPDRFSGSKSGTSASLAISGLRSEDEADYYCAAWDDSLSGVVFGGGTKLTVL (SEQ ID NO: 2) |
| Common Light Chain 2 VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK (SEQ ID NO: 6) |

The invention also provides CDR portions of antibodies to PD-L1.

In one aspect, provided is an anti-PD-L1 antibody having any one of the VH CDR sequences and/or any one of the VL CDR sequences as listed in Table 4. In one aspect, the invention provides an antibody which specifically binds to PD-L1, wherein the antibody comprises: (a) a VH comprising (i) a VH CDR1 comprising SEQ ID NO: 41, 42, 43, 47, 48, or 49; (ii) a VH CDR2 comprising SEQ ID NO: 44, 45, 50, 51, 58, or 59; and (iii) a VH CDR3 comprising SEQ ID NO: 46, 52, 56, 57, or 60; and/or (b) a VL comprising (i) a VL CDR1 comprising SEQ ID NO: 19 or 53; (ii) a VL CDR2 comprising SEQ ID NO: 20 or 54; and (iii) a VL CDR3 comprising SEQ ID NO: 21 or 55.

TABLE 4

Exemplary Anti-PD-L1 CDR sequences

| mAb | VH CDR1 | VH CDR2 | VH CDR3 |
| --- | --- | --- | --- |
| PDL1_P06B05_245 VH | GFTFSNA (SEQ ID NO: 41) (Chothia) NAWMN (SEQ ID NO: 42) (Kabat) GFTFSNAWMN (SEQ ID NO: 43) (Extended) | KTKADGGT (SEQ ID NO: 44) (Chothia) RIKTKADGGTTDYAAPVKG (SEQ ID NO: 45) (Kabat) | DPGEYWDSVYGGMDY (SEQ ID NO: 46) (Chothia/Kabat) |
| PDL1_P04D09_113 VH | GFTFSSY (SEQ ID NO: 47) (Chothia) SYAMS (SEQ ID NO: 48) (Kabat) GFTFSSYAMS (SEQ ID NO: 49) (Extended) | GVRGGI (SEQ ID NO: 50) (Chothia) AIGVRGGITYYADSVKG (SEQ ID NO: 51) (Kabat) | ERSVGELVGIDQMDH (SEQ ID NO: 52) (Chothia/Kabat) |
| PDL1_P04D09_parent VH | GFTFSSY (SEQ ID NO: 47) (Chothia) SYAMS (SEQ ID NO: 48) (Kabat) GFTFSSYAMS (SEQ ID NO: 49) (Extended) | GVRGGI (SEQ ID NO: 50) (Chothia) AIGVRGGITYYADSVKG (SEQ ID NO: 51) (Kabat) | ERSVGELVGIDWMDH (SEQ ID NO: 56) (Chothia/Kabat) |

TABLE 4-continued

Exemplary Anti-PD-L1 CDR sequences

| | | | |
|---|---|---|---|
| PDL1_P06B05_parent VH | GFTFSNA (SEQ ID NO: 41) (Chothia) NAWMN (SEQ ID NO: 42) (Kabat) GFTFSNAWMN (SEQ ID NO: 43) (Extended) | KTKADGGT (SEQ ID NO: 44) (Chothia) RIKTKADGGTTDYA APVKG (SEQ ID NO: 45) (Kabat) | DPGSYWDSVYGGM DY (SEQ ID NO: 57) (Chothia/Kabat) |
| PDL1_P06A09_parent VH | GFTFSNA (SEQ ID NO: 41) (Chothia) NAWMN (SEQ ID NO: 42) (Kabat) GFTFSNAWMN (SEQ ID NO: 43) (Extended) | KSESDGGT (SEQ ID NO: 58) (Chothia) RIKSESDGGTTDYA APVKG (SEQ ID NO: 59) (Kabat) | DYRIDDWGYPYPGM DY (SEQ ID NO: 60) (Chothia/Kabat) |

VLCDRs

| mAb | VL CDR1 | VL CDR2 | VL CDR3 |
|---|---|---|---|
| Common Light Chain 1 VL | SGSSSNIGSNYVY (SEQ ID NO: 19) (Chothia/Kabat) | RNNQRPS (SEQ ID NO: 20) (Chothia/Kabat) | AAWDDDSLSGW (SEQ ID NO: 21) (Chothia/Kabat) |
| Common Light Chain 2 VL | RASQSISSYLN (SEQ ID NO: 53) (Chothia/Kabat) | AASSLQS (SEQ ID NO: 54) (Chothia/Kabat) | QQSYSTPLT (SEQ ID NO: 55) (Chothia/Kabat) |

In some embodiments, provided herein is an anti-PD-L1 antibody, wherein the VH comprises the sequence of SEQ ID NO: 4, 5, 10, 11, or 12, or a variant thereof with 1, 2, 3, 4, 5, 6, 7, 8, 9, or 10 amino acid substitutions in the sequence; and/or wherein the VL comprises the sequence of SEQ ID NO: 2 or 6, or a variant thereof with 1, 2, 3, 4, 5, 6, 7, 8, 9, or 10 amino acid substitutions in the sequence. Optionally the substitutions are conservative amino acid substitutions. Optionally, the substitutions are not in a CDR region.

The invention also encompasses scFv of anti-PD-L1 antibodies provided herein. Other forms of single chain antibodies, such as diabodies or minibodies are also encompassed.

In some embodiments, an anti-PD-L1 antibody provided herein is a monoclonal antibody. Optionally, the anti-PD-L1 antibody is a human antibody or a humanized antibody.

CD47/PD-L1 Bispecific Antibodies

In some embodiments, provided herein are CD47/PD-L1 bispecific antibodies.

A CD47/PD-L1 bispecific antibody comprises at least a first antigen-binding portion (which specifically binds to CD47) and a second antigen-binding portion (which specifically binds to PD-L1). In some embodiments, the first antigen-binding portion comprises a first VH and the second antigen-binding portion comprises a second VH. In some embodiments, the first antigen-binding portion comprises a first VH and a first VL, and the second antigen-binding portion comprises a second VH and a second VL. In some embodiments, the amino acid sequence of the first VL and the second VL is the same.

A CD47/PD-L1 bispecific antibody provided herein may contain any of the anti-CD47 antibodies provided herein (e.g. as the first antigen-binding portion) and any of the anti-PD-L1 antibodies provided herein (e.g. as the second antigen-binding portion).

In some embodiments, provided is a CD47/PD-L1 bispecific antibody comprising a first antigen-binding portion that specifically binds to CD47 and second antigen-binding portion that specifically binds to PD-L1, wherein the first antigen-binding portion comprises a VH and/or a VL, wherein: (a) the VH comprises SEQ ID NO: 1 and (b) the VL comprises SEQ ID NO: 2 and the second antigen-binding portion comprises a VH and/or a VL, wherein: (a) the VH comprises SEQ ID NO: 4; and (b) the VL comprises SEQ ID NO: 2.

In some embodiments, provided is a CD47/PD-L1 bispecific antibody comprising a first antigen-binding portion that specifically binds to CD47 and second antigen-binding portion that specifically binds to PD-L1, wherein the first antigen-binding portion comprises a VH and/or a VL, wherein: (a) the VH comprises SEQ ID NO: 3 and (b) the VL comprises SEQ ID NO: 2 and the second antigen-binding portion comprises a VH and/or a VL, wherein: (a) the VH comprises SEQ ID NO: 4; and (b) the VL comprises SEQ ID NO: 2.

In some embodiments, provided is a CD47/PD-L1 bispecific antibody comprising a first antigen-binding portion that specifically binds to CD47 and second antigen-binding portion that specifically binds to PD-L1, wherein the first antigen-binding portion comprises any one of the VH CDR sequences as listed in Table 2, and wherein the second antigen-binding portion comprises any one of the VH CDR sequences as listed in Table 4.

In some embodiments, provided herein is a CD47/PD-L1 bispecific antibody comprising a first antigen-binding portion that specifically binds to CD47 and a second antigen-binding portion that specifically binds to PD-L1, wherein the bispecific antibody contains the VH and VL or CDRs thereof of any of the anti-CD47 antibodies as shown in Table 5, and wherein the bispecific antibody contains the VH and VL or CDRs thereof of any of the anti-PD-L1 antibodies as shown in Table 5.

TABLE 5

VH and VL sequences of anti-CD47 and anti-PD-L1 antibodies:

| Antibody | VH SEQ ID NO: | VL SEQ ID NO: |
|---|---|---|
| CD47_P01A11_75 | 1 | 2 |
| CD47_P01A11_497 | 3 | 2 |
| CD47_P01A11_parent | 7 | 2 |
| CD47_P14D04_parent | 8 | 6 |
| CD47_P01A08_parent | 9 | 2 |
| PDL1_P06B05_245 | 4 | 2 |
| PDL1_P04D09_113 | 5 | 6 |
| PDL1_P04D09_parent | 10 | 6 |
| PDL1_P06B05_parent | 11 | 2 |
| PDL1_P06A09_parent | 12 | 2 |

In some embodiments, provided herein is an antibody that binds to CD47 and/or PD-L1, and competes with an antibody described herein for binding to the respective antigen, e.g. that competes with CD47_P01A11_75, CD47_P01A11_497, CD47_P01A11_parent, CD47_P14D04_parent or CD47_P01A08_parent for binding to CD47, or that competes with PDL1_P06B05_245, PDL1_P04D09_113, PDL1_P04D09_parent, PDL1_P06B05_parent, or PDL1_P06A09_parent for binding to PD-L1.

The binding affinity ($K_D$) of the antibodies as described herein to CD47 or PD-L1, can be about 0.001 nM to about 6500 nM. In some embodiments, the binding affinity is about any of 6500 nM, 6000 nM, 5500 nM, 4500 nM, 4000 nM, 3500 nM, 3000 nM, 2500 nM, 2000 nM, 1500 nM, 1000 nM, 750 nM, 500 nM, 400 nM, 300 nM, 250 nM, 200 nM, 150 nM, 100 nM, 75 nM, 50 nM, 45 nM, 40 nM, 35 nM, 30 nM, 25 nM, 20 nM, 19 nM, 17 nM, 16 nM, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, 0.002 nM, or 0.001 nM. In some embodiments, the binding affinity is less than about any of 6500 nM, 6000 nM, 5500 nM, 5000 nM, 4000 nM, 3000 nM, 2000 nM, 1000 nM, 900 nM, 800 nM, 500 nM, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, 0.5 nM, 0.1 nM, 0.05 nM, 0.01 nM or lower nM.

In some embodiments, a CD47/PD-L1 bispecific antibody provided herein has greater affinity for PD-L1 than CD47 (e.g. the affinity of the second antigen-binding portion of the antibody for PD-L1 is greater than the affinity of the first antigen-binding portion of the antibody for CD47). Without being bound by theory, a CD47/PD-L1 bispecific antibody having greater affinity for PD-L1 than CD47 may be desirable in order reduce potential side-effects or toxicity potentially caused by the anti-CD47 antibody binding portion of the antibody. In addition to being expressed on various cancer cells, CD47 is expressed in a wide range of healthy human cells (including red blood cells (RBCs)), and there is a potential for significant undesirable side effects from anti-CD47 antibodies, due to the binding of anti-CD47 antibodies to healthy cells. A CD47/PD-L1 bispecific antibody containing a relatively low-affinity anti-CD47 antigen binding portion may preferentially bind to cancer cells over healthy cells, due to the relatively low affinity of such bispecific antibodies for healthy cells such as RBCs (which express CD47 protein but not PD-L1 protein), and the relatively higher affinity of such bispecific antibodies for cancer cells (which frequently express both CD47 and PD-L1). In some embodiments, in a CD47/PD-L1 bispecific antibody provided herein that has greater affinity for PD-L1 than CD47, the anti-PD-L1 binding portion of the antibody has at least 2× (i.e. 2-fold), 3×, 5×, 10×, 20×, 50×, 100×, 200×, 500×, 1000×, 2000×, or 5000× greater affinity for PD-L1 than the anti-CD47 binding portion of the antibody has for CD47. In some embodiments, in a CD47/PD-L1 bispecific antibody provided herein that has greater affinity for PD-L1 than CD47, the anti-PD-L1 binding portion of the antibody a binding affinity ($K_D$) for PD-L1 of approximately or less than 10 nM, 5 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM and the anti-CD47 binding portion of the antibody a binding affinity ($K_D$) for CD47 of approximately or less than 1000 nM, 600 nM, 500 nM, 400 nM, 300 nM, 200 nM, 100 nM, 50 nM, 20 nM, or 10 nM, wherein the affinity of the anti-PD-L1 binding portion of the antibody for PD-L1 at least 2×, 3×, 5×, 10×, 20×, 50×, 100×, 200×, 500×, 1000×, 2000×, or 5000× greater (i.e. smaller value in nM, since greater affinity is indicated by lower nM value) than the affinity of the anti-CD47 binding portion of the antibody for CD47.

In some embodiments, a CD47/PD-L1 bispecific antibody provided herein has similar affinity for both CD47 and PD-L1.

A CD47/PD-L1 bispecific antibody provided herein can have any suitable format. In some embodiments, a bispecific antibody provided herein comprises a full-length human antibody. In some embodiments, the human antibody has an IgG1, IgG2, IgG3, or IgG4 isotype. In some embodiments, an antibody comprises an immunologically inert Fc chain.

In some embodiments, a bispecific CD47/PD-L1 antibody provided herein can have a format as described in Suurs, F. V. et al, Pharmacology & Therapeutics, 201 (2019) pp. 103-119.

Optionally, a bispecific antibody can be prepared by constructing scFv fragments with short linkers (e.g., about 3-10 residues) between the VH and VLs such that inter-chain but not intra-chain pairing of the V regions is achieved, resulting in a bivalent fragment, i.e., fragment having two antigen-binding sites. Bispecific antibodies can be derived from full length antibodies or antibody fragments (e.g., F(ab')$_2$ bispecific antibodies). Diabodies are described more fully in, for example, EP404,097; WO93/11161; and Hollinger et al., Proc. Natl. Acad. Sci. USA 90:6444-6448, 1993.

The present invention encompasses a bispecific antibody comprising an Fc chain or domain, or portions thereof. In some embodiments, the Fc chain, or portion(s) thereof, comprises one or more constant domain(s) of the Fc chain of IgG1, IgG2, IgG3 or IgG4 (e.g., a CH2 or CH3 domain). In another embodiment, the invention encompasses molecules comprising an Fc chain or portion thereof, wherein the Fc chain or portion thereof comprises at least one amino acid modification (e.g. substitution) relative to a comparable wild-type Fc chain or portion thereof. Variant Fc chains are well known in the art, and are primarily used to alter the phenotype of the antibody comprising the variant Fc chain as assayed in any of the binding activity or effector function assays well known in the art, e.g., ELISA, SPR analysis, or ADCC. Such variant Fc chains, or portions thereof, may extend the plasma half-life and stability exhibited by a bispecific antibody of the invention comprising an Fc chain or portion thereof. In another embodiment, the invention encompasses the use of any Fc variant known in the art.

In some embodiments, one or more modifications are made to the amino acids of the Fc chain to reduce the affinity and avidity of the Fc chain and, thus, the bispecific antibody molecule of the invention, for one or more FcγR receptors. In a specific embodiment, the invention encompasses bispecific antibodies comprising a variant Fc chain, or portion thereof, wherein the variant Fc chain comprises at least one amino acid modification relative to a wild-type Fc chain which variant Fc chain only binds one FcγR, wherein the FcγR is FcγRIIIA. In another specific embodiment, the invention encompasses bispecific antibodies comprising a variant Fc chain, or portion thereof, wherein the variant Fc chain comprises at least one amino acid modification relative to a wild type Fc chain which variant Fc chain only binds one FcγR, wherein the FcγR is FcγRIIA. In another specific embodiment, the invention encompasses bispecific antibodies comprising a variant Fc chain or portion thereof, wherein the variant Fc chain comprises at least one amino acid modification relative to a wild-type Fc chain, which variant Fc chain only binds one FcγR, wherein the FcγR is FcγRIIB. In another embodiment, the invention encompasses molecules comprising a variant Fc chain wherein the variant confers or mediates decreased ADCC activity (or other effector function) and/or an increased binding to FcγRIIB (CD32B), relative to a molecule comprising no Fc chain or comprising a wild-type Fc chain, as measured using methods known to one skilled in the art and described herein.

The invention also encompasses the use of an Fc chain comprising domains or regions from two or more IgG isotypes. As known in the art, amino acid modification of the Fc chain may profoundly affect Fc-mediated effector function and/or binding activity. However, these alterations in functional characteristics may be further refined and/or manipulated when implemented in the context of selected IgG isotypes. Similarly, the native characteristics of the isotype Fc may be manipulated by one or more amino acid modifications. The multiple IgG isotypes (i.e., IgG1, IgG2, IgG3 and IgG4) exhibit differing physical and functional properties including serum half-life, complement fixation, FcγR binding affinities and effector function activities (e.g., ADCC, CDC) due to differences in the amino acid sequences of their hinge and/or Fc chains.

In some embodiments, the amino acid modification and IgG Fc chain are independently selected based on their respective, separate binding and/or effector function activities in order to engineer a bispecific antibody with desired characteristics. In a particular embodiment, the amino acid modifications and IgG hinge/Fc chains have been separately assayed for binding and/or effector function activity as described herein or known in the art in the context of an IgG1. In one embodiment, the amino acid modification and IgG hinge/Fc chain display similar functionality, e.g., decreased ADCC activity (or other effector function) and/or an increased binding to FcγRIIB in the context of the bispecific antibody or other Fc-containing molecule (e.g., and immunoglobulin). In another embodiment, the invention encompasses variant Fc chains comprising combinations of amino acid modifications known in the art and selected IgG regions that exhibit novel properties, which properties were not detectable when the modifications and/or regions were independently assayed as described herein.

In some such embodiments, the bispecific antibodies of the present invention comprise a first heterodimer-promoting domain on the first polypeptide chain and a second heterodimer-promoting domain on the second polypeptide chain. Taken together, the first and second heterodimer-promoting domains drive heterodimerization and/or stabilize the bispecific antibody (e.g., by interaction of a knob and hole on complementary heterodimer-promoting domains) and/or serve to stabilize the bispecific antibody.

In some embodiments, the Fc domain of a bispecific antibody provided herein comprises a first Fc chain and a second Fc chain, wherein each of the first and second Fc chain comprises at least one amino acid modification as compared to wildtype Fc chain, to form a knob or a hole. In some embodiments, the first Fc chain comprises a knob and the second Fc chain comprises a hole. In some embodiments, the first Fc chain may comprise a CH2 and/or CH3 domain modified to comprise either a knob or a hole. In some embodiments, the first Fc chain comprises mutations Y349C and/or T366W, to form a knob; and the second Fc chain comprises mutations S354C, T366S, L368A, and/or Y407V, to form a hole, (numbering according to the EU index). In some specific embodiments, the mutations lead to a reduced effector function.

In a particular embodiment of each of the foregoing, a first Fc chain comprises a sequence of SEQ ID NO: 65, to form a knob (human IgG1 Fc chain with knob mutations); and a second Fc chain comprises a sequence of SEQ ID NO: 66, to form a hole (human IgG1 Fc chain with hole mutations).

Optionally, an anti-CD47 VH provided herein may be genetically fused to the amino acid sequence of SEQ ID NO: 65 or SEQ ID NO: 66 to form a first heavy chain of a bispecific antibody, and an anti-PD-L1 VH provided herein may be genetically fused to amino acid sequence of SEQ ID NO: 65 or SEQ ID NO: 66 to form a second heavy chain of a bispecific antibody, wherein one is genetically fused to SEQ ID NO: 65 and the other is genetically fused to SEQ ID NO: 66. Optionally, an anti-CD47 or anti-PD-L1 heavy chain provided herein containing the amino acid sequence of SEQ ID NO: 65 or SEQ ID NO: 66 may lack the C-terminal lysine of SEQ ID NO: 65 or SEQ ID NO: 66. In other words, in some circumstances, the C-terminal lysine of the heavy chain of an antibody provided herein may be cleaved from the antibody, and such antibodies that are missing the C-terminal lysine are included within the scope of antibody heavy chains provided herein.

In some embodiments, provided is a CD47/PD-L1 bispecific antibody having an anti-CD47 heavy chain and an anti-PD-L1 heavy chain amino acid sequence as in provided in Table 6A. Both of the anti-CD47 heavy chains in Table 6A have a hole mutation in the Fc chain, and the anti-PD-L1 heavy chain has a knob mutation in the Fc chain. In some embodiments, provided herein is a CD47/PD-L1 bispecific antibody comprising an anti-CD47 heavy chain comprising the amino acid sequence as shown in SEQ ID NO: 61, and an anti-PD-L1 heavy chain comprising the amino acid sequence as shown in SEQ ID NO: 64. Optionally, the CD47/PD-L1 bispecific antibody may further comprise two copies of light chain comprising the amino acid sequence as shown in SEQ ID NO: 62. The light chain comprising the amino acid sequence as shown in SEQ ID NO: 62 is a common light chain, and it can pair with the anti-CD47 heavy chain and with the anti-PD-L1 heavy chain. In some embodiments, provided herein is a CD47/PD-L1 bispecific antibody comprising an anti-CD47 heavy chain comprising the amino acid sequence as shown in SEQ ID NO: 63, and an anti-PD-L1 heavy chain comprising the amino acid sequence as shown in SEQ ID NO: 64. Optionally, the CD47/PD-L1 bispecific antibody may further comprise two copies of light chain comprising the amino acid sequence as shown in SEQ ID NO: 62.

TABLE 6A

Heavy Chain and Light Chain Sequences for exemplary CD47/PD-L1 Bispecific Antibodies

| Description | Sequence |
| --- | --- |
| CD47_P01A11_75 Heavy Chain [human IgG1 containing hole mutations in Fc chain; hole mutations are underlined (S354C, T366S, L368A, and Y407V, EU numbering); VH italicized] | *QVQLVQSGAEVKKPGSSVKVSCKASGYTFSSYAISWVRQAPGQG LEWMGGISPIFGTANYAQKFQGRVTITADESTSTAYMELSSLRSED TAVYYCARDAGRSSDVGWYVGAIDVWGQGTLVTVSSASTKGPSV* FPLAPSSKSTSGGTAALGCLVKDYFPEPVTVSWNSGALTSGVHTF PAVLQSSGLYSLSSVVTVPSSSLGTQTYICNVNHKPSNTKVDKKVE PKSCDKTHTCPPCPAPELLGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPAPIEKTISKAKGQPREPQVYTLP PC̲REEMTKNQVSLS̲C̲AVKGFYPSDIAVEWESNGQPENNYKTTPP VLDSDGSFFLV̲SKLTVDKSRWQQGNVFSCSVMHEALHNHYTQKS LSLSPGK(SEQ ID NO: 61) |
| CD47_P01A11_497 Heavy Chain [human IgG1 containing hole mutations in Fc chain; hole mutations are underlined (S354C, T366S, L368A, and Y407V, EU numbering); VH italicized] | *QVQLVQSGAEVKKPGSSVKVSCKASGGTFTSYAISWVRQAPGQG LEWMGGISPIFGTANYAQKFQGRVTITADESTSTAYMELSSLRSED TAVYYCARDAGRSSDVGWYVGALDVWGQGTLVTVSSASTKGPS* VFPLAPSSKSTSGGTAALGCLVKDYFPEPVTVSWNSGALTSGVHT FPAVLQSSGLYSLSSWTVPSSSLGTQTYICNVNHKPSNTKVDKKV EPKSCDKTHTCPPCPAPELLGGPSVFLFPPKPKDTLMISRTPEVTC VVVDVSHEDPEVKFNWYVDGVEVHNAKTKPREEQYNSTYRVVSV LTVLHQDWLNGKEYKCKVSNKALPAPIEKTISKAKGQPREPQVYTL PPC̲REEMTKNQVSLS̲C̲AVKGFYPSDIAVEWESNGQPENNYKTTP PVLDSDGSFFLV̲SKLTVDKSRWQQGNVFSCSVMHEALHNHYTQK SLSLSPGK (SEQ ID NO: 63) |
| PDL1_P06B05_245 Heavy Chain [human IgG1 containing knob mutations; knob mutations are underlined (Y349C and Y366W); VH italicized] | *EVQLVESGGGLVKPGGSLRLSCAASGFTFSNAWMNWVRQAPGK GLEWVGRIKTKADGGTTDYAAPVKGRFTISRDDSKNTLYLQMNSL KTEDTAVYYCTTDPGEYWDSVYGGMDYWGQGTLVTVSSASTKG* PSVFPLAPSSKSTSGGTAALGCLVKDYFPEPVTVSWNSGALTSGV HTFPAVLQSSGLYSLSSVVTVPSSSLGTQTYICNVNHKPSNTKVDK KVEPKSCDKTHTCPPCPAPELLGGPSVFLFPPKPKDTLMISRTPEV TCVVVVDVSHEDPEVKFNWYVDGVEVHNAKTKPREEQYNSTYRVV SVLTVLHQDWLNGKEYKCKVSNKALPAPIEKTISKAKGQPREPQV C̲TLPPSREEMTKNQVSLW̲CLVKGFYPSDIAVEWESNGQPENNYK TTPPVLDSDGSFFLYSKLTVDKSRWQQGNVFSCSVMHEALHNHY TQKSLSLSPGK(SEQ ID NO: 64) |
| Common Light Chain 1 Full Light Chain (VL italicized) | *QSVLTQPPSASGTPGQRVTISCSGSSSNIGSNYVYWYQQLPGTAP KLLIYRNNQRPSGVPDRFSGSKSGTSASLAISGLRSEDEADYYCAA WDDSLSGVVFGGGTKLTVLGQPKAAPSVTLFPPSSEELQANKATL* VCLISDFYPGAVTVAWKADSSPVKAGVETTTPSKQSNNKYAASSY LSLTPEQWKSHRSYSCQVTHEGSTVEKTVAPTECS (SEQ ID NO: 62) |

In any embodiment provided herein that includes an antibody having a heavy chain, included within the scope of the embodiment is an antibody that does not have the C-terminal lysine in the heavy chain. Accordingly, for example, for an antibody provided herein that includes the heavy chain having the amino acid sequence as shown in SEQ ID NO: 61, also provided is an antibody having the amino acid sequence as shown in SEQ ID NO: 61, except the C-terminal lysine of SEQ ID NO: 61. In another example, for an antibody provided herein that includes the heavy chain having the amino acid sequence as shown in SEQ ID NO: 63, also provided is an antibody having the amino acid sequence as shown in SEQ ID NO: 63, except for the C-terminal lysine of SEQ ID NO: 63. In another example, for an antibody provided herein that includes the heavy chain having the amino acid sequence as shown in SEQ ID NO: 64, also provided is an antibody having the amino acid sequence as shown in SEQ ID NO: 64, except for the C-terminal lysine of SEQ ID NO: 64. In some embodiments, provided herein is a CD47/PD-L1 bispecific antibody comprising a first heavy chain having the amino acid sequence as shown in SEQ ID NO: 61 and a second heavy chain having the amino acid sequence as shown in SEQ ID NO: 64, wherein neither, one, or both of the heavy chains is missing the C-terminal lysine of the respective heavy chain sequence. In some embodiments, provided herein is a CD47/PD-L1 bispecific antibody comprising a first heavy chain having the amino acid sequence as shown in SEQ ID NO: 63 and a second heavy chain having the amino acid sequence as shown in SEQ ID NO: 64, wherein neither, one, or both of the heavy chains is missing the C-terminal lysine of the respective heavy chain sequence.

In one aspect, provided herein is a CD47/PD-L1 bispecific antibody, wherein the bispecific antibody comprises a first heavy chain specific for CD47, a second heavy chain specific for PD-L1, and a common light chain; wherein the first heavy chain has an amino acid sequence encoded by the nucleic acid sequence of the insert of the plasmid deposited with the ATCC and having ATCC Accession No. PTA-126910; the second heavy chain has an amino acid sequence encoded by the nucleic acid sequence of the insert of the plasmid deposited with the ATCC and having ATCC Accession No. PTA-126911, and the common light chain has an amino acid sequence encoded by the nucleic acid sequence of the insert of the plasmid deposited with the ATCC and having ATCC Accession No. PTA-126912.

Polynucleotides and Methods of Producing, Characterizing and Modifying Antibodies The present invention also includes polynucleotides that encode the antibodies of the invention, including the polypeptides and binding regions of the antibodies. The polynucleotides encoding the molecules of the invention may be obtained, and the nucleotide sequence of the polynucleotides determined, by any method known in the art.

The polynucleotides that encode the antibodies of the present invention may include the following: only the coding sequence for the variant, the coding sequence for the variant and additional coding sequences such as a functional polypeptide, or a signal or secretory sequence or a pro-protein sequence; the coding sequence for the antibody and non-coding sequence, such as introns or non-coding sequence 5' and/or 3' of the coding sequence for the antibody. The term "polynucleotide encoding an antibody" encompasses a polynucleotide which includes additional coding sequence for the variant but also a polynucleotide which includes additional coding and/or non-coding sequence. It is known in the art that a polynucleotide sequence that is optimized for a specific host cell/expression system can readily be obtained from the amino acid sequence of the desired protein (see GENEART® AG, Regensburg, Germany).

In some embodiments, provided herein is a polynucleotide comprising a nucleotide sequence encoding any of the amino acid sequences of anti-CD47 or anti-PD-L1 antibodies provided elsewhere herein (e.g. in any of Tables 1, 2, 3, 4 or 5). Also provided herein are related vectors and host cells comprising the polynucleotides.

In some embodiments, provided herein is a polynucleotide encoding the VH of an antibody that specifically binds to CD47, wherein the polynucleotide comprises the nucleotide sequence as shown in SEQ ID NO: 67 or 69. In some embodiments, provided herein is a polynucleotide encoding the VL of a common light chain of an antibody that specifically binds to CD47 and PD-L1, wherein the polynucleotide comprises the nucleotide sequence as shown in SEQ ID NO: 68. In some embodiments, provided herein is a polynucleotide encoding the VH of an antibody that specifically binds to PD-L1, wherein the polynucleotide comprises the nucleotide sequence as shown in SEQ ID NO: 70. In some embodiments, provided herein is a polynucleotide encoding the heavy chain of an antibody that specifically binds to CD47, wherein the polynucleotide comprises the nucleotide sequence as shown in SEQ ID NO: 71 or 73. In some embodiments, provided herein is a polynucleotide encoding the common light chain of an antibody that specifically binds to CD47 and PD-L1, wherein the polynucleotide comprises the nucleotide sequence as shown in SEQ ID NO: 72. In some embodiments, provided herein is a polynucleotide encoding the heavy chain of an antibody that specifically binds to PD-L1, wherein the polynucleotide comprises the nucleotide sequence as shown in SEQ ID NO: 74. Also provided herein are related vectors and host cells comprising a polynucleotide that comprises a nucleotide sequence as shown in any of SEQ ID NOs 67-74.

In some embodiments, provided herein is a polynucleotide comprising a nucleotide sequence as shown in Table 6B.

TABLE 6B

| Description | Sequence |
|---|---|
| Polynucleotide encoding CD47_P01A11_75 VH (SEQ ID NO: 1) | Caagtgcaactggtgcagtcaggcgccgaagtcaagaagccggggtctagcgtgaaagtgtcgtgca aggcctcaggctacaccttctcctcctatgcgatcagctgggtcagacaggcgcctggacagggactcg agtggatgggtggcatttcccccatcttcggaaccgcaaactacgcccagaagtttcagggccgcgtga ccatcactgccgacgagagcacttcgaccgcctacatggaactgtcctcgctgcggtccgaagataccg ccgtgtactactgtgctcgggatgctggaaggtcctccgacgtcggttggtacgtgggggccattgacgtc tggggacagggaactctggtcaccgtctcctca (SEQ ID NO: 67) |
| Polynucleotide encoding Common light chain 1 VL (SEQ ID NO: 2) | Caatcagtgctgacccagcctccctctgcatccggaacccccgggacagagagtcaccatctcctgctcc ggttcgtcctcgaacatcggcagcaactacgtgtactggtaccagcaactccctgggactgccccaaag ctgctcatctatcggaacaatcagcggccttccggagtgccggacaggttctccggaagcaaatcggc actagcgcctcactggctattagcggtttgcgctccgaggacgaagccgactactactgtgccgcgtggg atgattccctttccggcgtcgtgttcggggcggaaccaagctgactgtgcta (SEQ ID NO: 68) |
| Polynucleotide encoding CD47_P01A11_497 VH (SEQ ID NO: 3) | Caagtgcagcttgtgcagtcgggcgctgaagtcaagaagcctgggtcatcggtgaaagtgtcctgcaa ggcctctggggggaaccttcacgtcctacgcgattagctgggtccgccaagcacgggacagggactga agtggatgggcggaatcagcccccatcttcggcactgccaactacgcccagaagtttcagggtcgcgtga ctatcaccgccgacgaatccacctcaaccgcctacatggaactgagctccctgcggtccgaggacact gccgtgtattactgtgcgagagatgctggacggtcgtccgatgtcggttggtacgtgggagccctcgacgt ctggggacagggcaccctggtcaccgtctcctca (SEQ ID NO: 69) |
| Polynucleotide encoding PDL1_P06B05_245 VH (SEQ ID NO: 4) | Gaagtgcagctggttgaaagcggtggtggcctggtcaaacctggtggtagcctgcgtctgagctgtgcg gcgtcaggttttacgttctcaaatgcgtggatgaattgggtcagacaggcgcccggaaagggactggaa tgggtcgggcgcattaaaacaaaggctgatggcggtactaccgattatgcagcgccggtgaaaggacg ttttaccatctcacgtgacgattcgaaaaacaccctgtaccttcagatgaacagcctgaaaaccgaggac accgcagtatactattgcactaccgacccgggcgagtactgggatagcgtttatggcggtatggattactg gggccaaggtacactggtcaccgtctcctca (SEQ ID NO: 70) |
| Polynucleotide encoding CD47_P01A11_75 Heavy Chain | caagtgcaactggtgcagtcaggcgccgaagtcaagaagccggggtctagcgtgaaagtgtcgtgca aggcctcaggctacaccttctcctcctatgcgatcagctgggtcagacaggcgcctggacagggactcg agtggatgggtggcatttcccccatcttcggaaccgcaaactacgcccagaagtttcagggccgcgtga ccatcactgccgacgagagcacttcgaccgcctacatggaactgtcctcgctgcggtccgaagataccg ccgtgtactactgtgctcgggatgctggaaggtcctccgacgtcggttggtacgtgggggccattgacgtc |

TABLE 6B-continued

| Description | Sequence |
| --- | --- |
| (SEQ ID NO: 61) | tggggacagggaactctggtcaccgtctcctcagcgtcgaccaagggcccatcggtcttccccctggca ccctcctccaagagcacctctgggggcacagcggccctgggctgcctggtcaaggactacttccccga accggtgacggtgtcgtggaactcaggcgccctgaccagcggcgtgcacaccttcccggctgtcctaca gtcctcaggactctactccctcagcagcgtggtgaccgtgccctccagcagcttgggcacccagaccta catctgcaacgtgaatcacaagcccagcaacaccaaggtggacaagaaagttgagcccaaatcttgt gacaaaactcacacatgcccaccgtgcccagcacctgaactcctggggggaccgtcagtcttcctcttc cccccaaaacccaaggacaccctcatgatctcccggacccctgaggtcacatgcgtggtggtggacgt gagccacgaagaccctgaggtcaagttcaactggtacgtggacggcgtggaggtgcataatgccaag acaaagccgcgggaggagcagtacaacagcacgtaccgtgtggtcagcgtcctcaccgtcctgcacc aggactggctgaatggcaaggagtacaagtgcaaggtctccaacaaagccctcccagcccccatcga gaaaaccatctccaaagccaaagggcagccccgagaaccacaggtgtacaccctgcccccatgccg ggaggagatgaccaagaaccaggtcagcctgtcctgcgcggtcaaaggcttctatcccagcgacatcg ccgtggagtgggagagcaatgggcagccggagaacaactacaagaccacgcctcccgtgctggact ccgacggctccttcttcctcgttagcaagctcaccgtggacaagagcaggtggcagcagggggaacgtct tctcatgctccgtgatgcatgaggctctgcacaaccactacacgcagaagagcctctccctgtccccgg aaaa (SEQ ID NO: 71) |
| Polynucleotide encoding Common Light Chain 1 Full Light Chain (SEQ ID NO: 62) | Caatcagtgctgacccagcctccctctgcatccggaaccccgggacagagagtcaccatctcctgctcc ggttcgtcctcgaacatcggcagcaactacgtgtactggtaccagcaactccctgggactgcccccaaag ctgctcatctatcggaacaatcagcggccttccggagtgccagacaggttctccggaagcaaatcggg actagcgcctcactggctattagcggtttgcgctccgaggacgaagccgactactactgtgccgcgtggg atgattccctttcggcgtcgtgttcggggggaaccaagctgactgtgctaggtcagcccaaggctgc cccctcggtcactctgttcccaccctcctctgaggagcttcaagccaacaaggccacactggtgtgtctca taagtgacttctacccgggagccgtgacagtggcctggaaggcagatagcagccccgtcaaggcggg agtggagaccaccacaccctccaaacaaagcaacaacaagtacgcggccagcagctacctgagcct gacgcctgagcagtggaagtcccacagaagctacagctgccaggtcacgcatgaagggagcaccgt ggagaagacagtggcccctacagaatgttca (SEQ ID NO: 72) |
| Polynucleotide encoding CD47_P01A11_497 Heavy Chain (SEQ ID NO: 63) | caagtgcagcttgtgcagtcgggcgctgaagtcaagaagcctgggtcatcggtgaaagtgtcctgcaag gcctctggggggaaccttcacgtcctacgcgattagctgggtcgccaagcaccgggacagggactgga gtggatgggcggaatcagcccatcttcggcactgccaactacgcccagaagtttcagggtcgcgtgac tatcaccgccgacgaatccacctcaaccgcctacatggaactgagctccctgcggtccgaggacactg ccgtgtattactgtgcgagagatgctggacggtcgtccgatgtcggttggtacgtgggagccctcgacgtc tggggacagggcaccctggtcaccgtctcctcagcgtcgaccaagggcccatcggtcttccccctggca ccctcctccaagagcacctctgggggcacagcggccctgggctgcctggtcaaggactacttccccga accggtgacggtgtcgtggaactcaggcgccctgaccagcggcgtgcacaccttcccggctgtcctaca gtcctcaggactctactccctcagcagcgtggtgaccgtgccctccagcagcttgggcacccagaccta catctgcaacgtgaatcacaagcccagcaacaccaaggtggacaagaaagttgagcccaaatcttgt gacaaaactcacacatgcccaccgtgcccagcacctgaactcctggggggaccgtcagtcttcctcttc cccccaaaacccaaggacaccctcatgatctcccggacccctgaggtcacatgcgtggtggtggacgt gagccacgaagaccctgaggtcaagttcaactggtacgtggacggcgtggaggtgcataatgccaag acaaagccgcgggaggagcagtacaacagcacgtaccgtgtggtcagcgtcctcaccgtcctgcacc aggactggctgaatggcaaggagtacaagtgcaaggtctccaacaaagccctcccagcccccatcga gaaaaccatctccaaagccaaagggcagccccgagaaccacaggtgtacaccctgcccccatgccg ggaggagatgaccaagaaccaggtcagcctgtcctgcgcggtcaaaggcttctatcccagcgacatcg ccgtggagtgggagagcaatgggcagccggagaacaactacaagaccacgcctcccgtgctggact ccgacggctccttcttcctcgttagcaagctcaccgtggacaagagcaggtggcagcagggggaacgtct tctcatgctccgtgatgcatgaggctctgcacaaccactacacgcagaagagcctctccctgtccccgg aaaa (SEQ ID NO: 73) |
| Polynucleotide encoding PDL1_P06B05_245 Heavy Chain (SEQ ID NO: 64) | gaagtgcagctggttgaaagcggtggtggcctggtcaaacctggtggtagcctgcgtctgagctgtgcgg cgtcaggttttacgttctcaaatgcgtggatgaattgggtcagacaggcgcccggaaagggactggaat gggtcgggcgcattaaaacaaaggctgatggcggtactaccgattatgcagcgccggtgaaaggacgt tttaccatctcacgtgacgattcgaaaaacaccctgtaccttcagatgaacagcctgaaaaccgaggac accgcagtatactattgcactaccgaccgggcgagtactgggatagcgtttatggcggtatggattactg gggccaaggtacactggtcaccgtctcctcagcgtcgaccaagggcccatcggtcttccccctggcacc ctcctccaagagcacctctgggggcacagcggccctgggctgcctggtcaaggactacttccccgaac cggtgacggtgtcgtggaactcaggcgccctgaccagcggcgtgcacaccttcccggctgtcctacagt cctcaggactctactccctcagcagcgtggtgaccgtgccctccagcagcttgggcacccagacctaca tctgcaacgtgaatcacaagcccagcaacaccaaggtggacaagaaagttgagcccaaatcttgtga caaaactcacacatgcccaccgtgcccagcacctgaactcctggggggaccgtcagtcttcctcttccc ccaaaacccaaggacaccctcatgatctcccggacccctgaggtcacatgcgtggtggtggacgtgag ccacgaagaccctgaggtcaagttcaactggtacgtggacggcgtggaggtgcataatgccaagaca aagccgcgggaggagcagtacaacagcacgtaccgtgtggtcagcgtcctcaccgtcctgcaccagg actggctgaatggcaaggagtacaagtgcaaggtctccaacaaagccctcccagcccccatcgagaa aaccatctccaaagccaaagggcagccccgagaaccacaggtgtgcaccctgcccccatcccggga ggagatgaccaagaaccaggtcagcctgtggtgcctggtcaaaggcttctatcccagcgacatcgccgt ggagtgggagagcaatgggcagccggagaacaactacaagaccacgcctcccgtgctggactccga cggctccttcttcctctatagcaagctcaccgtggacaagagcaggtggcagcagggggaacgtcttctca tgctccgtgatgcatgaggctctgcacaaccactacacgcagaagagcctctccctgtccccgaaaa (SEQ ID NO: 74) |

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include mature and immature mRNAs, such as precursor mRNAs (pre-mRNA) or heterogeneous nuclear mRNAs (hnRNA) and mature mRNAs. Additional coding or non-coding sequences may, but need not, be present within a polynucleotide of the present invention, and a polynucleotide may, but need not, be linked to other molecules and/or support materials.

It will be appreciated by those of ordinary skill in the art that, as a result of the degeneracy of the genetic code, there are many nucleotide sequences that encode amino acid sequences provided herein. Polynucleotides that vary due to differences in codon usage are specifically contemplated by the present invention.

In one aspect, provided herein is an isolated nucleic acid encoding at least the VH of an antibody that specifically binds to CD47, wherein the nucleic acid comprises the nucleic acid sequence of the insert of the plasmid deposited with the ATCC and having ATCC Accession No. PTA-126910. Also provided herein is a polypeptide having the amino acid sequence encoded by the nucleic acid sequence of the insert of the plasmid deposited with the ATCC and having ATCC Accession No. PTA-126910.

In one aspect, provided herein is an isolated nucleic acid encoding at least the VL of the common light chain of an antibody that specifically binds to CD47 and PD-L1, wherein the nucleic acid comprises the nucleic acid sequence of the insert of the plasmid deposited with the ATCC and having ATCC Accession No. PTA-126912. Also provided herein is a polypeptide having the amino acid sequence encoded by the nucleic acid sequence of the insert of the plasmid deposited with the ATCC and having ATCC Accession No. PTA-126912.

In one aspect, provided herein is an isolated nucleic acid encoding at least the VH of an antibody that specifically binds to PD-L1, wherein the nucleic acid comprises the nucleic acid sequence of the insert of the plasmid deposited with the ATCC and having ATCC Accession No. PTA-126911. Also provided herein is a polypeptide having the amino acid sequence encoded by the nucleic acid sequence of the insert of the plasmid deposited with the ATCC and having ATCC Accession No. PTA-126911.

In one aspect, the invention provides a method of making any of the polynucleotides described herein. For example, the polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art (e.g., Sambrook et al., 1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose expressing genes encoding the antibody, polypeptide or protein of interest. Non-limiting examples of mammalian host cells include but not limited to COS, HeLa, and CHO cells. See also PCT Publication No. WO87/04462. Suitable non-mammalian host cells include prokaryotes (such as *E. coli* or *B. subtillis*) and yeast (such as *S. cerevisae, S. pombe*; or *K. lactis*). A cell overexpressing the antibody or protein of interest can be identified by known screening methods.

The invention also encompasses modifications to the antibodies provided herein, including functionally equivalent antibodies which do not significantly affect their properties and variants which have enhanced or decreased activity and/or affinity. For example, the amino acid sequence may be mutated to obtain an antibody with the desired binding affinity to CD47 and/or PD-L1. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 7 under the heading of "conservative substitutions." If such substitutions result in a change in biological activity, then more substantial changes, denominated "exemplary substitutions" in Table 7, or as further described below in reference to amino acid classes, may be introduced and the products screened.

TABLE 7

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:
(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is VH CDR3 and/or VL CDR3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH 15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that has increased affinity to a human Fc gamma receptor, is immunologically inert or partially inert, e.g., does not trigger complement mediated lysis, does not stimulate antibody-dependent cell mediated cytotoxicity (ADCC), or does not activate macrophages; or has reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 29:2613-2624, 1999; PCT Application No. PCT/GB99/01441; and/or UK Application No. 9809951.8. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the Fc chain of an antibody provided herein may be modified to ablate effector function. For example, the Fc chain of human IgG1 may be modified to introduce mutations L234A, L235A and G237A using standard primer-directed PCR mutagenesis to oblate effector function due to binding to FcγRIII, providing for an effector function null phenotype (Canfield et al., J. Exp. Med (1991) 173: 1483-1491; Shields et al., J. Biol. Chem. (2001) 276: 6591-604).

In some embodiments, a bispecific antibody provided herein may be engineered to comprise at least one cysteine residue that may interact with a counterpart cysteine residue on another polypeptide chain of the invention to form an inter-chain disulfide bond. The inter-chain disulfide bonds may serve to stabilize the bispecific antibody, improving expression and recovery in recombinant systems, resulting in a stable and consistent formulation, as well as, improving the stability of the isolated and/or purified product in vivo. The cysteine residue or residues may be introduced as a single amino acid or as part of larger amino-acid sequence, e.g., hinge region, in any portion of the polypeptide chain. In a specific aspect, at least one cysteine residue is engineered to occur at the C-terminus of the polypeptide chain.

Compositions, Methods, and Kits

In some embodiments, the invention encompasses compositions, including pharmaceutical compositions comprising antibodies of the invention as described herein or made by the methods and having the characteristics described herein. As used herein, pharmaceutical compositions may comprise one or more antibodies that bind to CD47, one or more antibodies that bind to PD-L1, one or more bispecific antibodies that bind to CD47 and PD-L1, and/or one or more polynucleotides comprising sequences encoding one or more these antibodies. These compositions may further comprise suitable excipients, such as pharmaceutically acceptable excipients including buffers, which are well known in the art.

The invention provided herein further encompasses methods and compositions for treatment, prevention or management of cancer in a subject, comprising administering to the subject a therapeutically effective amount of an anti-CD47, an anti-PD-L1, or a bispecific CD47/PD-L1 antibody provided herein. Anti-CD47, anti-PD-L1, and CD47/PD-L1 bispecific antibodies may be particularly useful for the prevention, inhibition, reduction of growth and/or regression of primary tumors and metastasis of cancer cells.

In one aspect, the invention provides a method for treating a condition associated with CD47 and/or PD-L1 expression in a subject. In some embodiments, the method of treating a condition associated with CD47 and/or PD-L1 expression in a subject comprises administering to the subject in need thereof an effective amount of a composition (e.g., pharmaceutical composition) comprising the respective anti-CD47, anti-PD-L1 and/or CD47/PD-L1 bispecific antibodies, as described herein. The conditions associated with CD47 and/or PD-L1 expression include, but are not limited to, abnormal CD47 and/or PD-L1 expression, altered or aberrant CD47 and/or PD-L1 expression, malignant cells expressing CD47 and/or PD-L1, and a proliferative disorder (e.g., cancer). In specific embodiments, the cancer is bladder cancer, breast cancer, clear cell kidney cancer, head/neck squamous cell carcinoma [squamous cell carcinoma of the head and neck (SCCHN)], lung squamous cell carcinoma, lung adenocarcinoma, malignant melanoma, non-small-cell lung cancer (NSCLC), ovarian cancer, pancreatic cancer, prostate cancer, renal cell carcinoma, small-cell lung cancer (SCLC), triple negative breast cancer, urothelial cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), small lymphocytic lymphoma (SLL), endometrial cancer, B-cell acute lymphoblastic leukemia, colorectal cancer, glioblastoma, uterine cancer, cervical cancer, penile cancer, or non-melanoma skin cancer.

In one aspect, the present invention provides an anti-CD47 antibody, anti-PD-L1 antibody, and/or CD47/PD-L1 bispecific antibody described herein, or a pharmaceutical composition comprising such antibody for use in therapy. In a particular embodiment, the invention also provides a provides an anti-CD47 antibody, anti-PD-L1 antibody, and/or CD47/PD-L1 bispecific antibody for use in treating a CD47 and/or PD-L1 associated disorder. In specific embodiments, the CD47 and/or PD-L1 associated disorder is a cancer defined herein.

The present invention further provides an anti-CD47 antibody, anti-PD-L1 antibody, and/or CD47/PD-L1 bispecific antibody described herein, or a pharmaceutical composition comprising such antibody for use in the manufacture of a medicament for use in therapy. In some embodiments, the therapy is a treatment of a CD47 and/or PD-L1 associated disorder. In specific embodiments, the CD47 and/or PD-L1 associated disorder is cancer.

In a specific aspect, an anti-CD47 antibody, anti-PD-L1 antibody, and/or CD47/PD-L1 bispecific antibody provided herein inhibits or reduces the growth of cancer cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of cancer cells in the absence of the antibody or a bispecific antibody.

In a specific aspect, an anti-CD47 antibody, anti-PD-L1 antibody, and/or CD47/PD-L1 bispecific antibody provided herein kill cells or inhibits or reduces the growth of cancer cells at least 5%, at least 10%, at least 20%, at least 25%, at least 30%, at least 35%, at least 40%, at least 45%, at least 50%, at least 60%, at least 70%, at least 75%, at least 80%, at least 85%, at least 90%, at least 95%, or at least 100% better than in the absence of the antibody or a bispecific antibody.

In some embodiments, the methods and uses described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

The invention further encompasses administering the molecules of the invention in combination with other therapies known to those skilled in the art for the treatment or prevention of cancer including but not limited to, current standard and experimental chemotherapies, biological therapies, immunotherapies, radiation therapies, or surgery. In some aspects, the molecules of the invention may be administered in combination with a therapeutically or prophylactically effective amount of one or more agents, therapeutic antibodies or other agents known to those skilled in the art for the treatment and/or prevention of cancer.

Accordingly, methods and uses for treating cancer include administering to a subject in need thereof an effective amount of an antibody or bispecific antibody of the present invention in combination with a chemotherapeutic agent. Such combination treatment may be administered separately, sequentially, or simultaneously. Suitable chemotherapeutic agents include, but are not limited to, at least one additional agent such as bevacizumab, cetuximb, sirolimus, panitumumab, 5-fluorouracil (5-FU), capecitabine, tivozanib, irinotecan, oxaliplatin, cisplatin, trifluridine, tipiracil, leucovori, gemcitabine and/or erlotinib hydrochloride.

The dosage amounts and frequencies of administration provided herein are encompassed by the terms therapeutically effective and prophylactically effective. The dosage and frequency further may vary according to factors specific for each patient depending on the specific therapeutic or prophylactic agents administered, the severity and type of cancer, the route of administration, as well as age, body weight, response, and the past medical history of the patient. Suitable regimens may be selected by one skilled in the art by considering such factors and by following, for example, dosages reported in the literature and recommended in the Physician's Desk Reference (56$^{th}$ ed., 2002).

The antibodies or the bispecific antibodies of the present invention may be in the form of a pharmaceutical composition for administration that are formulated to be appropriate for the selected mode of administration, and pharmaceutically acceptable diluent or excipients, such as buffers, surfactants, preservatives, solubilizing agents, isotonicity agents, stabilizing agents, carriers, and the like. Remington's Pharmaceutical Sciences, Mack Publishing Co., Easton Pa., 18$^{th}$ ed., 1995, provides a compendium of formulation techniques as are generally known to practitioners.

These pharmaceutical compositions may be administered by any means known in the art that achieve the generally intended purpose to treat cancer. The route of administration may be parenteral, defined herein as referring to modes of administration that include but not limited to transesophageal, intratumoral, transcolonoscopically, transcutaneously, intravenous, intramuscular, intraperitoneal, subcutaneous, and intraarticular injection and infusion. The manner of administration and dosing of the of the molecules according to the invention (e.g., anti-CD47 antibodies, anti-PD-L1 antibodies, CD47/PD-L1 bispecific antibodies, related pharmaceutical compositions) depend on the type of disease to be combated, where appropriate the stage thereof, the antigen to be controlled, the kind of concurrent treatment, if any, frequency of treatment, the nature of the effect desired, and also the body weight, the age, the health the diet and the sex of the patient. Thus, the dosage regimen actually employed can vary widely and therefore can deviate from the dosage regimens set forth herein.

Various formulations of the antibodies of the present invention (e.g., anti-CD47 antibodies, anti-PD-L1 antibodies, CD47/PD-L1 bispecific antibodies) may be used for administration. In some embodiments, the antibodies may be administered neat. In some embodiments, the antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 21st Ed. Mack Publishing, 2005.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

The antibodies (e.g., anti-CD47 antibodies, anti-PD-L1 antibodies, CD47/PD-L1 bispecific antibodies) as described herein can be administered using any suitable method, including by injection (e.g., intraperitoneally, intravenously, subcutaneously, intramuscularly, etc.). The antibody, e.g., monoclonal antibody or bispecific antibody, also be administered via inhalation, as described herein. Generally, for administration of the antibody of the present, the dosage depends upon the host treated and the particular mode of administration. In one embodiment, the dose range of the antibody of the present invention will be about 0.001 µg/kg body weight to about 20,000 µg/kg body weight. The term "body weight" is applicable when a patient is being treated. When isolated cells are being treated, "body weight" as used herein refers to a "total cell body weight". The term "total body weight" may be used to apply to both isolated cell and patient treatment. All concentrations and treatment levels are expressed as "body weight" or simply "kg" in this application are also considered to cover the analogous "total cell body weight" and "total body weight" concentrations. However, those of ordinary skill in the art will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 µg/kg, 5 µg/kg, 10 µg/kg, 12 µg/kg, 15 mg/kg, 20 mg/kg, and/or 30 mg/kg. All of these dosages are exemplary, and any dosage in-between these points is also expected to be of use in the invention. Any of the above dosage ranges or dosage levels may be employed for an antibody of the present invention. For repeated administrations over several days or longer, depending on the condition, the treatment is sustained until a desired suppression of symptoms occurs or until sufficient therapeutic levels are achieved, for example, to inhibit or delay tumor growth/progression or metastasis of cancer cells.

Generally, for administration of antibodies provided herein, the candidate dosage can be administered daily, every week, every other week, every three weeks, every four weeks, every five weeks, every six weeks, every seven weeks, every eight weeks, every ten weeks, every twelve weeks, or more than every twelve weeks.

In some embodiments, the candidate dosage is administered daily with the dosage ranging from about any of 1 µg/kg, to 30 µg/kg, to 300 µg/kg, to 3 mg/kg, to 30 mg/kg, to 100 mg/kg or more, depending on the factors mentioned above. For example, daily dosage of about 0.01 mg/kg, about 0.03 mg/kg, about 0.1 mg/kg, about 0.3 mg/kg, about 1 mg/kg, about 2.5 mg/kg, about 3 mg/kg, about 5 mg/kg, about 10 mg/kg, about 15 mg/kg, and about 25 mg/kg may be used.

In some embodiments, the candidate dosage is administered every week with the dosage ranging from about any of 1 µg/kg, to 30 µg/kg, to 300 µg/kg, to 3 mg/kg, to 30 mg/kg, to 100 mg/kg or more, depending on the factors mentioned above. For example, a weekly dosage of about 0.01 mg/kg, about 0.03 mg/kg, about 0.1 mg/kg, about 0.3 mg/kg, about 0.5 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every two weeks with the dosage ranging from about any of 1 µg/kg, to 30 µg/kg, to 300 µg/kg, to 3 mg/kg, to 30 mg/kg, to 100 mg/kg or more, depending on the factors mentioned above. For example, a bi-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every three weeks with the dosage ranging from about any of 1 µg/kg, to 30 µg/kg, to 300 µg/kg, to 3 mg/kg, to 30 mg/kg, to 100 mg/kg or more, depending on the factors mentioned above. For example, a tri-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In some embodiments, the candidate dosage is administered every month or every four weeks with the dosage ranging from about any of 1 µg/kg, to 30 µg/kg, to 300 µg/kg, to 3 mg/kg, to 30 mg/kg, to 100 mg/kg or more, depending on the factors mentioned above. For example, a monthly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In other embodiments, the candidate dosage is administered daily with the dosage ranging from about 0.01 mg to about 1200 mg or more, depending on the factors mentioned above. For example, daily dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, or about 1200 mg may be used.

In other embodiments, the candidate dosage is administered every week with the dosage ranging from about 0.01 mg to about 2000 mg or more, depending on the factors mentioned above. For example, weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every two weeks with the dosage ranging from about 0.01 mg to about 2000 mg or more, depending on the factors mentioned above. For example, bi-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every three weeks with the dosage ranging from about 0.01 mg to about 2500 mg or more, depending on the factors mentioned above. For example, tri-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg may be used.

In other embodiments, the candidate dosage is administered every four weeks or month with the dosage ranging from about 0.01 mg to about 3000 mg or more, depending on the factors mentioned above. For example, monthly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, or about 3000 mg may be used.

Other dosage regimens may also be useful, depending on the pattern of pharmacokinetic decay that the practitioner wishes to achieve. In one embodiment, the antibody of the present invention is administered in an initial priming dose followed by a higher and/or continuous, substantially constant dosage. In some embodiments, dosing from one to four times a week is contemplated. In other embodiments, dosing once a month or once every other month or every three months is contemplated. The progress of this therapy is easily monitored by conventional techniques and assays. The dosing regimen can vary over time.

For the purpose of the present invention, the appropriate dosage of an antibody (e.g., anti-CD47 antibodies, anti-PD-L1 antibodies, CD47/PD-L1 bispecific antibodies) will depend on the antibody or compositions thereof employed, the type and severity of symptoms to be treated, whether the agent is administered for therapeutic purposes, previous therapy, the patient's clinical history and response to the agent, the patient's clearance rate for the administered agent, and the discretion of the attending physician. Typically the clinician will administer an antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of antibodies may be appropriate. Various formulations and devices for achieving sustained release are known in the art.

In one embodiment, dosages for an antibody (e.g., anti-CD47 antibodies, anti-PD-L1 antibodies, CD47/PD-L1 bispecific antibodies) may be determined empirically in individuals who have been given one or more administration(s) of the antibody. Individuals are given incremental dosages of an antibody. To assess efficacy, an indicator of the disease can be followed.

In some embodiments, an antibody provided herein (e.g., anti-CD47 antibodies, anti-PD-L1 antibodies, CD47/PD-L1 bispecific antibodies) may be administered to a subject that has previously received an anti-PD-1 or anti-PD-L1 antibody therapeutic for treatment of a disease (e.g. cancer). In some embodiments, an antibody provided herein may be an administered to a subject that has previously received an anti-PD-1 or anti-PD-L1 antibody therapeutic for treatment of a disease, and for which the previous anti-PD-1 or anti-PD-L1 antibody therapeutic is of limited or no efficacy in the subject (e.g. for which the subject's disease is resistant to treatment with the prior anti-PD-1 or anti-PD-L1 therapeutic).

In some embodiments, an antibody provided herein (e.g., anti-CD47 antibodies, anti-PD-L1 antibodies, CD47/PD-L1 bispecific antibodies) may be administered to a subject who has a cancer that tests positive for PD-L1 expression. In some embodiments an antibody provided herein may be administered to a subject who has a cancer that does not test positive for PD-L1 expression.

"PD-L1 expression" as used herein refers to any detectable level of expression of PD-L1 protein on the cell surface or of PD-L1 mRNA within a cell or tissue. PD-L1 protein expression may be detected with a diagnostic anti-PD-L1 antibody in an immunohistochemistry (IHC) assay of a tumor tissue section or by flow cytometry. PD-L1 expression by cells may also be detected by PET imaging, using a binding agent (e.g. antibody) that specifically binds to PD-L1. Techniques for detecting and measuring PD-L1 mRNA expression include, for example, RT-PCR and real-time quantitative RT-PCR.

Several approaches have been described for quantifying PD-L1 expression in IHC assays of tumor tissue sections. See, e.g., Thompson, R. H., et al., PNAS 101 (49); 17174-17179 (2004); Thompson, R. H. et al., Cancer Res. 66:3381-3385 (2006); Gadiot, J., et al., Cancer 117:2192-2201 (2011); Taube, J. M. et al., Sci Transl Med 4, 127ra37 (2012); and Toplian, S. L. et al., New Eng. JAed 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section may be counted as positive for PD-L1 expression if a certain percentage of tumor cells are positive for PD-L1 expression. For example a tumor tissue section may be counted as positive for PD-L1 expression if at least 0.5%, 1%, 5%, 10%, 20%, 30%, 50%, 75%, 90%, or 95% of the tumor cells are positive for PD-L1 expression.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining may be separately quantified, such as <5%, 5 to 9%, and then in 10% increments up to 100%. For tumor cells, PD-L1 expression may be counted as negative if the score is less than, for example 1%, 2%, or 5%, and positive if the score is greater than 1%, 2%, or 5%, respectively. PD-L1 expression in the infiltrating immune cells may be reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section may be counted as positive for PD-L1 expression by immune infiltrates if the AIS is greater than 5.

The level of PD-L1 mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some embodiments, PD-L1 expression in a tumor sample is determined to be elevated if PD-L1 protein (and/or PD-L1 mRNA) in the sample is at least 10%, 20%, or 30% greater than in the control.

In some embodiments, PD-L1 expression in a cancer is detected using a diagnostic anti-PD-L1 antibody, in an immunohistochemistry (IHC) assay on a tissue section of a tumor sample removed from the patient. Typically, a sample of the tumor is tested to determine PD-L1 expression prior to treatment with an antibody provided herein, but it could also be tested after initiation of treatment.

Specific examples of diagnostic anti-human PD-L1 mAbs useful as diagnostic mAbs for IHC detection of PD-L1 expression in tumor tissue sections are antibody 20C3 and antibody 22C3, which are described in WO2014/100079. Exemplary PD-L1 IHC tests include the PD-L1 IHC 22C3 PharmDx (Daco) and the Ventana PD-L1 SP263 assay.

In certain embodiments, the administration of an antibody (e.g., anti-CD47 antibodies, anti-PD-L1 antibodies, CD47/PD-L1 bispecific antibodies) leads to at least one effect selected from the group consisting of inhibition of tumor growth, tumor regression, reduction in the size of a tumor, reduction in tumor cell number, delay in tumor growth, abscopal effect, inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

Administration of an antibody (e.g., anti-CD47 antibodies, anti-PD-L1 antibodies, CD47/PD-L1 bispecific antibodies) in accordance with the method in the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced doses.

Therapeutic formulations of the antibody (e.g., anti-CD47 antibodies, anti-PD-L1 antibodies, CD47/PD-L1 bispecific antibodies) used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, an anti-CD47 antibody, anti-PD-L1 antibody, or CD47/PD-L1 bispecific antibody provided herein may be administered in combination with the administration of one or more additional therapeutic agents. Optionally, the additional therapeutic agent may include an additional anti-cancer agent. These include, but are not limited to, the administration of a biotherapeutic agent and/or a chemotherapeutic agent, such as but not limited to, a vaccine, a CAR-T cell-based therapy, radiotherapy, a cytokine therapy, a CD3 bispecific antibody, an inhibitor of other immunosuppressive pathways, an inhibitor of angiogenesis, a T cell activator, an inhibitor of a metabolic pathway, an mTOR inhibitor, an inhibitor of an adenosine pathway, a tyrosine kinase inhibitor including but not limited to Inlyta, ALK inhibitors and sunitinib, a BRAF inhibitor, an epigenetic modifier, an IDO1 inhibitor, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD40, CD-40L, CTLA-4, OX-40, 4-1BB, TIGIT, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of biotherapeutic agents include therapeutic antibodies, immune modulating agents, and therapeutic immune cells.

Therapeutic antibodies may have specificity against a variety of different of antigens. For example, therapeutic antibodies may be directed to a tumor associated-antigen, such that binding of the antibody to the antigen promotes death of the cell expressing the antigen. In other example, therapeutic antibodies may be directed to an antigen (e.g. PD-1) on an immune cell, such that binding of the antibody prevents downregulation of the activity of the cell expressing the antigen (and thereby promotes activity of the cell expressing the antigen). In some situations, a therapeutic antibody may function through multiple different mechanisms (for example, it may both i) promote death of the cell expressing the antigen, and ii) prevent the antigen from causing down-regulation of the activity of immune cells in contact with the cell expressing the antigen). Therapeutic antibodies may be directed to, for example, the antigens listed as follows. For some antigens, exemplary antibodies directed to the antigen are also included below (in brackets/parenthesis after the antigen). The antigens as follow may also be referred to as "target antigens" or the like herein. Target antigens for therapeutic antibodies herein include, for example: 4-1BB (e.g. utomilumab); 5T4; A33; alpha-folate receptor 1 (e.g. mirvetuximab soravtansine); Alk-1; BCMA [e.g. PF-06863135 (see U.S. Pat. No. 9,969,809)]; BTN1A1 (e.g. see WO2018222689); CA-125 (e.g. abagovomab); Carboanhydrase IX; CCR2; CCR4 (e.g. mogamulizumab); CCR5 (e.g. leronlimab); CCR8; CD3 [e.g. blinatumomab (CD3/CD19 bispecific), PF-06671008 (CD3/P-cadherin bispecific), PF-06863135 (CD3/BCMA bispecific), CD19 (e.g. blinatumomab, MOR208); CD20 (e.g. ibritumomab tiuxetan, obinutuzumab, ofatumumab, rituximab, ublituximab); CD22 (inotuzumab ozogamicin, moxetumomab pasudotox); CD25; CD28; CD30 (e.g. brentuximab vedotin); CD33 (e.g. gemtuzumab ozogamicin); CD38 (e.g. daratumumab, isatuximab), CD40; CD-40L; CD44v6; CD47; CD52 (e.g. alemtuzumab); CD63; CD79 (e.g. polatuzumab vedotin); CD80; CD123; CD276/B7-H3 (e.g. omburtamab); CDH17; CEA; ClhCG; CTLA-4 (e.g. ipilimumab, tremelimumab), CXCR4; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIII; Endosialin; EpCAM (e.g. oportuzumab monatox); FAP; Fetal Acetylcholine Receptor; FLT3 (e.g. see WO2018/220584); GD2 (e.g. dinutuximab, 3F8); GD3; GITR; GloboH; GM1; GM2; GUCY2C (e.g. PF-07062119); HER2/neu [e.g. margetuximab, pertuzumab, trastuzumab; ado-trastuzumab emtansine, trastuzumab duocarmazine, PF-06804103 (see U.S. Pat. No. 8,828,401)]; HER3; HER4; ICOS; IL-10; ITG-AvB6; LAG-3 (e.g. relatlimab); Lewis-Y; LG; Ly-6; M-CSF [e.g. PD-0360324 (see U.S. Pat. No. 7,326,414)]; MCSP; mesothelin; MUC1; MUC2; MUC3; MUC4; MUC5AC; MUC5B; MUC7; MUC16; Notch1; Notch3; Nectin-4 (e.g. enfortumab vedotin); OX40 [e.g. PF-04518600 (see U.S. Pat. No. 7,960,515)]; P-Cadherin [e.g. PF-06671008 (see WO2016/001810)]; PCDHB2; PD-1 [e.g. BCD-100, camrelizumab, cemiplimab, genolimzumab (CBT-501), MEDI0680, nivolumab, pembrolizumab, RN888 (see WO2016/092419), sintilimab, spartalizumab, STI-A1110, tislelizumab, TSR-042]; PD-L1 (e.g. atezolizumab, durvalumab, BMS-936559 (MDX-1105), or LY3300054); PDGFRA (e.g. olaratumab); Plasma Cell Antigen; PolySA; PSCA; PSMA; PTK7 [e.g. PF-06647020 (see U.S. Pat. No. 9,409,995)]; Ror1 SAS; SCRx6; SLAMF7 (e.g. elotuzumab); SHH; SIRPa (e.g. ED9, Effi-DEM); STEAP; TGF-beta; TIGIT; TIM-3; TMPRSS3; TNF-alpha precursor; TROP-2 (e.g sacituzumab govitecan); TSPAN8; VEGF (e.g. bevacizumab, brolucizumab); VEGFR1 (e.g. ranibizumab); VEGFR2 (e.g. ramucirumab, ranibizumab); Wue-1.

Therapeutic antibodies administered in combination with the antibodies provided herein may have any suitable format. For example, therapeutic antibodies may have any format as described elsewhere herein. In some embodiments, a therapeutic antibody may be a naked antibody. In some embodiments, a therapeutic antibody may be linked to a drug or other agent (also known as an "antibody-drug conjugate" (ADC)). In some embodiments, a therapeutic antibody against a particular antigen may incorporated into a multi-specific antibody (e.g. a bispecific antibody).

In some embodiments, an anti-CD47 antibody, anti-PD-L1 antibody, or CD47/PD-L1 bispecific antibody provided herein may be administered in combination with a pattern recognition receptor (PRR) agonists, immunostimulatory cytokines, and cancer vaccines. There are multiple classes of PRR molecules, including toll-like receptors (TLRs), RIG-I-like receptors (RLRs), nucleotide-binding oligomerization domain (NOD)-like receptors (NLRs), C-type lectin receptors (CLRs), and Stimulator of Interferon Genes (STING) protein. Other PRRs include, for example, DNA-dependent Activator of IFN-regulatory factors (DAI) and Absent in Melanoma 2 (AIM2).

In some embodiments, an anti-CD47 antibody, anti-PD-L1 antibody, or CD47/PD-L1 bispecific antibody provided herein may be administered in combination with a molecule which activates one or more TLRs, herein referred to herein as "TLR agonists". TLR agonists can include, for example, small molecules (e.g. organic molecule having a molecular weight under about 1000 Daltons), as well as large molecules (e.g. oligonucleotides and proteins). Some TLR agonists are specific for a single type of TLR (e.g. TLR3 or TLR9), while some TLR agonists activate two or more types of TLR (e.g. both TLR7 and TLR8). Exemplary TLR agonists provided herein include agonists of TLR2, TLR3, TLR4, TLR5, TLR6, TLR7, TLR8, and TLR9. Exemplary small molecule TLR agonists include those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091,214; U.S. Patent Publication Nos. 2004/0091491, 2004/0176367, and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826, WO 2006/009832, WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852. Additional examples of small molecule TLR agonists include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), and certain 3-.beta.-D-ribofuranosylthiazolo [4,5-d]pyrimidine derivatives (such as those described in U.S. Publication No. 2003/0199461), and certain small molecule immuno-potentiator compounds such as those described, for example, in U.S. Patent Publication No. 2005/0136065. Exemplary large molecule TLR agonists include as oligonucleotide sequences. Some TLR agonist oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other TLR agonist nucleotide sequences lack CpG sequences and are described, for example, in International Patent Publication No. WO 00/75304. Still other TLR agonist nucleotide sequences include guanosine- and uridine-rich single-stranded RNA (ssRNA) such as those described, for example, in Heil et ah, Science, vol. 303, pp. 1526-1529, Mar. 5, 2004. Other TLR agonists include biological molecules such as aminoalkyl glucosaminide phosphates (AGPs) and are described, for example, in U.S. Pat. Nos. 6,113,918; 6,303,347; 6,525,028; and 6,649,172. TLR agonists also include inactivated pathogens or fractions thereof, which may activate multiple different types of TLR receptor. Exemplary pathogen-derived TLR agonists include BCG, *Mycobacterium obuense* extract, Talimogene laherparepvec (T-Vec) (derived from HSV-1), and Pexa-Vec (derived from vaccina virus). In some embodiments, an anti-CD47 antibody, anti-PD-L1 antibody, or CD47/PD-L1 bispecific antibody provided herein may be administered in combination with SPM-105 (derived from autoclaved mycobacteria), OM-174 (lipid A derivative), OmpS1 (porin from *Salmonella typhi*), OmpS1 (porin from *Salmonella typhi*), OspA (from *Borrelia burgdorferi*), MALP-2 (mycoplasmal macrophage-activating lipopeptide-2 kD), STF (soluble tuberculosis factor), CU-T12-9, Diprovocim, and lipopeptides derived from cell-wall components such as PAM2CSK4, PAM3CSK4, and PAM3Cys. Examples of TLR2 agonists that are useful in the treatment methods, medicaments, and uses of the present invention include, for example, bacterial lipoproteins (e.g. diacylated lipoproteins) and derivatives thereof such as SPM-105 (derived from autoclaved mycobacteria), OM-174 (lipid A derivative), OmpS1 (porin from *Salmonella typhi*), OmpS1 (porin from *Salmonella typhi*), OspA (from *Borrelia burgdorferi*), MALP-2 (mycoplasmal macrophage-activating lipopeptide-2 kD), STF (soluble tuberculosis factor), CU-T12-9, Diprovocim, Amplivant, and lipopeptides derived from cell-wall components such as PAM2CSK4, PAM3CSK4, and PAM3Cys. Examples of TLR3 agonists that are useful in the treatment methods, medicaments, and uses of the present invention include TLR3 ligands such as synthetic dsRNA, polyinosinic-polycytidylic acid ["poly(I:C)"] (available from, e.g. InvivoGen in high molecular weight (HMW) and low molecular weight (LMW) preparations), polyadenylic-polyuridylic acid ["poly(A:U)"] (available from, e.g. InvivoGen), polyI-CLC (see Levy et al., Journal of Infectious Diseases, vol. 132, no. 4, pp. 434-439, 1975), Ampligen (see Jasani et al., Vaccine, vol. 27, no. 25-26, pp. 3401-3404, 2009), Hiltonol, Rintatolimod, and RGC100 (see Naumann et al., Clinical and Developmental Immunology, vol. 2013, article ID 283649). Examples of TLR4 agonists that are useful in the treatment methods, medicaments, and uses of the present invention include, for example, bacterial lipopolysaccharides (LPS) and derivatives thereof such as B:0111 (Sigma), monophosphoryl lipid A (MPLA), 3DMPL (3-O-deacylated MPL), GLA-AQ, G100, AS15, ASO2, GSK1572932A (GlaxoSmithKline, UK). Examples of TLR5 agonists that are useful in the treatment methods, medicaments, and uses of the present invention include, for example, bacterial flagellin purified from *B. subtilis*, flagellin purified from *P. aeruginosa*, flagellin purified from *S. typhimurium*, and recombinant flagellin (all available from InvivoGen), entolimod (CBLB502; a pharmacologically optimized flagellin derivative). Examples of TLR6 agonists that are useful in the treatment methods, medicaments, and uses of the present invention include, for example, many of the TLR2 agonists provided above, as TLR2 and TLR6 can form a heterodimer. TLR6 can also form a heterodimer with TLR4, and TLR6 agonists can include various TLR4 agonists provided above. Examples of TLR7 agonists that are useful in the treatment methods, medicaments, and uses of the present invention include recombinant single-stranded ("ss") RNA, imidazoquinoline compounds such as imiquimod (R837), gardiquimod, and resiquimod (R848); Loxoribine (7-allyl-7,8-dihydro-8-oxo-guanosine) and related compounds; 7-Thia-8-oxoguanosine, 7-deazaguanosine, and related guanosine analogs; ANA975 (Anadys Pharmaceuticals) and related compounds; SM-360320 (Sumimoto); 3M-01, 3M-03, 3M-852, and 3M-S-34240 (3M Pharmaceuticals); GSK2245035 (GlaxoSmithKline; an 8-oxoadenine molecule), AZD8848 (AstraZeneca; an 8-oxoadenine molecule), MEDI9197 (Medimmune; formerly 3M-052), ssRNA40, and adenosine analogs such as UC-1V150 (Jin et al., Bioorganic Medicinal Chem Lett (2006) 16:4559-4563, compound 4). Many TLR7 agonists are also TLR8 agonists. Examples of TLR8 agonists that are useful in the treatment methods, medicaments, and uses of the present invention include recombinant single-stranded ssRNA, imiquimod (R837), gardiquimod, resiquimod (R848), 3M-01, 3M-03, 3M-852, and 3M-S-34240 (3M Pharmaceuticals); GSK2245035 (GlaxoSmithKline; an 8-oxoadenine molecule), AZD8848 (AstraZeneca; an 8-oxoadenine molecule), MEDI9197 (Medimmune; formerly 3M-052), Poly-G10, Motolimod, and various TLR7 agonists provided above (as previously noted, many TLR7 agonists are also TLR8 agonists). Examples of TLR9 agonists that are useful in the treatment methods, medicaments, and uses of the present invention include unmethylated CpG-containing DNA, immunostimulatory oligodeoxynucleotides (ODN), such as CpG-containing ODN such as CpG24555, CpG10103, CpG7909 (PF-3512676/agatolimod), CpG1018, AZD1419, ODN2216, MGN1703, SD-101, 1018ISS, and CMP-001.

TLR9 agonists also include nucleotide sequences containing a synthetic cytosine-phosphate-2'-deoxy-7-deazaguanosine dinucleotide (CpR) (Hybridon, Inc.), dSLIM-30L1, and immunoglobulin-DNA complexes. Exemplary TLR9 agonists are disclosed in WO2003/015711, WO2004/016805, WO2009/022215, PCT/US95/01570, PCT/US97/19791, and U.S. Pat. Nos. 8,552,165, 6,194,388 and 6,239,116, which are each hereby incorporated by reference for all purposes.

Examples of RLRs agonists that are useful in the treatment methods, medicaments, and uses of the present invention include, for example, short double-stranded RNA with uncapped 5' triphosphate (RIG-I agonist); poly I:C (MDA-5 agonist), and BO-112 (MDA-A agonist).

Examples of NLR agonists that are useful in the treatment methods, medicaments, and uses of the present invention include, for example, liposomal muramyl tripeptide/mifamurtide (NOD2 agonist).

CLRs include various PRRs that detect, e.g. carbohydrates and glycoproteins. CLRs include both transmembrane CLRs and secreted CLRs. Examples of CLRs include, for example, DEC-205/CD205, macrophage mannose receptor (MMR), Dectin-1, Dectin-2, mincle, DC-SIGN, DNGR-1, and mannose-binding lectin (MBL).

Examples of CLR agonists that are useful in the treatment methods, medicaments, and uses of the present invention include, for example, MD-fraction (a purified soluble beta-glucan extract from *Grifola frondosa*) and imprime PGG (a beta 1,3/1,6-glucan PAMP derived from yeast).

Examples of STING agonists that are useful in the treatment methods, medicaments, and uses of the present invention include various immunostimulatory nucleic acids, such as synthetic double stranded DNA, cyclic di-GMP, cyclic-GMP-AMP (cGAMP), synthetic cyclic dinucleotides (CDN) such as MK-1454 and ADU-S100 (MIW815), and small molecules such as P0-424.

Examples of immunostimulatory cytokines that are useful in the treatment methods, medicaments, and uses of the present invention include GM-CSF, G-CSF, IFN-alpha, IFN-gamma; IL-2 (e.g. denileukin difitox), IL-6, IL-7, IL-11, IL-12, IL-15, IL-18, IL-21, and TNF-alpha.

Examples of cancer vaccines that are useful in the treatment methods, medicaments, and uses of the present invention include, for example, sipuleucel-T and talimogene laherparepvec (T-VEC).

Examples of immune cell therapies that are useful in the treatment methods, medicaments, and uses of the present invention include, for example, tumor-infiltrating lymphocytes (TILs) and chimeric antigen receptor T cells (CAR-T cells).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g., calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; KRAS inhibitors; MCT4 inhibitors;

MAT2a inhibitors; tyrosine kinase inhibitors such as sunitinib, axitinib; alk/c-Met/ROS inhibitors such as crizotinib, lorlatinib; mTOR inhibitors such as temsirolimus, gedatolisib; src/abl inhibitors such as bosutinib; cyclin-dependent kinase (CDK) inhibitors such as palbociclib, PF-06873600; erb inhibitors such as dacomitinib; PARP inhibitors such as talazoparib; SMO inhibitors such as glasdegib, PF-5274857; EGFR T790M inhibitors such as PF-06747775; EZH2 inhibitors such as PF-06821497; PRMTS inhibitors such as PF-06939999; TGFRβr1 inhibitors such as PF-06952229; and pharmaceutically acceptable salts, acids or derivatives of any of the above. In specific embodiments, such additional therapeutic agent is bevacizumab, cetuximab, sirolimus, panitumumab, 5-fluorouracil (5-FU), capecitabine, tivozanib, irinotecan, oxaliplatin, cisplatin, trifluridine, tipiracil, leucovorin, gemcitabine, regorafinib or erlotinib hydrochloride.

In some embodiments, an anti-CD47, anti-PD-L1, or CD47/PD-L1 bispecific antibody therapy may be co-administered with, or be sequentially administered before or after the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an anti-CD47 antibody, anti-PD-L1 antibody, or CD47/PD-L1 bispecific antibody therapy composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

Kits

A further aspect of the invention is a kit comprising an anti-CD47 antibody, anti-PD-L1 antibody, or CD47/PD-L1 bispecific antibody as disclosed herein above and instructions for use in accordance with any of the methods of the invention described herein. Generally, these instructions comprise a description of administration of the anti-CD47 antibody, anti-PD-L1 antibody, or CD47/PD-L1 bispecific antibody for the above described therapeutic treatments. This kit comprises any pharmaceutical composition disclosed herein. The pharmaceutical compositions and other reagents may be present in the kits in any convenient form, such as, e.g., in a solution or in a powder form.

In another aspect, a kit further comprises one or more other prophylactic or therapeutic agents useful for the treatment of cancer, in one or more containers. In one embodiment, the other prophylactic or therapeutic agent is a chemotherapeutic. In other aspects, the prophylactic or therapeutic agent is a biological or hormonal therapeutic.

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans.

Toxicity and efficacy of the prophylactic and/or therapeutic protocols of the instant invention may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Prophylactic and/or therapeutic agents that exhibit large therapeutic indices are preferred.

Further, any assays known to those skilled in the art may be used to evaluate the prophylactic and/or therapeutic utility of the therapies or combinatorial therapies disclosed herein for treatment or prevention of cancer.

The instructions relating to the use of the anti-CD47 antibody, anti-PD-L1 antibody, or CD47/PD-L1 bispecific antibody as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, ampules, tubes, bottles, jars, flexible packaging (e.g., sealed Mylar or plastic bags), and the like for each pharmaceutical composition and other included reagents, e.g., buffers, balanced salt solutions, etc., for use in administering the pharmaceutical compositions to subjects. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CD47 antibody, anti-PD-L1 antibody, or CD47/PD-L1 bispecific antibody. The container may further comprise a second pharmaceutically active agent.

Normally, the kit comprises a container and a label or package insert(s) on or associated with the container.

Incorporated by reference herein for all purposes is the content of U.S. Provisional Patent Application Nos. 62/949,120 (filed Dec. 17, 2019) and 63/110,693 (Filed Nov. 6, 2020).

Biological Deposits

Representative materials of the present invention were deposited in the American Type Culture Collection, 10801 University Boulevard, Manassas, Va. 20110-2209, USA, on 8 Dec. 2020. Vector "CD47_P01A11_75 Heavy Chain" having ATCC Accession No. PTA-126910 comprises a DNA insert encoding the anti-CD47 heavy chain designated "CD47_P01A11_75 Heavy Chain", vector "PDL1_P06B05_245 Heavy Chain" having ATCC Accession No. PTA-126911 comprises a DNA insert encoding the anti-PD-L1 heavy chain designated "PDL1_P06B05_245 Heavy Chain", and vector "Common Light Chain 1 Full Light Chain" having ATCC Accession No. PTA-126912 comprises a DNA insert encoding the anti-CD47 and anti-PD-L1 common light chain designated "Common Light Chain 1 Full Light Chain".

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions; the materials will be promptly replaced on notification with another of the same. Availability of the deposited material is not to be construed as a license to practice the invention in contravention of the rights granted under the authority of any government in accordance with its patent laws.

The following examples of specific aspects for carrying out the present invention are offered for illustrative purposes only, and are not intended to limit the scope of the present invention in any way.

EXAMPLES

Example 1: Exemplary Anti-CD47 Antibodies

Provided below is information about the anti-CD47 common light chain (CLC) antibodies P14D04, P01A11, P01A08, and variants thereof. P14D04 has the light chain amino acid sequence shown in SEQ ID NO: 6. P01A11 and P01A08 have the light chain amino acid sequence shown in SEQ ID NO: 2.

TABLE 9

Summary of sequence properties of exemplary anti-CD47 CLC antibodies

| Antibody | Germ VH Line | Germ VL Line | VH CDR1 | VH CDR2 | VH CDR3 | VH CDR3 Length |
|---|---|---|---|---|---|---|
| P14D04 | IGHV3-23 | IGKV1-39 | GFSFSTFTMN (SEQ ID NO: 33) | TISGTGGNTYYADSVKG (SEQ ID NO: 35) | RRSTVGSNGHSYWFDY (SEQ ID NO: 36) | 16 |
| P01A11 | IGHV1-69 | IGLV1-47 | GYTFTNYAIS (SEQ ID NO: 27) | GISPLFGTANYAQKFQG (SEQ ID NO: 29) | DGGRSSDVGWYVGAMDV (SEQ ID NO: 30) | 17 |
| P01A08 | IGHV1-69 | IGLV1-47 | GYTFSNYAIT (SEQ ID NO: 39) | GISPIFGTANYAQKFQG (SEQ ID NO: 17) | DGGRSSDGGWRGAGMDY (SEQ ID NO: 40) | 17 |

TABLE 10

Summary of Binding Properties of Exemplary Anti-CD47 CLC Antibodies

| Antibody | $K_D$ (human), nM | $T_{1/2}$ (human), min | $K_D$ (cyno), nM | $T_{1/2}$ (cyno), min | Cross-react with mouse | SIRPα Blocking |
|---|---|---|---|---|---|---|
| P14D04 | 6.39 | 3.6 | 9.7 | 2.52 | No | Yes |
| P01A11 | 0.817 | 24.1 | 1.02 | 21.15 | Yes (>6.8 µM) | Yes |
| P01A08 | 1.72 | 21.31 | 2.08 | 20.16 | No | Yes |

Table 11A below summarizes properties of two additional anti-CD47 CLC antibodies.

TABLE 11A

Summary of Properties of Exemplary Anti-CD47 CLC Antibodies

| Sample | CDR H1 | CDR H2 | CDR H3 | $T_{1/2}$ human, min | $K_D$ human, nM | $T_{1/2}$ cyno, min | $K_D$ cyno, nM |
|---|---|---|---|---|---|---|---|
| P01A11_497 | GGTFT SYAIS (SEQ ID NO: 23) | GISPIFG TANYAQ KFQG (SEQ ID NO: 17) | DAGRSSDVG WYVGALDV (SEQ ID NO: 24) | NA | 497.0 | NA | 704.0 |
| P01A11_75 | GYTFS SYAIS (SEQ ID NO: 15) | GISPIFG TANYAQ KFQG (SEQ ID NO: 17) | DAGRSSDVG WYVGAIDV (SEQ ID NO: 18) | 0.49 | 75.0 | 0.48 | 104.8 |

Table 11B provides variants of the parental P01A11 antibody, and $K_D$ data for the binding of the variants to human CD47 ("hCD47") and cynomolgus CD47 ("cyCD47") proteins. The amino acid numbering in Table 11B is with reference to the CD47_P01A11_parent VH amino acid sequence (SEQ ID NO: 7). For example, "Y27G" refers to "Y" residue at position 27 of SEQ ID NO: 7, and indicates that the Y residue is mutated to a "G" residue. As shown in Table 11B, various variants of P01A11 that have mutations at positions 27, 30, 31, 53, 54, 55, 100, 105, 108 bind to hCD47 with a $K_D$ of less than 50 nM, and mutations at multiple positions can also be combined. Positions 27, 30, and 31 are in CDR1, positions 50, 52, 53, 54, and 55 are in CDR2, and positions 99, 100, 105, 108, 113, and 114 are in CDR3.

TABLE 11B

Muteins of P01A11

| Anti-CD47 Antibody Variant | hCD47 $K_D$ (nM) | cyCD47 $K_D$ (nM) |
|---|---|---|
| P01A11_wt | 1.3 | 1.3 |
| P1A11_Y27G | 20 | 23 |
| P1A11_T30S | 1.8 | 2.5 |
| P1A11_N31S | 7.0 | 9.3 |
| P1A11_G50R | >1500 | >1500 |
| P1A11_S52I | 1311 | >1500 |
| P01A11_P53G | 5.6 | 7.6 |
| P1A11_L54I | 0.69 | 1.3 |
| P1A11_F55L | 2.7 | 3.3 |
| P1A11_D99E | 1196 | >1500 |
| P1A11_G100A | 8.5 | 11 |
| P1A11_G100S | 28 | 36 |
| P1A11_G100Q | >1500 | >1500 |
| P01A11_G100V | >1500 | >1500 |
| P01A11_D105E | 48 | 62 |
| P1A11_W108Y | 25 | 32 |
| P1A11_W108F | 103 | 117 |
| P1A11_W108A | 608 | 773 |
| P1A11_M113L | 0.86 | 1.2 |
| P1A11_M113I | 2.9 | 3.7 |
| P01A11_P53G_D105E | 241.0 | 351.0 |
| P01A11_P53G_D114E | 300 | 520 |
| P01A11_L54A_D114E | 31 | 46 |
| P01A11_L54A_R102A | 38 | 45 |
| P01A11_L54A_S104E | 19 | 16 |
| P01A11_Y27G_L54I_G100A | 132 | 180 |
| P01A11_Y27G_L54I_G100A_M113L | 154 | 198 |
| P01A11_Y27G_L54I_G100A_M113I | 263 | 371 |
| P01A11_Y27G_N31S_L54I_G100A_M113L | 497 | 704 |
| P01A11_T30S_N31S_L54I_G100A | 97 | 138 |
| P01A11_T30S_N31S_L54I_G100A_M113L | 106 | 120 |
| P01A11_T30S_N31S_L54I_G100A_M113I | 75 | 105 |
| P01A11_T30S_N31S_L54I_G100A_W108Y_M113L | >1500 | >1500 |

Example 2: Exemplary Anti-PD-L1 Antibodies

Provided below is information about the anti-PD-L1 common light chain (CLC) antibodies P04D09, P06B05, and P06A09, and variants thereof. P04D09 has the light chain amino acid sequence as shown in SEQ ID NO: 6. P06B05 and P06A09 have the light chain amino acid sequence as shown in SEQ ID NO: 2.

TABLE 13

Summary of Sequence Properties of Exemplary Anti-PD-L1 CLC Antibodies

| Antibody | Germ Line VH | Germ Line VL | VH CDR1 | VH CDR2 | VH CDR3 | VH CDR3 Length |
|---|---|---|---|---|---|---|
| P04D09 | IGHV3-23 | IGKV1-39 | GFTFSSYAMS (SEQ ID NO: 49) | AIGVRGGITYYADSVKG (SEQ ID NO: 51) | ERSVGELVGIDWMDH (SEQ ID NO: 56) | 15 |
| P06B05 | IGHV3-15 | IGLV1-47 | GFTFSNAWMN (SEQ ID NO: 43) | RIKTKADGGTTDYAAPVKG (SEQ ID NO: 45) | DPGSYWDSVYGGMDY (SEQ ID NO: 57) | 15 |
| P06A09 | IGHV3-15 | IGLV1-47 | GFTFSNAWMN (SEQ ID NO: 43) | RIKSESDGGTTDYAAPVKG (SEQ ID NO: 59) | DYRIDDWGYPYPGMDY (SEQ ID NO: 60) | 16 |

TABLE 14

Summary of Binding Properties of Exemplary Anti-PD-L1 CLC Antibodies

| Antibody | $K_D$ (human), nM | $T_{1/2}$ (human), min | $K_D$ (cyno), nM | $T_{1/2}$ (cyno), min | Cross with mouse? | PD-1 Blocking? |
|---|---|---|---|---|---|---|
| P04D09 | 0.56 | 43.6 | 1.15 | 20.1 | Y (20.4 nM) | Yes |
| P06B05 | 4.42 | 28.2 | 8.07 | 10.2 | Y (207 nM) | Yes |
| P06A09 | 2.97 | 5.13 | 5.75 | 2.79 | Y (113 nM) | Yes |

The properties of two additional anti-PD-L1 antibodies, P04D09_113 and P06B05_245, are summarized in Table 15A below.

TABLE 15A

Summary of Properties of Exemplary Anti-PD-L1 CLC Antibodies

| Sample | CDR H1 | CDR H2 | CDR H3 | $T_{1/2}$ human, min | $K_D$ human, nM | $T_{1/2}$ cyno, min | $K_D$ cyno, nM |
|---|---|---|---|---|---|---|---|
| P04D09_113 | GFTFSSYAMS (SEQ ID NO: 49) | AIGVRGGITYYADSVKG (SEQ ID NO: 51) | ERSVGELVGIDWMDH (SEQ ID NO: 56) | 22.2 | 1.7 | 23.4 | 1.7 |
| P06B05_245 | GFTFSNAWMN (SEQ ID NO: 43) | RIKTKADGGTTDYAAPVKG (SEQ ID NO: 45) | DPGEYWDSVYGGMDY (SEQ ID NO: 46) | 23.4 | 1.6 | 23.7 | 1.6 |

Table 15B provides additional variants of the parental P06B05 clone, and $K_D$ data for the binding of the muteins to human PD-L1 ("hPD-L1"), cynomolgus PD-L1 ("cyPD-L1"), and mouse PD-L1 ("mPD-L1") proteins. The amino acid numbering in Table 15B is with reference to the PDL1_P06B05_parent VH amino acid sequence (SEQ ID NO: 11). For example, "S104A" refers to "S" residue at position 104 of SEQ ID NO: 11, and indicates that the "S" residue is mutated to an "A" residue. As shown in Table 15B, various variants of P06B05 that have mutations at positions 103, 104, 105, 107, 112, 113, 61, and 62 bind to hPD-L1 with a $K_D$ of less than 50 nM, and mutations at multiple positions can also be combined. Positions 56, 57, 61, and 62 are in CDR2, and positions 103, 104, 105, 107, 109, 112, and 113 are in CDR3.

| Anti-PD-L1 Antibody Variant | hPD-L1 $K_D$ (nM) | cyPD-L1 $K_D$ (nM) | mPD-L1 $K_D$ (nM) |
| --- | --- | --- | --- |
| P06B05_parent | 2.36 | 3.11 | ND |
| P06B05_G103I | 8.06 | 8.11 | ND |
| P06B05_S104A | 3.50 | 3.93 | ND |
| P06B05_S104H | 7.90 | 6.11 | ND |
| P06B05_S104Y | 9.75 | 5.79 | ND |
| P06B05_S104E | 0.80 | 0.45 | 23.1 |
| P06B05_S104I | <0.74 | 0.99 | ND |
| P06B05_Y105H | 12.8 | 6.58 | ND |
| P06B05_D107S | 23.9 | 26.3 | ND |
| P06B05_D107L | 90.2 | 83.0 | ND |
| P06B05_D107Y | 3.03 | 3.23 | ND |
| P06B05_V109S | 76.5 | >100 | ND |
| P06B05_G112A | 3.71 | 3.72 | 131 |
| P06B05_G112S | 1.69 | 1.74 | 77.7 |
| P06B05_M113L | 6.82 | 6.55 | ND |
| P06B05_D56E_G57E | 69.7 | 60.6 | ND |
| P06B05_D56E_G57A | 95.5 | 92.2 | >1500 |
| P06B05_D61Q_Y62E | 5.81 | 4.43 | ND |
| P06B05_D61Q_Y62S | 5.02 | 5.54 | ND |
| P06B05_D61E_Y62E | 9.49 | 8.39 | ND |
| P06B05_D61A_Y62Q | 5.97 | 4.96 | ND |
| P06B05_D61A_Y62E | 3.28 | 3.17 | ND |
| P06B05_D61A_Y62A | 4.01 | 3.67 | ND |
| P06B05_D61A_Y62S | 5.37 | 2.75 | ND |
| P06B05_D61S_Y62Q | 5.98 | 3.73 | ND |
| P06B05_D61S_Y62A | 6.71 | <1.19 | ND |
| P06B05_D61S_Y62S | 6.10 | 2.15 | ND |

Example 3: Preparation of Exemplary CD47/PD-L1 Bispecific Antibodies

Various CD47/PD-L1 bispecific antibodies were prepared by combining certain anti-CD47 and anti-PD-L1 antibodies described above into bispecific format.

CD47/PD-L1 bispecific antibody 1 (also referred to herein as "BsAb1") was prepared by combining the anti-CD47 antibody P01A11_75 (VH amino acid sequence shown in SEQ ID NO: 1) with the anti-PD-L1 antibody P06B05_245 (VH amino acid sequence shown in SEQ ID NO: 4) into a bispecific antibody format. These two antibodies both have the same light VL amino acid sequence (shown in SEQ ID NO: 2), and accordingly anti-CD47/anti-PD-L1 BsAb1 has the same light chain amino acid sequence for both the anti-CD47 variable region and the anti-PD-L1 variable region (i.e. a common light chain). BsAb1 has a human IgG1 Fc domain, with knob-in-hole mutations. IgG1 was selected for robust effector function, including ADCP and ADCC as part of the mechanism of action of the antibody to drive anti-tumor efficacy (in addition to the innate and adaptive checkpoint blockade). The amino acid sequences of the anti-CD47 heavy chain, the anti-PD-L1 heavy chain, and the common light chain of BsAb1 are shown in Table 16 below. Mutations in the Fc chain in each chain to generate either a "knob" or "hole" structure are underlined.

A CD47/PD-L1 bispecific antibody that is identical to BsAb1, except for the addition of a "GGGGS" (SEQ ID NO: 75) linker followed by 6× histidine tag to the C-terminus of the knob anti-PD-L1 heavy chain ("GGGGSHHHHHH") (SEQ ID NO: 76) was also prepared. This antibody has the essentially the same binding affinity to CD47 and PD-L1 and other properties as the untagged version of BsAb1, and was used for most of the experiments involving BsAb1 provided herein.

TABLE 16

Amino Acid Sequences of BsAb1

| Polypeptide | Amino Acid Sequence |
| --- | --- |
| Anti-CD47 heavy chain (with "hole" mutations in Fc chain) | QVQLVQSGAEVKKPGSSVKVSCKASGYTFSSYAISWVRQAPGQGL EWMGGISPIFGTANYAQKFQGRVTITADESTSTAYMELSSLRSEDTA VYYCARDAGRSSDVGWYVGAIDVWGQGTLVTVSSASTKGPSVFPL APSSKSTSGGTAALGCLVKDYFPEPVTVSWNSGALTSGVHTFPAVL QSSGLYSLSSVVTVPSSSLGTQTYICNVNHKPSNTKVDKKVEPKSC DKTHTCPPCPAPELLGGPSVFLFPPKPKDTLMISRTPEVTCVVVDVS HEDPEVKFNWYVDGVEVHNAKTKPREEQYNSTYRVVSVLTVLHQD WLNGKEYKCKVSNKALPAPIEKTISKAKGQPREPQVYTLPP<u>C</u>REEM TKNQVSL<u>SC</u>AVKGFYPSDIAVEWESNGQPENNYKTTPPVLDSDGSF FL<u>V</u>SKLTVDKSRWQQGNVFSCSVMHEALHNHYTQKSLSLSPGK (SEQ ID NO: 61) |
| Anti-PD-L1 heavy chain (with "knob" mutations in Fc chain) | EVQLVESGGGLVKPGGSLRLSCAASGFTFSNAWMNWVRQAPGKG LEVWGRIKTKADGGTTDYAAPVKGRFTISRDDSKNTLYLQMNSLKTE DTAVYYCTTDPGEYWDSVYGGMDYWGQGTLVTVSSASTKGPSVF PLAPSSKSTSGGTAALGCLVKDYFPEPVTVSWNSGALTSGVHTFPA VLQSSGLYSLSSVVTVPSSSLGTQTYICNVNHKPSNTKVDKKVEPKS CDKTHTCPPCPAPELLGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQV<u>C</u>TLPPSREE MTKNQVSL<u>W</u>CLVKGFYPSDIAVEWESNGQPENNYKTTPPVLDSDG SFFLYSKLTVDKSRWQQGNVFSCSVMHEALHNHYTQKSLSLSPGK (SEQ ID NO: 64) |

TABLE 16-continued

Amino Acid Sequences of BsAb1

| Polypeptide | Amino Acid Sequence |
|---|---|
| Common light chain | QSVLTQPPSASGTPGQRVTISCSGSSSNIGSNYVYWYQQLPGTAPK LLIYRNNQRPSGVPDRFSGSKSGTSASLAISGLRSEDEADYYCAAW DDSLSGWFGGGTKLTVLGQPKAAPSVTLFPPSSEELQANKATLVCL ISDFYPGAVTVAWKADSSPVKAGVETTTPSKQSNNKYAASSYLSLTP EQWKSHRSYSCQVTHEGSTVEKTVAPTECS (SEQ ID NO: 62) |

CD47/PD-L1 bispecific antibody 2 (also referred to herein as "BsAb2") was prepared by combining the anti-CD47 antibody P01A11_497 (VH amino acid sequence shown in SEQ ID NO: 3) with the anti-PD-L1 antibody P06B05_245 (VH amino acid sequence shown in SEQ ID NO: 4). These two antibodies both have the same light VL amino acid sequence (shown in SEQ ID NO: 2), and accordingly BsAb2 has the same light chain amino acid sequence for both the anti-CD47 variable region and the anti-PD-L1 variable region (i.e. a common light chain). BsAb2 has a human IgG1 Fc domain, with knob-in-hole mutations. The amino acid sequences of the anti-CD47 heavy chain, the anti-PD-L1 heavy chain, and the common light chain of BsAb2 are shown in Table 17 below. Mutations in the Fc chain to generate either a "knob" or "hole" structure are underlined.

A CD47/PD-L1 bispecific antibody that is identical to BsAb2, except for the addition of a "GGGGS" (SEQ ID NO: 75) linker followed by 6× histidine tag to the C-terminus of the knob anti-PD-L1 heavy chain ("GGGGSHHHHHH") (SEQ ID NO: 76) was also prepared. This antibody has the essentially the same binding affinity to CD47 and PD-L1 and other properties as the untagged version of BsAb2, and was used for most of the experiments involving BsAb2 provided herein.

TABLE 17

Amino Acid Sequences of BsAb2

| Polypeptide | Amino Acid Sequence |
|---|---|
| Anti-CD47 heavy chain (with "hole" mutations in Fc chain) | QVQLVQSGAEVKKPGSSVKVSCKASGGTFTSYAISWVRQAPGQGL EWMGGISPIFGTANYAQKFQGRVTITADESTSTAYMELSSLRSEDTA VYYCARDAGRSSDVGWYVGALDVWGQGTLVTVSSASTKGPSVFP LAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYN STYRVVSVLTVLHQDWLNGKEYKCKVSNKALPAPIEKTISKAK GQPREPQVYTLPPCREEMTKNQVSLSCAVKGFYPSDIAVEWE SNGQPENNYKTTPPVLDSDGSFFLVSKLTVDKSRWQQGNVFS CSVMHEALHNHYTQKSLSLSPGK (SEQ ID NO: 63) |
| Anti-PD-L1 heavy chain (with "knob" mutations in Fc chain) | EVQLVESGGGLVKPGGSLRLSCAASGFTFSNAWMNWVRQAPGKG LEWVGRIKTKADGGTTDYAAPVKGRFTISRDDSKNTLYLQMNSLKTE DTAVYYCTTDPGEYWDSVYGGMDYWGQGTLVTVSSASTKGPSVF PLAPSSKSTSGGTAALGCLVKDYFPEPVTVSWNSGALTSGVHTFPA VLQSSGLYSLSSVVTVPSSSLGTQTYICNVNHKPSNTKVDKKVEPKS CDKTHTCPPCPAPELLGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVCTLPPSREE MTKNQVSLWCLVKGFYPSDIAVEWESNGQPENNYKTTPPVLDSDG SFFLYSKLTVDKSRWQQGNVFSCSVMHEALHNHYTQKSLSLSPGK (SEQ ID NO: 64) |
| Common light chain | QSVLTQPPSASGTPGQRVTISCSGSSSNIGSNYVYWYQQLPGTAPK LLIYRNNQRPSGVPDRFSGSKSGTSASLAISGLRSEDEADYYCAAW DDSLSGVVFGGGTKLTVLGQPKAAPSVTLFPPSSEELQANKATLVCL ISDFYPGAVTVAWKADSSPVKAGVETTTPSKQSNNKYAASSYLSLTP EQWKSHRSYSCQVTHEGSTVEKTVAPTECS (SEQ ID NO: 62) |

CD47/PD-L1 bispecific antibodies BsAb1 and BsAb2 were each prepared by transfecting a CHO cell with polynucleotides containing nucleic acid sequences encoding 3 separate polypeptides: the respective anti-CD47 heavy chain; the anti-PD-L1 heavy chain, and the common light chain. The respective CD47/PD-L1 bispecific antibodies were expressed in these cells, and purified via column chromatography. Thus, of note, the CD47/PD-L1 bispecific antibodies are significantly easier to produce than many other types and formats of bispecific antibody, as the CD47/PD-L1 bispecific antibodies provided herein can be produced and purified in a similar manner to standard IgG mAbs. The main difference with the bispecific antibody provided herein as compared to a standard IgG mAb is that for a standard IgG mAb, the host cell is transfected with polynucleotides encoding two polypeptide chains [i.e. i) the mAb heavy chain and i) the mAb light chain], whereas for the CD47/PD-L1 bispecific mAb provided herein, the host cell is transfected with polynucleotides encoding three polypeptide chains [i.e. i) the anti-CD47 heavy chain, ii) the anti-PD-L1 heavy chain, and iii) the common light chain].

A mouse surrogate CD47/PD-L1 bispecific antibody was prepared using antibodies selected for binding to mouse CD47 and mouse PD-L1 proteins, referred to herein as "BsAb3".

Example 4: Binding Affinity of CD47/PD-L1 Bispecific Antibodies to CD47 and PD-L1 Proteins CD47/PD-L1 BsAb1, BsAb2, and BsAb3 (described in Example 3 above) were assessed for binding affinities to human, cynomolgus monkey, and mouse CD47 and PD-L1 proteins. The affinities are summarized in Table 18 below.

TABLE 18

Binding Affinity of BsAb1, BsAb2, and BsAb3 to Various Proteins

| Anti-CD47/anti-PD-L1 Bispecific mAb: | Human CD47 $K_D$ (nM) | CD47 $K_D$ (nM) | CD47 $K_D$ (nM) | PD-L1 $K_D$ (nM) | PD-L1 $K_D$ (nM) | PD-L1 $K_D$ (nM) |
|---|---|---|---|---|---|---|
| BsAb1 | 75, 82* | 99 | >6800 | 0.21 | 0.21 | ND |
| BsAb2 | 496 | 638 | >6800 | 0.21 | 0.21 | ND |
| BsAb3 | ND | ND | 14 | ND | ND | 1.84 |

* = two independent measurements; "ND" = no data.

Binding of BsAb1, BsAb2, a positive control antibody (anti-CD47 antibody P01A11_75) and a negative control antibody (anti-PD-L1 antibody P06B05_245) to human CD47 on the cell surface was evaluated by flow cytometry using CHO cells generated to stably overexpress human CD47. The resulting EC50 values (i.e. the concentration at which 50% of the CD47 proteins are bound by the antibody) were: BsAb1: 11.8 nM; BsAb2: 101.2 nM; antibody P01A11_75: 0.98 nM; and antibody P06B05_245: not applicable (N/A).

Binding of BsAb1 and BsAb2 to human PD-L1 on the cell surface was evaluated by flow cytometry using CHO cells generated to ectopically overexpress human PD-L1. The resulting EC50 values (i.e. the concentration at which 50% of the PD-L1 proteins are bound by the antibody) were: BsAb1: 0.38 nM and BsAb2: 0.24 nM.

Example 5: Binding of CD47/PD-L1 Bispecific Antibodies to Tumor Cells and Red-Blood Cells A potential advantage of a CD47/PD-L1 bispecific antibody as compared to an anti-CD47 monospecific antibody is that an a CD47/PD-L1 bispecific antibody potentially has greater selectivity towards tumor cells and/or immune cells in a tumor microenvironment (both of which may co-express CD47 and PD-L1) as compared to blood cells (e.g. red blood cells) that only express CD47. By potentially having greater selectively than an anti-CD47 monospecific antibody for cells in a tumor microenvironment, a CD47/PD-L1 bispecific antibody potentially has reduced toxicity as compared to an anti-CD47 monospecific antibody.

Binding of BsAb1 and BsAb2 to human CD47 was compared to that of the monospecific anti-CD47 mAbs 5F9 [Liu, J et al., PLoS One. 2015; 10(9)] and 2A1 (US Pub. No. 20140140989) in a mixture consisting of tumor cells (i.e. HT1080 cells that have both CD47 and PD-L1 expression) with red blood cells (RBCs) (only CD47 expression) at 1:10 ratio. The EC50 of anti-CD47 5F9 and 2A1 binding to tumor and RBCs are both less than 0.1 nM with no selectivity. In contrast, both BsAb1 and BsAb2 bound 100% of tumor cells at <0.1 nM but the EC50 for RBC binding was >10 nM, suggesting at least 100 fold selectivity for tumor cells vs RBCs.

Example 6: Blocking Activity of CD47/PD-L1 Bispecific Antibodies on CD47-SIRPa and PD-L1-PD-1 Interaction This example illustrates the blocking ability of BsAb1 and BsAb2.

A cell-based SIRPa blocking IC50 assay to test the impact of BsAb1 and BsAb2 on SIRPa protein binding to human CD47 overexpressed by a CHO cell ("CHO-hCD47") was conducted. Similarly, a cell-based SIRPa blocking IC50 assay to test the impact of BsAb3 on SIRPa protein binding to mouse CD47 overexpressed by a CHO cell ("CHO-mouseCD47") was conducted. The results of this assay are shown in Table 19 below.

In addition, a cell-based PD-1 blocking IC50 assay to test the impact of BsAb1 and BsAb2 on PD-1 protein binding to human PD-L1 overexpressed by a CHO cell ("CHO-hPD-L1") was conducted. Specifically, for PD-L1 blocking activity, the PD-1/PD-L1 interaction inhibits TCR-mediated luminescence when coculturing PD-L1 aAPC/CHO-K1 with PD-1 effector cells via the kit (Promega #J1250). When the PD-1/PD-L1 interaction is disrupted by PD-1 blocking mAbs, TCR activation induces luminescence via activation of the NFAT pathway. A similar cell-based PD-1 blocking IC50 assay to test the impact of bispecific BsAb3 on PD-1 protein binding to mouse PD-L1 overexpressed by a CHO cell ("CHO-mousePD-L1") was also conducted. The results of this assay are also shown in Table 19 below.

TABLE 19

Blocking activity of CD47/PD-L1 bispecific antibodies

| Anti-CD47/anti-PD-L1 Bispecific mAb: | Blocking/Non-blocking SIRPa | Blocking/Non-blocking PD-1 |
|---|---|---|
| BsAb1 | blocking, IC50 = 114 nM | blocking |
| BsAb2 | blocking, IC50 = 3693 nM | blocking |
| BsAb3 | blocking, IC50 = 115.2 nM | blocking |

As shown in Table 19, each of BsAb1, BsAb2, and BsAb3 blocked the interaction between SIRPα and CD47. In addition, each of BsAb1, BsAb2, and BsAb3 blocked the interaction between PD-1 and PD-L1.

Example 7: Antibody-Dependent Cellular Phagocytosis (ADCP) Potentiating Activity of CD47/PD-L1 Bispecific Antibodies ADCP Assay To test the antibody-dependent cellular phagocytosis (ADCP) activity, human macrophages were differentiated from monocytes isolated from PBMC from two donors and co-cultured with tumor cells expressing both CD47 and PD-L1 (NCI-H292 cells; pulmonary mucoepidermoid carcinoma) in the presence of the bispecific CD47/PD-L1 BsAb1. As shown in FIG. 1, the treatment with BsAb1 potentiated macrophage phagocytosis on human target cells NCI-H292, which have both CD47 and PD-L1 expression. In addition, as shown in FIG. 1, BsAb1 is more effective than either an anti-CD47 monospecific antibody (P01A11_75) or an anti-PD-L1 monospecific antibody (P06605_245) at potentiating phagocytosis of the tumor cells. For example, at 0.32 nM concentration, the phagocytosis % of total tumor cells for BsAb1 is nearly 60%, whereas for both anti-CD47 monospecific antibody (P01A11_75) and anti-PD-L1 monospecific antibody (P06605_245), it is only around 30% (FIG. 1).

Example 8: In Vivo Efficacy Studies of Mouse Surrogate CD47/PD-L1 Bispecific Antibody This example illustrates the antitumor efficacy of CD47/PD-L1 bispecific antibodies in three syngeneic mouse tumor models [CT26—hot tumor model (mouse colon carcinoma cells); MC38—warm tumor model (mouse colon carcinoma cells); B16F10—cold tumor model (mouse melanoma cells)].

In the CT26 tumor model, the efficacy and body weight changes after treatment with CD47/PD-L1 bispecific antibody BsAb3 were compared to monospecific anti-mCD47 and monospecific anti-mPD-L1 mAbs alone, and in combination (FIGS. 2A, 2B, and 2C). In addition, an Fc-null version of BsAb3 was prepared and included in the experiment, to assess the contribution of Fc-mediated effector function to BsAb3 activity. Following intraperitoneal (IP) treatment at 100 μg (~5 mg/kg) for a total of three doses administered three or four days apart, the efficacy of the BsAb3 CD47/PD-L1 bispecific antibody was statistically better than anti-CD47 or anti-PD-L1 alone [FIG. 2A; BsAb3 (solid diamond) treatment resulted in the smallest tumor volume of any of the tested antibodies or antibody combinations]. Moreover, anti-CD47 mAb was not tolerated at this dose as evidenced by body weight loss (FIG. 2B), whereas BsAb3 was well tolerated throughout the treatment. [In FIG. 2B, the data points for anti-CD47 monospecific antibody (empty square) and anti-CD47 monospecific antibody in combination with anti-PD-L1 monospecific antibody (inverted empty triangle) largely overlap. Also, the data points for anti-PD-L1 monospecific antibody (solid triangle) and bispecific CD47/PD-L1 BsAb3 (solid diamond) largely overlap. Fc-null bispecific CD47/PD-L1 BsAb3 (empty circle) data is not present in FIG. 2B.] Treatment with BsAb3 resulted in tumor growth inhibition similar to that achieved with a combination of anti-CD47 and anti-PD-L1 mAbs, however, the combination of monospecific antibodies caused a >10% loss of body weight. Comparison of the efficacy of BsAb3 with and without IgG effector function showed a reduced efficacy with mG2a Fc-null as compared to mG2a wild-type (FIG. 2A and FIG. 2C). Among the tested compounds, treatment with the BsAb3 with mG2a wild-type effector function (solid diamond) resulted in the best survival outcomes (FIG. 2C). As shown in FIG. 2C, animals treated with BsAb3 with mG2a wild-type effector function (solid black diamond) had about 75% survival at 28 days post treatment. In contrast, animals treated with anti-CD47 monospecific antibody in combination with anti-PD-L1 monospecific antibody (inverted empty triangle) had about 65% survival at 28 days post treatment. Animals treated with BsAb3 with mG2a Fc-null (empty circle) had about 25% survival at 28 days post treatment.

In the MC38 tumor model, different doses of bispecific BsAb3 were assessed for efficacy at inhibiting the growth of the tumor. Mice bearing MC38 tumors were treated intraperitoneally with 10, 20, or 40 mg/kg BsAb3, twice per week for three weeks, for a total of 6 doses. In this model, the observed efficacy of the 10, 20, or 40 mg/kg treatments was ~25.7%, 52.6%, and 75.8% tumor growth inhibition (i.e. as compared to an isotype control antibody), respectively (FIG. 3A). All of these doses were well tolerated, with no body weight loss (FIG. 3B).

In the B16F19 tumor model, 20 mg/kg BsAb3 was assessed for anti-tumor efficacy. Mice bearing B16F19 tumors were treated intraperitoneally with 20 mg/kg bispecific BsAb3 three times per week for three weeks, for a total of 9 doses. In this model, the observed efficacy of the 20 mg/kg treatments was ~68% tumor growth inhibition (i.e. as compared to an isotype control antibody) (FIG. 4A). This dose was well tolerated, without a substantial loss in body weight (FIG. 4B).

Example 9: Mechanism of Action Studies of Mouse Surrogate CD47/PD-L1 Bispecific Antibody In this experiment, assays were performed to determine which immune cell type(s) are required for anti-tumor efficacy of the mouse surrogate CD47/PD-L1 bispecific antibody.

Figure 5C:
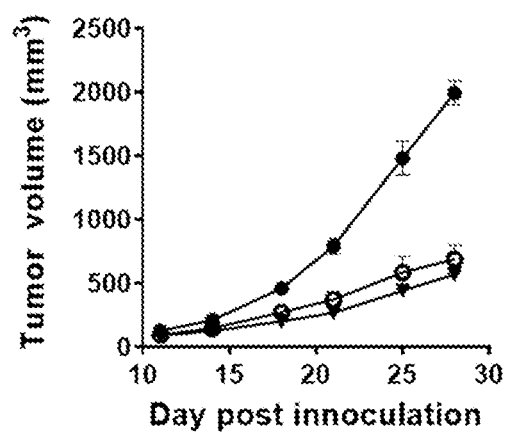
Figure 5D:
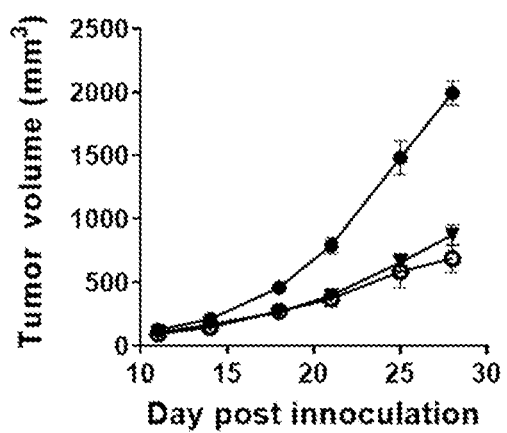

Antibodies known to deplete CD8 T cells (anti-CD8; Antibody: 2.43), CD4 T cells (anti-CD4; Antibody: GK1.5), NK cells (anti-NK1.1; Antibody: PK136), and tumor-associated macrophages (anti-CSF1R) were co-administered with the mouse CD47/PD-L1 bispecific BsAb3 (40 mg/kg, twice a week for three weeks) in mice bearing MC38 tumors. As shown in FIGS. 5A, 5C, and 5D, the data suggested the efficacy was compromised in the absence of CD8 T cells alone (FIG. 5A) and the combination of CD8 plus CD4 T cells (FIG. 5A), but not in the absence of CD4 T cells alone (FIG. 5A), in the absence of NK cells (FIG. 5D), or in the absence of tumor-associated macrophages (FIG. 5C). In addition, this study was also performed in BATF3−/− mice which lack classical type-1 dendritic cells (DC1) (CD8α+ and CD103+) subsets as compared to wild-type C57BL/6 mice (Hildner, K., et al., Science, 2008. 322(5904): p. 1097-100). As shown in FIG. 5B, the efficacy was lost in the absence of cDC1. [In FIG. 5B, the data points for wild-type mice treated with control antibody (solid circle), BATF3−/− mice treated with control antibody (empty square) and BATF3−/− mice treated with BsAb3 (solid triangle) closely overlap, particularly at day 25.]

Example 10: Pharmacodynamic Effects of CD47/PD-L1 Bispecific Antibody

The purpose of this experiment was to understand the pharmacodynamic effects of CD47/PD-L1 bispecific antibody in vivo.

Mice bearing MC38 tumors were treated with 5 mg/kg, 10 mg/kg, or 20 mg/kg of bispecific BsAb3 on days 11, 14, and 18 post tumor implantation. Three weeks post tumor implantation, the tumors and spleens were harvested from the mice, and analyzed for different cell types. As shown in Tables 20a-20e, there was a dose-dependent increase in some splenic dendritic cell (DC) subsets such as CD8+CD11c+ DCs (Table 20a). Moreover, the percentage of DEC205+ CD8+CD103+ DCs among CD11c+ were significantly increased in the spleen (Table 20b). In terms of tumors, there is an increase of T cells (Thy1.2+) (Table 20c) and CD8+ T cells (Table 20d) but not CD4+ T cells (Table 20e), suggesting both innate and adaptive immune cells were modulated after the treatment with bispecific BsAb3.

TABLE 20a

CD8+ DCs (% of CD11c) in spleen

| Group | Mean | SEM |
|---|---|---|
| Control | 29.84 | 4.80 |
| BsAb3_5 mg/kg | 26.32 | 3.50 |
| BsAb3_10 mg/kg | 52.50 | 4.02 |
| BsAb3_20 mg/kg | 60.80 | 1.53 |

TABLE 20b

CD103+ DCs (% of CD11c) in spleen

| Group | Mean | SEM |
|---|---|---|
| Control | 8.76 | 3.21 |
| BsAb3_5 mg/kg | 9.17 | 2.09 |
| BsAb3_10 mg/kg | 17.23 | 5.22 |
| BsAb3_20 mg/kg | 31.16 | 1.69 |

TABLE 20c

T cells (% of CD45) in tumor

| Group | Mean | SEM |
|---|---|---|
| Control | 19.08 | 2.49 |
| BsAb3_5 mg/kg | 33.02 | 2.57 |
| BsAb3_10 mg/kg | 39.12 | 3.83 |
| BsAb3_20 mg/kg | 41.02 | 3.19 |

TABLE 20d

CD8 T cells (% of CD45) in tumor

| Group | Mean | SEM |
|---|---|---|
| Control | 6.44 | 0.77 |
| BsAb3_5 mg/kg | 14.48 | 1.68 |
| BsAb3_10 mg/kg | 19.52 | 1.71 |
| BsAb3_20 mg/kg | 19.40 | 1.61 |

TABLE 20e

CD4 T cells (% of CD45) in tumor

| Group | Mean | SEM |
|---|---|---|
| Control | 8.79 | 1.46 |
| BsAb3_5 mg/kg | 14.00 | 0.78 |

TABLE 20e-continued

CD4 T cells (% of CD45) in tumor

| Group | Mean | SEM |
|---|---|---|
| BsAb3_10 mg/kg | 14.61 | 2.63 |
| BsAb3_20 mg/kg | 15.15 | 1.90 |

Example 11: In Vivo Efficacy Studies of CD47/PD-L1 BsAb1

The purpose of this experiment was to test the in vivo efficacy of the CD47/PD-L1 BsAb1 and BsAb2.

NSG immunodeficient mice were inoculated subcutaneously at the right flank with $2\times10^6$ MDA-MB-231 triple-negative human breast cancer cells. These cells endogenously overexpress both CD47 and PD-L1. When tumors reached the target size, mice were randomized into treatment groups. Treatment was started on the same day as randomization. Mice were treated with 10 mg/kg hIgG1 isotype mAb (control), or 1, 5, or 10 mg/kg of CD47/PD-L1 BsAb1 or BsAb2 once a week for 6 weeks. Tumor size was measured at various intervals in 2 dimensions using a caliper, and the volume was calculated in cubic millimeters using the formula: $V=0.5\ L\times W^2$, where L is the longest diameter of the tumor and W is the diameter perpendicular to L.

The results are shown in FIG. 6. As shown in FIG. 6, treatment with 5 or 10 mg/kg his-tagged CD47/PD-L1 BsAb1 or BsAb2 substantially delayed MDA-MB-231 tumor growth as compared to the isotype control. Specifically, for BsAb1, the tumor growth inhibition (TGI) as compared to the isotype antibody was 16.8%, 68.4%, and 78.7% at the 1 mg/kg, 5 mg/kg, and 10 mg/kg doses, respectively. For BsAb2, the tumor growth inhibition (TGI) as compared to the isotype antibody was 6.9%, 62.8%, and 74.1% at the 1 mg/kg, 5 mg/kg, and 10 mg/kg doses, respectively. [In FIG. 6, the data points for control isotype antibody (solid circle), 1 mg/kg BsAb1 (solid triangle), and 1 mg/kg BsAb2 (empty circle) generally are close to each other or overlap. Similar, the data points for 5 mg/kg BsAb1 (empty diamond), 10 mg/kg BsAb1 (empty triangle), 5 mg/kg BsAb2 (solid diamond), are 10 mg/kg BsAb2 (solid square) generally are close to each other, with 10 mg/kg BsAb1 having the lowest values.]

Example 11: Toxicity Studies of Anti-CD47/Anti-PD-L1 BsAb1 and BsAb2 in Cynomolgus Monkeys The purpose of this experiment was to perform exploratory toxicity studies (ETS) with his-tagged BsAb1 and his-tagged BsAb2 in cynomolgus monkeys. BsAb1 and BsAb2 have similar binding affinities for human and cynomolgus monkey CD47 and PD-L1 moieties, and bind to cynomolgus monkey red blood cells and platelets with similar affinity to human red blood cells and platelets. Accordingly, these data support the use of the cynomolgus monkey as a relevant species for toxicity assessments of CD47/PD-L1 BsAb1 and BsAb2.

For each of BsAb1 and BsAb2, one monkey was administered doses of 10 mg/kg, one monkey was administered doses of 30 mg/kg, and 3 monkeys were administered doses of 100 mg/kg. The mAbs were administered intravenously on Days 1 and 8. On Day 15, samples from each monkey were analyzed for various immune cell subsets and cytokines, as shown in Tables 21-24 below. Tables 21 and 23 provide data regarding activation and/or proliferation of various immune cell subsets following administration of different doses of BsAb1 or BsAb2 to monkeys. Tables 22 and 24 provide data regarding increase of various cytokines following administration of different doses of BsAb1 or BsAb2 to monkeys.

In the tables below, NC=no change; IL=interleukin; IFN=interferon; MCP=monocyte chemoattractant protein; IP=interferon-inducible protein. The ratios (e.g. "1/1" or "2/3") refer to the number of monkeys that experienced a change in the parameter over the total number of monkeys in the treatment group. For example "2/3" indicates that two out of the three monkeys in the treatment had a change in the relevant parameter. Values provided in parentheses [e.g. "(4.9x)"] provide the fold-change as compared to baseline; a range of values are provided in parentheses when there is data from two or more monkeys [e.g. "(4.0x-9.2x)"].

TABLE 21

Immune Cell Activation/Proliferation with CD47/PD-L1 BsAb1

|  | Vehicle | 10 mg/kg/ dose | 30 mg/kg/ dose | 100 mg/kg/ dose |
|---|---|---|---|---|
| % activated (CD69+) CD4+ T cells | (0.42x-1.63x) | 1/1 (2.64x) | 1/1 (3.20x) | 2/3 (2.86x-3.07x) |
| % activated (CD25+) CD8+ T cells | (0.52x-1.96x) | NC | 1/1 (3.61x) | 2/3 (4.01x-6.47x) |
| % proliferating (Ki-67+) CD4+ T cells | (1.00x-1.76x) | NC | NC | 3/3 (2.56x-3.28x) |
| % proliferating (Ki-67+) CD8+ T cells | (0.62x-2.94x) | NC | NC | 1/3 (6.46x) |
| % activated (CD83+) monocytes | (0.36x-1.82x) | NC | 1/1 (21.94x) | 3/3 (4.40x-39.40x) |

TABLE 22

Effect of CD47/PD-L1 BsAb1 on Cytokine Levels

|  | Vehicle | 10 mg/kg/ dose | 30 mg/kg/ dose | 100 mg/kg/ dose |
|---|---|---|---|---|
| IL-6 | (<1.0x-1.9x) | NC | 1/1 (4.9x) | 3/3 (4.0x-9.2x) |
| IFN-γ | (<1.0) | NC | NC | 1/3 (4.9x) |
| MCP-1/ CCL2 | (0.9x-2.7x) | NC | 1/1 (>4.8x) | 3/3 (4.4x-5.6x) |
| IP-10/ CXCL10 | (0.4x-1.0x) | NC | 1/1 (5.6x) | 2/3 (5.7x-7.2x) |

TABLE 23

Immune Cell Activation/Proliferation with CD47/PD-L1 BsAb2

|  | Vehicle | 10 mg/kg/ dose | 30 mg/kg/ dose | 100 mg/kg/ dose |
|---|---|---|---|---|
| % activated (CD69+) CD4+ T cells | (0.42x-1.63x) | 1/1 (4.07x) | NC | 3/3 (2.44x-6.21x) |
| % activated (CD25+) CD8+ T cells | (0.52x-1.96x) | NC | 1/1 (3.40x) | 1/3 (12.75x) |
| % proliferating (Ki-67+) CD4+ T cells | (1.00x-1.76x) | NC | 1/1 (3.29x) | 2/3 (2.26x-4.23x) |
| % proliferating (Ki-67+) CD8+ T cells | (0.62x-2.94x) | NC | 1/1 (4.68x) | NC |
| % activated (CD83+) monocytes | (0.36x-1.82x) | 1/1 (4.58x) | 1/1 (12.80x) | 2/3 (4.66x-6.80x) |

TABLE 24

Effect of CD47/PD-L1 BsAb2 on Cytokine Levels

|  | Vehicle | 10 mg/kg/ dose | 30 mg/kg/ dose | 100 mg/kg/ dose |
|---|---|---|---|---|
| IL-6 | (<1.0x-1.9x) | NC | 1/1 (4.4x) | 2/3 (7.8x-13.3x) |
| MCP-1/ CCL2 | (0.9x-2.7x) | NC | 1/1 (>3.6x) | 3/3 (3.3x->7.1x) |
| IP-10/ CXCL10 | (0.4x-1.0x) | NC | 1/1 (4.4x) | 1/3 (9.8x) |

As indicated in Tables 21 and 23, there was evidence of activation and/or proliferation of T cells and activation of monocytes in cyno monkeys administered BsAb1 and BsAb2. In addition, there was evidence of mild transient increase in monocyte/macrophage/DC or T cell-related cytokines including IL6, INFg, CCL2, CXCL10 as shown in Tables 22 and 24. Collectively, this data supports the pharmacological activity and activation of the immune system with anti-CD47/anti-PD-L1 BsAb1 and BsAb2 administration in the cynomolgus monkey.

Example 12: Combination Treatment: CD47/PD-L1 Bispecific mAb with a TLR9 Agonist This example illustrates the therapeutic activity of an anti-CD47/anti-PD-L1 mAb in combination with a TLR9 agonist.

The mouse surrogate CD47/PD-L1 bispecific BsAb3 is described above. Bispecific BsAb3 was administered at the sub-efficacious dose of 10 mg/kg in phosphate buffered saline (PBS) twice a week for two weeks (4 total doses).

The TLR9 agonist was CpG24555, which is a class B CpG oligonucleotide (ODN). CpG ODNs are synthetic ODNs that contain unmethylated CpG dinucleotides in specific sequence contexts (CpG motifs). CpG24555 is described, for example, in U.S. Pat. No. 8,552,165, which is hereby incorporated for all purposes. CpG24555 was dosed at 5 mg/kg, in phosphate buffered saline (PBS) (Life Technologies), intratumorally (it) for one dose, 11 days after tumor inoculation.

Six to eight week old female C57BL/6 mice were purchased from the Jackson Laboratories. All animals were housed in a pathogen free vivarium facility at Pfizer and experiments were conducted according to the protocols in accordance with the Institutional Animal Care and Use Committee (IACUC) guidelines.

The MC38 colon carcinoma cell line was purchased from American Type Culture Collection (ATCC). Pathogen-free cells growing in an exponential growth phase were harvested and used for tumor inoculation.

C57BL/6 mice were inoculated subcutaneously at the right flank with $0.5 \times 10^5$ MC38 cells in 0.1 mL of PBS. When tumors reached target size, mice were randomized into treatment groups. Treatment was started on the same day as randomization. Tumor size was measured at various intervals in 2 dimensions using a caliper, and the volume was calculated in cubic millimeters using the formula: $V=0.5\ L \times W^2$ where L is the longest diameter of the tumor and W is the diameter perpendicular to L. Body weight was also recorded.

Results are shown in FIG. 7. As shown in FIG. 7, both CD47/PD-L1 bispecific BsAb3 (empty square) and TLR9 agonist (solid inverted triangle) treatment delayed MC38 colon carcinoma tumor growth compared to isotype control (solid circle), and the combination of CD47/PD-L1 bispecific BsAb3 plus TLR9 agonist (empty triangle) had greater efficacy than the CD47/PD-L1 bispecific BsAb3 and TLR9 agents individually. [In FIG. 7, the data points for CD47/PD-L1 bispecific BsAb3 (empty square) and TLR9 agonist (solid inverted triangle) largely overlap.]

The increased efficacy observed with the combination treatment of CD47/PD-L1 bispecific mAb and TLR9 agonist is consistent with bulk tumor RNA sequencing data, which showed an increase in CD47 and PD-L1 expression in B16F10 tumor cells in response to intratumoral administration of TLR3, TLR7/8, TLR9, or STING agonists (data not shown).

Example 13: Combination Treatment: CD47/PD-L1 Bispecific mAb with a CDK 2/4/6 Inhibitor This example illustrates the therapeutic activity of a CD47/PD-L1 mAb in combination with a cyclin-dependent kinase (CDK) 2/4/6 inhibitor.

The mouse surrogate CD47/PD-L1 bispecific BsAb3 is described above. Bispecific BsAb3 was dosed at 20 mg/kg in phosphate buffered saline (PBS) three times a week for three weeks.

The CDK 2/4/6 inhibitor was PF-06873600. PF-06873600, or 6-(difluoromethyl)-8-((1R,2R)-2-hydroxy-2-methylcyclopentyl)-2-(1-(methylsulfonyl)piperidin-4-ylamino)pyrido[2,3-d]pyrimidin-7(8H)-one, is a potent and selective inhibitor of CDK2, CDK4 and CDK6, having the structure:

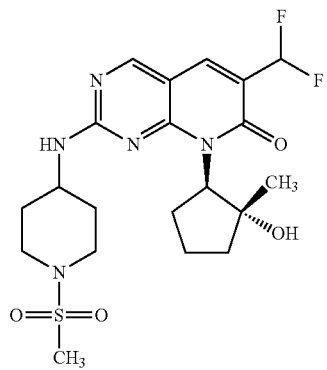 [SMILES: C[C@@]1(O)CCC[C@H]1n1c(=O)c(C(F)F)cc2cnc(NC3CCN(S(C)(=O)=O)CC3)nc21]

PF-06873600 and pharmaceutically acceptable salts thereof are disclosed in International Publication No. WO 2018/033815 published Feb. 22, 2018. The contents of that reference are incorporated herein by reference in their entirety.

Six to eight week old female C57BL/6 mice were purchased from the Jackson Laboratories. All animals were housed in a pathogen free vivarium facility at Pfizer and experiments were conducted according to the protocols in accordance with the Institutional Animal Care and Use Committee (IACUC) guidelines.

The B16F10 melanoma cell line was purchased from American Type Culture Collection (ATCC). Pathogen-free cells growing in an exponential growth phase were harvested and used for tumor inoculation.

C57BL/6 mice were inoculated subcutaneously at the right flank with $0.5 \times 10^5$ B16F10 cells in 0.1 mL of PBS. When tumors reached target size, mice were randomized into treatment groups. Treatment was started on the same day as randomization. Tumor size was measured at various intervals in 2 dimensions using a caliper, and the volume was calculated in cubic millimeters using the formula: $V=0.5\ L \times W^2$ where L is the longest diameter of the tumor and W is the diameter perpendicular to L. Body weight was also recorded.

Results are shown in FIG. 8. As shown in FIG. 8, both CD47/PD-L1 bispecific BsAb3 (solid triangle) and the CDK 2/4/6 inhibitor PF-06873600 (empty square) treatment delayed B16F10 melanoma tumor growth compared to isotype control (solid circle), and the combination of CD47/PD-L1 bispecific mAb and PF-06873600 (empty diamond) had greater efficacy than the CD47/PD-L1 bispecific mAb and PF-06873600 agents individually.

The increased efficacy observed with the combination treatment of CD47/PD-L1 bispecific mAb and CDK2/4/6 inhibitor is consistent with data which showed an increase in CD47 and PD-L1 expression on B16F10 tumor cells by flow cytometry in response to administration of PF-06873600 (data not shown).

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

In embodiments that refer to a method of treatment as described herein, such embodiments are also further embodiments for use in that treatment, or alternatively for the manufacture of a medicament for use in that treatment.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting. The term "or" when used in the context of a listing of multiple options (e.g. "A, B, or C") shall be interpreted to include any one or more of the options, unless the context clearly dictates otherwise.

Exemplary methods and materials are described herein, although methods and materials similar or equivalent to those described herein can also be used in the practice or testing of the present invention. The materials, methods, and examples are illustrative only and not intended to be limiting.

It is claimed:

1. An isolated antibody that specifically binds to CD47 and comprises a heavy chain variable region (VH) and a light chain variable region (VL), wherein the VH comprises (i) a VH complementarity determining region (CDR) 1 comprising the amino acid sequence of SEQ ID NO: 13, 14, or 15; (ii) a VH CDR2 comprising the amino acid sequence of SEQ ID NO: 16 or 17; (iii) a VH CDR3 comprising the amino acid sequence of SEQ ID NO: 18; (iv) a VL CDR1 comprising the amino acid sequence of SEQ ID NO: 19; (v) a VL CDR2 comprising the amino acid sequence of SEQ ID NO: 20; and (vi) a VL CDR3 comprising the amino acid sequence of SEQ ID NO: 21.

2. The antibody of claim 1, wherein the VH comprises the amino acid sequence of SEQ ID NO: 1.

3. The antibody of claim 1, wherein the VL comprises the amino acid sequence of SEQ ID NO: 2.

4. The antibody of claim 1, wherein the antibody comprises: a heavy chain variable region (VH) comprising the amino acid sequence as shown in SEQ ID NO: 1 and a light chain variable region (VL) comprising the amino acid sequence as shown in SEQ ID NO: 2.

5. An isolated antibody that specifically binds to PD-L1 and comprises a heavy chain variable region (VH) and a light chain variable region (VL), wherein the VH comprises (i) a VH complementarity determining region (CDR) 1 comprising the amino acid sequence of SEQ ID NO: 41, 42, or 43; (ii) a VH CDR2 comprising the amino acid sequence of SEQ ID NO: 44 or 45; and (iii) a VH CDR3 comprising the amino acid sequence of SEQ ID NO: 46; (iv) a VL CDR1 comprising the amino acid sequence of SEQ ID NO: 19; (v) a VL CDR2 comprising the amino acid sequence of SEQ ID NO: 20; and (vi) a VL CDR3 comprising the amino acid sequence of SEQ ID NO: 21.

6. The antibody of claim 5, wherein the VH comprises the sequence of SEQ ID NO: 4.

7. The antibody of claim 5, wherein the VL comprises the sequence of SEQ ID NO: 2.

8. The antibody of claim 5, wherein the antibody comprises: a heavy chain variable region (VH) comprising the amino acid sequence as shown in SEQ ID NO: 4 and a light chain variable region (VL) comprising the amino acid sequence as shown in SEQ ID NO: 2.

9. The antibody of claim 1, wherein the antibody is a bispecific antibody.

10. The antibody of claim 9, wherein the bispecific antibody specifically binds to CD47 and PD-L1.

11. The antibody of claim 10, wherein the antibody comprises a first antigen binding portion and a second antigen binding portion, wherein the first antigen binding portion specifically binds to CD47 and the second antigen binding portion specifically binds to PD-L1, wherein the first antigen binding portion comprises a first antigen binding portion VH and a first antigen binding portion VL, wherein the second antigen binding portion comprises a second antigen binding portion VH and a second antigen binding portion VL, and wherein the amino acid sequence of the first antigen binding portion VL and the amino acid sequence of the second antigen binding portion VL have the same amino acid sequence.

12. The antibody of claim 11, wherein the amino acid sequence of the first antigen binding portion VL and the amino acid sequence of the second antigen binding portion VL each comprise the amino acid sequence as shown in SEQ ID NO: 2.

13. An isolated bispecific antibody comprising a first antigen binding portion that specifically binds to CD47 and a second antigen binding portion that specifically binds to PD-L1, wherein the first antigen binding portion comprises a first antigen binding portion VH and a first antigen binding portion VL, wherein the second antigen binding portion comprises a second antigen binding portion VH and a second antigen binding portion VL, and wherein:
a) the first antigen binding portion VH comprises (i) a VH CDR1 comprising the amino acid sequence of SEQ ID NO: 13, 14, or 15; (ii) a VH CDR2 comprising the amino acid sequence of SEQ ID NO: 16 or 17; and (iii) a VH CDR3 comprising the amino acid sequence of SEQ ID NO: 18;
b) the first antigen binding portion VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21;
c) the second antigen binding portion VH comprises (i) a VH CDR1 comprising the amino acid sequence of SEQ ID NO: 41, 42, or 43; (ii) a VH CDR2 comprising the amino acid sequence of SEQ ID NO: 44 or 45; and (iii) a VH CDR3 comprising the amino acid sequence of SEQ ID NO: 46; and
d) the second antigen binding portion VL comprises (i) a VL CDR1 comprising the amino acid sequence of SEQ ID NO: 19; (ii) a VL CDR2 comprising the amino acid sequence of SEQ ID NO: 20; and (iii) a VL CDR3 comprising the amino acid sequence of SEQ ID NO: 21.

14. The bispecific antibody of claim 13, wherein:
a) the first antigen binding portion VH comprises the amino acid sequence of SEQ ID NO: 1;
b) the first antigen binding portion VL comprises the amino acid sequence of SEQ ID NO: 2;
c) the second antigen binding portion VH comprises the amino acid sequence of SEQ ID NO: 4; and
d) the second antigen binding portion VL comprises the amino acid sequence of SEQ ID NO: 2.

15. The bispecific antibody of claim 13, wherein the bispecific antibody comprises a Fc domain.

16. The bispecific antibody of claim 15, wherein the Fc domain is an IgG1 Fc domain, IgG2 Fc domain, or an IgG4 Fc domain.

17. The bispecific antibody of claim 15, wherein the Fc domain comprises a first Fc chain and a second Fc chain, and wherein the first Fc chain and the second Fc chain contain one or more modifications promoting the association of the first Fc chain with the second Fc chain.

18. The bispecific antibody of claim 15, wherein the antibody comprises an anti-CD47 heavy chain comprising the amino acid sequence of SEQ ID NO: 61 and the antibody comprises an anti-PD-L1 heavy chain comprising the amino acid sequence of SEQ ID NO: 64.

19. The bispecific antibody of claim 15, wherein the antibody comprises an anti-CD47 light chain comprising the amino acid sequence of SEQ ID NO: 62 and an anti-PD-L1 light chain comprising the amino acid sequence of SEQ ID NO: 62.

20. The bispecific antibody of claim 15,
wherein the antibody comprises a first antibody heavy chain, a second antibody heavy chain, a first antibody light chain, and a second antibody light chain;
wherein the first antibody heavy chain comprises the amino acid sequence of SEQ ID NO: 61 and the second antibody heavy chain comprises the amino acid sequence of SEQ ID NO: 64; and
wherein both the first antibody light chain and the second antibody light chain comprise the amino acid sequence of SEQ ID NO: 62.

21. The bispecific antibody of claim 13, wherein the affinity of the anti-PD-L1 antigen binding portion for PD-L1 is greater than the affinity of the anti-CD47 antigen binding portion for CD47.

22. A pharmaceutical composition comprising a therapeutically effective amount of the antibody of any one of claims 1-8 or the bispecific antibody of any one of claim 9-13, 14, or 15-21, and a pharmaceutically acceptable carrier.

23. The antibody of claim 5, wherein the antibody is a bispecific antibody.

24. The antibody of claim 23, wherein the bispecific antibody specifically binds to CD47 and PD-L1.

25. The antibody of claim 24, wherein the antibody comprises a first antigen binding portion and a second antigen binding portion, wherein the first antigen binding portion specifically binds to CD47 and the second antigen binding portion specifically binds to PD-L1, wherein the first antigen binding portion comprises a first antigen binding portion VH and a first antigen binding portion VL, wherein the second antigen binding portion comprises a second antigen binding portion VH and a second antigen binding portion VL, and wherein the amino acid sequence of the first antigen binding portion VL and the amino acid sequence of the second antigen binding portion VL have the same amino acid sequence.

26. The antibody of claim 25, wherein the amino acid sequence of the first antigen binding portion VL and the amino acid sequence of the second antigen binding portion VL each comprise the amino acid sequence as shown in SEQ ID NO: 2.

27. An isolated bispecific antibody that specifically binds to CD47 and PD-L1, wherein the antibody comprises a first antibody heavy chain, a second antibody heavy chain, a first antibody light chain, and a second antibody light chain;
    wherein the first antibody heavy chain comprises the amino acid sequence of SEQ ID NO: 61 and the second antibody heavy chain comprises the amino acid sequence of SEQ ID NO: 64; and
    wherein both the first antibody light chain and the second antibody light chain comprise the amino acid sequence of SEQ ID NO: 62.

\* \* \* \* \*

```
                           SEQUENCE LISTING

<160> NUMBER OF SEQ ID NOS: 76

<210> SEQ ID NO 1
<211> LENGTH: 126
<212> TYPE: PRT
<213> ORGANISM: Artificial Sequence
<220> FEATURE:
<223> OTHER INFORMATION: Synthetic Peptide Sequence

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Arg Ser Ser Asp Val Gly Trp Tyr Val Gly Ala
            100                 105                 110

Ile Asp Val Trp Gly Gln Gly Thr Leu Val Thr Val Ser Ser
        115                 120                 125

<210> SEQ ID NO 2
<211> LENGTH: 110
<212> TYPE: PRT
<213> ORGANISM: Artificial Sequence
<220> FEATURE:
<223> OTHER INFORMATION: Synthetic Peptide Sequence

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
```

```
                35                  40                  45
Ile Tyr Arg Asn Asn Gln Arg Pro Ser Gly Val Pro Asp Arg Phe Ser
 50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                 85                  90                  95
Ser Gly Val Val Phe Gly Gly Gly Thr Lys Leu Thr Val Leu
            100                 105                 110
```

<210> SEQ ID NO 3
<211> LENGTH: 126
<212> TYPE: PRT
<213> ORGANISM: Artificial Sequence
<220> FEATURE:
<223> OTHER INFORMATION: Synthetic Peptide Sequence

<400> SEQUENCE: 3

```
Gln Val Gln Leu Val Gln Ser Gly Ala Glu Val Lys Lys Pro Gly Ser
  1               5                  10                  15
Ser Val Lys Val Ser Cys Lys Ala Ser Gly Gly Thr Phe Thr Ser Tyr
                 20                  25                  30
Ala Ile Ser Trp Val Arg Gln Ala Pro Gly Gln Gly Leu Glu Trp Met
                 35                  40                  45
Gly Gly Ile Ser Pro Ile Phe Gly Thr Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Ala Gly Arg Ser Ser Asp Val Gly Trp Tyr Val Gly Ala
            100                 105                 110
Leu Asp Val Trp Gly Gln Gly Thr Leu Val Thr Val Ser Ser
            115                 120                 125
```

<210> SEQ ID NO 4
<211> LENGTH: 126
<212> TYPE: PRT
<213> ORGANISM: Artificial Sequence
<220> FEATURE:
<223> OTHER INFORMATION: Synthetic peptide sequence

<400> SEQUENCE: 4

```
Glu Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Asn Ala
                 20                  25                  30
Trp Met Asn Trp Val Arg Gln Ala Pro Gly Lys Gly Leu Glu Trp Val
                 35                  40                  45
Gly Arg Ile Lys Thr Lys Ala Asp Gly Gly Thr Thr Asp Tyr Ala Ala
 50                  55                  60
Pro Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                 85                  90                  95
Tyr Cys Thr Thr Asp Pro Gly Glu Tyr Trp Asp Ser Val Tyr Gly Gly
            100                 105                 110
```

```
Met Asp Tyr Trp Gly Gln Gly Thr Leu Val Thr Val Ser Ser
            115                 120                 125
```

<210> SEQ ID NO 5
<211> LENGTH: 124
<212> TYPE: PRT
<213> ORGANISM: Artificial Sequence
<220> FEATURE:
<223> OTHER INFORMATION: Synthetic peptide sequence

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Val Arg Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ser Val Gly Glu Leu Val Gly Ile Asp Gln Met Asp
            100                 105                 110

His Trp Gly Gln Gly Thr Leu Val Thr Val Ser Ser
            115                 120
```

<210> SEQ ID NO 6
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 7
<211> LENGTH: 126
<212> TYPE: PRT
<213> ORGANISM: Artificial Sequence
<220> FEATURE:
<223> OTHER INFORMATION: Synthetic peptide sequence

<400> SEQUENCE: 7

```
Gln Val Gln Leu Val Gln Ser Gly Ala Glu Val Lys Lys Pro Gly Ser
```

```
1               5                   10                  15
Ser Val Lys Val Ser Cys Lys Ala Ser Gly Tyr Thr Phe Thr Asn Tyr
                20                  25                  30

Ala Ile Ser Trp Val Arg Gln Ala Pro Gly Gln Gly Leu Glu Trp Met
            35                  40                  45

Gly Gly Ile Ser Pro Leu Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Arg Ser Ser Asp Val Gly Trp Tyr Val Gly Ala
                100                 105                 110

Met Asp Val Trp Gly Gln Gly Thr Leu Val Thr Val Ser Ser
            115                 120                 125
```

<210> SEQ ID NO 8
<211> LENGTH: 125
<212> TYPE: PRT
<213> ORGANISM: Artificial Sequence
<220> FEATURE:
<223> OTHER INFORMATION: Synthetic peptide sequence

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Thr Phe
                20                  25                  30

Thr Met Asn Trp Val Arg Gln Ala Pro Gly Lys Gly Leu Glu Trp Val
            35                  40                  45

Ser Thr Ile Ser Gly Thr Gly Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Ser Thr Val Gly Ser Asn Gly His Ser Tyr Trp Phe
                100                 105                 110

Asp Tyr Trp Gly Gln Gly Thr Leu Val Thr Val Ser Ser
            115                 120                 125
```

<210> SEQ ID NO 9
<211> LENGTH: 126
<212> TYPE: PRT
<213> ORGANISM: Artificial Sequence
<220> FEATURE:
<223> OTHER INFORMATION: Synthetic Peptide Sequence

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
                20                  25                  30

Ala Ile Thr Trp Val Arg Gln Ala Pro Gly Gln Gly Leu Glu Trp Met
            35                  40                  45

Gly Gly Ile Ser Pro Ile Phe Gly Thr Ala Asn Tyr Ala Gln Lys Phe
        50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Gly Arg Ser Ser Asp Gly Gly Trp Arg Gly Ala Gly
            100                 105                 110

Met Asp Tyr Trp Gly Gln Gly Thr Leu Val Thr Val Ser Ser
        115                 120                 125

<210> SEQ ID NO 10
<211> LENGTH: 124
<212> TYPE: PRT
<213> ORGANISM: Artificial Sequence
<220> FEATURE:
<223> OTHER INFORMATION: Synthetic Peptide Sequence

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Val Arg Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Ser Val Gly Glu Leu Val Gly Ile Asp Trp Met Asp
            100                 105                 110

His Trp Gly Gln Gly Thr Leu Val Thr Val Ser Ser
        115                 120

<210> SEQ ID NO 11
<211> LENGTH: 126
<212> TYPE: PRT
<213> ORGANISM: Artificial Sequence
<220> FEATURE:
<223> OTHER INFORMATION: Synthetic Peptide Sequence

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Thr Lys Ala Asp Gly Gly Thr Thr Asp Tyr Ala Ala
    50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Asp Pro Gly Ser Tyr Trp Asp Ser Val Tyr Gly Gly
            100                 105                 110

Met Asp Tyr Trp Gly Gln Gly Thr Leu Val Thr Val Ser Ser
        115                 120                 125
```

```
<210> SEQ ID NO 12
<211> LENGTH: 127
<212> TYPE: PRT
<213> ORGANISM: Artificial Sequence
<220> FEATURE:
<223> OTHER INFORMATION: Synthetic Peptide Sequence

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Glu Ser Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Tyr Arg Ile Asp Asp Trp Gly Tyr Pro Tyr Pro
            100                 105                 110

Gly Met Asp Tyr Trp Gly Gln Gly Thr Leu Val Thr Val Ser Ser
        115                 120                 125

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 13

Gly Tyr Thr Phe Ser Ser Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 14

Ser Tyr Ala Ile Ser
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 15

Gly Tyr Thr Phe Ser Ser Tyr Ala Ile Ser
1               5                   10

<210> SEQ ID NO 16
<211> LENGTH: 6
<212> TYPE: PRT
<213> ORGANISM: Artificial Sequence
```

```
<220> FEATURE:
<223> OTHER INFORMATION: Synthetic Peptide Sequence

<400> SEQUENCE: 16

Ser Pro Ile Phe Gly Thr
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 17

Gly Ile Ser Pro Ile Phe Gly Thr Ala Asn Tyr Ala Gln Lys Phe Gln
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 18

Asp Ala Gly Arg Ser Ser Asp Val Gly Trp Tyr Val Gly Ala Ile Asp
1               5                   10                  15

Val

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide Sequence

<400> SEQUENCE: 19

Ser Gly Ser Ser Ser Asn Ile Gly Ser Asn Tyr Val Tyr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 20

Arg Asn Asn Gln Arg Pro Ser
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 21

Ala Ala Trp Asp Asp Ser Leu Ser Gly Val Val
1               5                   10

<210> SEQ ID NO 22
```

```
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 22

Gly Gly Thr Phe Thr Ser Tyr
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 23

Gly Gly Thr Phe Thr Ser Tyr Ala Ile Ser
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 24

Asp Ala Gly Arg Ser Ser Asp Val Gly Trp Tyr Val Gly Ala Leu Asp
1               5                   10                  15
Val

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 25

Gly Tyr Thr Phe Thr Asn Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 26

Asn Tyr Ala Ile Ser
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 27

Gly Tyr Thr Phe Thr Asn Tyr Ala Ile Ser
1               5                   10
```

```
<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide Sequence

<400> SEQUENCE: 28

Ser Pro Leu Phe Gly Thr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 29

Gly Ile Ser Pro Leu Phe Gly Thr Ala Asn Tyr Ala Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 30

Asp Gly Gly Arg Ser Ser Asp Val Gly Trp Tyr Val Gly Ala Met Asp
1               5                   10                  15

Val

<210> SEQ ID NO 31
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 31

Gly Phe Ser Phe Ser Thr Phe
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 32

Thr Phe Thr Met Asn
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 33

Gly Phe Ser Phe Ser Thr Phe Thr Met Asn
```

<210> SEQ ID NO 34
<211> LENGTH: 6
<212> TYPE: PRT
<213> ORGANISM: Artificial Sequence
<220> FEATURE:
<223> OTHER INFORMATION: Synthetic Peptide Sequence

<400> SEQUENCE: 34

Ser Gly Thr Gly Gly Asn
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 35

Thr Ile Ser Gly Thr Gly Gly Asn Thr Tyr Tyr Ala Asp Ser Val Lys
1               5                   10                  15

Gly

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide Sequence

<400> SEQUENCE: 36

Arg Arg Ser Thr Val Gly Ser Asn Gly His Ser Tyr Trp Phe Asp Tyr
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 37

Gly Tyr Thr Phe Ser Asn Tyr
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 38

Asn Tyr Ala Ile Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 39

Gly Tyr Thr Phe Ser Asn Tyr Ala Ile Thr
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 40

Asp Gly Gly Arg Ser Ser Asp Gly Gly Trp Arg Gly Ala Gly Met Asp
1               5                   10                  15

Tyr

<210> SEQ ID NO 41
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 41

Gly Phe Thr Phe Ser Asn Ala
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 42

Asn Ala Trp Met Asn
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 43

Gly Phe Thr Phe Ser Asn Ala Trp Met Asn
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic Peptide Sequence

<400> SEQUENCE: 44

Lys Thr Lys Ala Asp Gly Gly Thr
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic Peptide Sequence

<400> SEQUENCE: 45

Arg Ile Lys Thr Lys Ala Asp Gly Gly Thr Thr Asp Tyr Ala Ala Pro
1               5                   10                  15

Val Lys Gly

<210> SEQ ID NO 46
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 46

Asp Pro Gly Glu Tyr Trp Asp Ser Val Tyr Gly Gly Met Asp Tyr
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 47

Gly Phe Thr Phe Ser Ser Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 48

Ser Tyr Ala Met Ser
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 49

Gly Phe Thr Phe Ser Ser Tyr Ala Met Ser
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Synthetic Peptide Sequence

<400> SEQUENCE: 50

Gly Val Arg Gly Gly Ile
1               5

<210> SEQ ID NO 51
<211> LENGTH: 17
<212> TYPE: PRT
<213> ORGANISM: Artificial Sequence
<220> FEATURE:
<223> OTHER INFORMATION: Synthetic Peptide Sequence -continued

```
<400> SEQUENCE: 51

Ala Ile Gly Val Arg Gly Gly Ile Thr Tyr Tyr Ala Asp Ser Val Lys
1               5                   10                  15

Gly

<210> SEQ ID NO 52
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 52

Glu Arg Ser Val Gly Glu Leu Val Gly Ile Asp Gln Met Asp His
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 53

Arg Ala Ser Gln Ser Ile Ser Ser Tyr Leu Asn
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 54

Ala Ala Ser Ser Leu Gln Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 55

Gln Gln Ser Tyr Ser Thr Pro Leu Thr
1               5

<210> SEQ ID NO 56
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 56

Glu Arg Ser Val Gly Glu Leu Val Gly Ile Asp Trp Met Asp His
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic Peptide Sequence
```

-continued

```
<400> SEQUENCE: 57

Asp Pro Gly Ser Tyr Trp Asp Ser Val Tyr Gly Gly Met Asp Tyr
1               5                   10                  15

<210> SEQ ID NO 58
<211> LENGTH: 8
<212> TYPE: PRT
<213> ORGANISM: Artificial Sequence
<220> FEATURE:
<223> OTHER INFORMATION: Synthetic Peptide Sequence

<400> SEQUENCE: 58

Lys Ser Glu Ser Asp Gly Gly Thr
1               5

<210> SEQ ID NO 59
<211> LENGTH: 19
<212> TYPE: PRT
<213> ORGANISM: Artificial Sequence
<220> FEATURE:
<223> OTHER INFORMATION: Synthetic Peptide Sequence

<400> SEQUENCE: 59

Arg Ile Lys Ser Glu Ser Asp Gly Gly Thr Thr Asp Tyr Ala Ala Pro
1               5                   10                  15

Val Lys Gly

<210> SEQ ID NO 60
<211> LENGTH: 16
<212> TYPE: PRT
<213> ORGANISM: Artificial Sequence
<220> FEATURE:
<223> OTHER INFORMATION: Synthetic Peptide Sequence

<400> SEQUENCE: 60

Asp Tyr Arg Ile Asp Asp Trp Gly Tyr Pro Tyr Pro Gly Met Asp Tyr
1               5                   10                  15

<210> SEQ ID NO 61
<211> LENGTH: 456
<212> TYPE: PRT
<213> ORGANISM: Artificial Sequence
<220> FEATURE:
<223> OTHER INFORMATION: Synthetic Peptide Sequence

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Arg Ser Ser Asp Val Gly Trp Tyr Val Gly Ala
            100                 105                 110

Ile Asp Val Trp Gly Gln Gly Thr Leu Val Thr Val Ser Ser Ala Ser
```

```
                    115                 120                 125
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 62
<211> LENGTH: 216
<212> TYPE: PRT
<213> ORGANISM: Artificial Sequence
<220> FEATURE:
<223> OTHER INFORMATION: Synthetic Peptide Sequence

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
```

```
                20                  25                  30
Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 63
<211> LENGTH: 456
<212> TYPE: PRT
<213> ORGANISM: Artificial Sequence
<220> FEATURE:
<223> OTHER INFORMATION: Synthetic Peptide Sequence

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Arg Ser Ser Asp Val Gly Trp Tyr Val Gly Ala
            100                 105                 110

Leu Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
```

165                 170                 175
His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 64
<211> LENGTH: 456
<212> TYPE: PRT
<213> ORGANISM: Artificial Sequence
<220> FEATURE:
<223> OTHER INFORMATION: Synthetic Peptide Sequence

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Thr Lys Ala Asp Gly Gly Thr Thr Asp Tyr Ala Ala
    50                  55                  60

Pro Val Lys Gly Arg Phe Thr Ile Ser Arg Asp Asp Ser Lys Asn Thr

```
                65                  70                  75                  80
Leu Tyr Leu Gln Met Asn Ser Leu Lys Thr Glu Asp Thr Ala Val Tyr
                    85                  90                  95

Tyr Cys Thr Thr Asp Pro Gly Glu Tyr Trp Asp Ser Val Tyr Gly Gly
                100                 105                 110

Met Asp Tyr Trp Gly Gln Gly Thr Leu Val Thr Val Ser Ala Ser
                115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
                210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Cys Thr Leu Pro Pro Ser Arg Glu Glu Met Thr
                355                 360                 365

Lys Asn Gln Val Ser Leu Trp Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
    450                 455

<210> SEQ ID NO 65
<211> LENGTH: 330
<212> TYPE: PRT
<213> ORGANISM: Artificial Sequence
```

<220> FEATURE:
<223> OTHER INFORMATION: Synthetic Peptide Sequence

<400> SEQUENCE: 65

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 66
<211> LENGTH: 330
<212> TYPE: PRT
<213> ORGANISM: Artificial Sequence
<220> FEATURE:
<223> OTHER INFORMATION: Synthetic Peptide Sequence

<400> SEQUENCE: 66

Ala Ser Thr Lys Gly Pro Ser Val Phe Pro Leu Ala Pro Ser Ser Lys

```
  1               5                  10                 15
Ser Thr Ser Gly Gly Thr Ala Ala Leu Gly Cys Leu Val Lys Asp Tyr
              20                  25                 30

Phe Pro Glu Pro Val Thr Val Ser Trp Asn Ser Gly Ala Leu Thr Ser
              35                  40                 45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
              85                  90                 95

Lys Val Glu Pro Lys Ser Cys Asp Lys Thr His Thr Cys Pro Pro Cys
             100                 105                110

Pro Ala Pro Glu Leu Leu Gly Gly Pro Ser Val Phe Leu Phe Pro Pro
             115                 120                125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                160

Tyr Val Asp Gly Val Glu Val His Asn Ala Lys Thr Lys Pro Arg Glu
             165                 170                175

Glu Gln Tyr Asn Ser Thr Tyr Arg Val Val Ser Val Leu Thr Val Leu
             180                 185                190

His Gln Asp Trp Leu Asn Gly Lys Glu Tyr Lys Cys Lys Val Ser Asn
             195                 200                205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Cys Arg Glu Glu
225                 230                 235                240

Met Thr Lys Asn Gln Val Ser Leu Ser Cys Ala Val Lys Gly Phe Tyr
             245                 250                255

Pro Ser Asp Ile Ala Val Glu Trp Glu Ser Asn Gly Gln Pro Glu Asn
             260                 265                270

Asn Tyr Lys Thr Thr Pro Pro Val Leu Asp Ser Asp Gly Ser Phe Phe
             275                 280                285

Leu Val Ser Lys Leu Thr Val Asp Lys Ser Arg Trp Gln Gln Gly Asn
             290                 295                300

Val Phe Ser Cys Ser Val Met His Glu Ala Leu His Asn His Tyr Thr
305                 310                 315                320

Gln Lys Ser Leu Ser Leu Ser Pro Gly Lys
             325                 330
```

<210> SEQ ID NO 67
<211> LENGTH: 378
<212> TYPE: DNA
<213> ORGANISM: Artificial Sequence
<220> FEATURE:
<223> OTHER INFORMATION: Synthetic polynucleotide sequence

<400> SEQUENCE: 67

```
caagtgcaac tggtgcagtc aggcgccgaa gtcaagaagc cggggtctag cgtgaaagtg    60
tcgtgcaagg cctcaggcta caccttctcc tcctatgcga tcagctgggt cagacaggcg   120
cctggacagg gactcgagtg gatgggtggc atttccccca tcttcggaac cgcaaactac   180
gcccagaagt tcagggccg cgtgaccatc actgccgacg agagcacttc gaccgcctac   240
```

```
atggaactgt cctcgctgcg gtccgaagat accgccgtgt actactgtgc tcgggatgct    300
ggaaggtcct ccgacgtcgg ttggtacgtg ggggccattg acgtctgggg acagggaact    360
ctggtcaccg tctcctca                                                  378
```

<210> SEQ ID NO 68
<211> LENGTH: 330
<212> TYPE: DNA
<213> ORGANISM: Artificial Sequence
<220> FEATURE:
<223> OTHER INFORMATION: synthetic polynucleotide sequence

<400> SEQUENCE: 68

```
caatcagtgc tgacccagcc tccctctgca tccggaaccc cgggacagag agtcaccatc     60
tcctgctccg gttcgtcctc gaacatcggc agcaactacg tgtactggta ccagcaactc    120
cctgggactg ccccaaagct gctcatctat cggaacaatc agcggccttc cggagtgccg    180
gacaggttct ccggaagcaa atcgggcact agcgcctcac tggctattag cggtttgcgc    240
tccgaggacg aagccgacta ctactgtgcc gcgtgggatg attcccttt cggcgtcgtg     300 ttcggggcg aaccaagct gactgtgcta                                       330
```

<210> SEQ ID NO 69
<211> LENGTH: 378
<212> TYPE: DNA
<213> ORGANISM: Artificial Sequence
<220> FEATURE:
<223> OTHER INFORMATION: synthetic polynucleotide sequence

<400> SEQUENCE: 69

```
caagtgcagc ttgtgcagtc gggcgctgaa gtcaagaagc tgggtcatc ggtgaaagtg      60 tcctgcaagg cctctggggg aaccttcacg tcctacgcga ttagctgggt ccgccaagca    120
ccgggacagg gactggagtg gatgggcgga atcagcccca tcttcggcac tgccaactac    180
gcccagaagt ttcagggtcg cgtgactatc accgccgacg aatccacctc aaccgcctac    240
atggaactga ctcccctgcg gtccgaggac actgccgtgt attactgtgc gagagatgct    300
ggacggtcgt ccgatgtcgg ttggtacgtg ggagccctcg acgtctgggg acagggcacc    360
ctggtcaccg tctcctca                                                  378
```

<210> SEQ ID NO 70
<211> LENGTH: 378
<212> TYPE: DNA
<213> ORGANISM: Artificial Sequence
<220> FEATURE:
<223> OTHER INFORMATION: synthetic polynucleotide sequence

<400> SEQUENCE: 70

```
gaagtgcagc tggttgaaag cggtggtggc ctggtcaaac tggtggtag cctgcgtctg      60 agctgtgcgg cgtcaggttt tacgttctca aatgcgtgga tgaattgggt cagacaggcg    120
cccggaaagg gactggaatg ggtcgggcgc attaaaacaa aggctgatgg cggtactacc    180
gattatgcag cgccggtgaa aggacgtttt accatctcac gtgacgattc gaaaaacacc    240
ctgtaccttc agatgaacag cctgaaaacc gaggacaccg cagtatacta ttgcactacc    300
gacccgggcg agtactggga tagcgtttat ggcggtatgg attactgggg ccaaggtaca    360
ctggtcaccg tctcctca                                                  378
```

<210> SEQ ID NO 71

<211> LENGTH: 1368
<212> TYPE: DNA
<213> ORGANISM: Artificial Sequence
<220> FEATURE:
<223> OTHER INFORMATION: synthetic polynucleotide sequence

<400> SEQUENCE: 71

```
caagtgcaac tggtgcagtc aggcgccgaa gtcaagaagc cggggtctag cgtgaaagtg      60
tcgtgcaagg cctcaggcta caccttctcc tcctatgcga tcagctgggt cagacaggcg     120
cctggacagg gactcgagtg gatgggtggc atttccccca tcttcggaac cgcaaactac     180
gcccagaagt tcagggccg cgtgaccatc actgccgacg agagcacttc gaccgcctac     240
atggaactgt cctcgctgcg gtccgaagat accgccgtgt actactgtgc tcgggatgct     300
ggaaggtcct ccgacgtcgg ttggtacgtg ggggccattg acgtctgggg cagggaact     360
ctggtcaccg tctcctcagc gtcgaccaag ggcccatcgg tcttcccct ggcaccctcc     420
tccaagagca cctctggggg cacagcggcc ctgggctgcc tggtcaagga ctacttcccc     480
gaaccggtga cggtgtcgtg gaactcaggc gccctgacca cgccgtgca cccttcccg     540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagaaag ttgagcccaa atcttgtgac aaaactcaca catgcccacc gtgcccagca     720
cctgaactcc tggggggacc gtcagtcttc ctcttccccc caaaacccaa ggacaccctc     780
atgatctccc ggaccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatgcc gggaggagat gaccaagaac caggtcagcc tgtcctgcgc ggtcaaaggc    1140
ttctatccca gcgacatcgc cgtggagtgg gagagcaatg ggcagccgga gaacaactac    1200
aagaccacgc ctcccgtgct ggactccgac ggctccttct tcctcgttag caagctcacc    1260
gtggacaaga gcaggtggca gcaggggaac gtcttctcat gctccgtgat gcatgaggct    1320
ctgcacaacc actacacgca gaagagcctc tccctgtccc ccggaaaa                  1368
```

<210> SEQ ID NO 72
<211> LENGTH: 648
<212> TYPE: DNA
<213> ORGANISM: Artificial Sequence
<220> FEATURE:
<223> OTHER INFORMATION: synthetic polynucleotide sequence

<400> SEQUENCE: 72

```
caatcagtgc tgacccagcc tccctctgca tccggaaccc cgggacagag agtcaccatc      60
tcctgctccg gttcgtcctc gaacatcggc agcaactacg tgtactggta ccagcaactc     120
cctgggactg ccccaaagct gctcatctat cggaacaatc agcggccttc cggagtgccg     180
gacaggttct ccggaagcaa atcgggcact agcgcctcac tggctattag cggtttgcgc     240
tccgaggacg aagccgacta ctactgtgcc gcgtgggatg attccctttc cggcgtcgtg     300
ttcggggggcg gaaccaagct gactgtgcta ggtcagccca aggctgcccc ctcggtcact     360
ctgttcccac cctcctctga ggagcttcaa gccaacaagg ccacactggt gtgtctcata     420
agtgacttct acccgggagc cgtgacagtg gcctggaagg cagatagcag ccccgtcaag    480
```

| | | |
|---|---|---|
| gcgggagtgg agaccaccac accctccaaa caaagcaaca acaagtacgc ggccagcagc | 540 | |
| tacctgagcc tgacgcctga gcagtggaag tcccacagaa gctacagctg ccaggtcacg | 600 | |
| catgaaggga gcaccgtgga gaagacagtg gcccctacag aatgttca | 648 | |

<210> SEQ ID NO 73
<211> LENGTH: 1368
<212> TYPE: DNA
<213> ORGANISM: Artificial Sequence
<220> FEATURE:
<223> OTHER INFORMATION: synthetic polynucleotide sequence

<400> SEQUENCE: 73

| | |
|---|---|
| caagtgcagc ttgtgcagtc gggcgctgaa gtcaagaagc ctgggtcatc ggtgaaagtg | 60 |
| tcctgcaagg cctctggggg aaccttcacg tcctacgcga ttagctgggt ccgccaagca | 120 |
| ccgggacagg gactggagtg gatgggcgga atcagcccca tcttcggcac tgccaactac | 180 |
| gcccagaagt ttcagggtcg cgtgactatc accgccgacg aatccacctc aaccgcctac | 240 |
| atggaactga gctccctgcg gtccgaggac actgccgtgt attactgtgc gagagatgct | 300 |
| ggacggtcgt ccgatgtcgg ttggtacgtg ggagccctcg acgtctgggg acagggcacc | 360 |
| ctggtcaccg tctcctcagc gtcgaccaag ggcccatcgg tcttcccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagaaag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggg cagccccgag aaccacaggt gtacaccctg | 1080 |
| cccccatgcc gggaggagat gaccaagaac caggtcagcc tgtcctgcgc ggtcaaaggc | 1140 |
| ttctatccca gcgacatcgc cgtggagtgg gagagcaatg ggcagccgga gaacaactac | 1200 |
| aagaccacgc ctcccgtgct ggactccgac ggctccttct tcctcgttag caagctcacc | 1260 |
| gtggacaaga gcaggtggca gcagggaaac gtcttctcat gctccgtgat gcatgaggct | 1320 |
| ctgcacaacc actacacgca gaagagcctc tccctgtccc cggaaaa | 1368 |

<210> SEQ ID NO 74
<211> LENGTH: 1368
<212> TYPE: DNA
<213> ORGANISM: Artificial Sequence
<220> FEATURE:
<223> OTHER INFORMATION: synthetic polynucleotide sequence

<400> SEQUENCE: 74

| | |
|---|---|
| gaagtgcagc tggttgaaag cggtggtggc ctggtcaaac tggtggtag cctgcgtctg | 60 |
| agctgtgcgg cgtcaggttt tacgttctca aatgcgtgga tgaattgggt cagacaggcg | 120 |
| cccggaaagg gactggaatg ggtcgggcgc attaaaacaa aggctgatgg cggtactacc | 180 |

-continued

```
gattatgcag cgccggtgaa aggacgtttt accatctcac gtgacgattc gaaaaacacc    240
ctgtaccttc agatgaacag cctgaaaacc gaggacaccg cagtatacta ttgcactacc    300
gacccgggcg agtactggga tagcgtttat ggcggtatgg attactgggg ccaaggtaca    360
ctggtcaccg tctcctcagc gtcgaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtgcaccctg   1080
cccccatccc gggaggagat gaccaagaac caggtcagcc tgtggtgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctatag caagctcacc   1260
gtggacaaga gcaggtggca gcaggggaac gtcttctcat gctccgtgat gcatgaggct   1320
ctgcacaacc actacacgca gaagagcctc tccctgtccc ccggaaaa              1368
```

<210> SEQ ID NO 75
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 75

Gly Gly Gly Gly Ser
1               5

<210> SEQ ID NO 76
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 76

Gly Gly Gly Gly Ser His His His His His His
1               5                   10